(12) United States Patent
Richardson et al.

(10) Patent No.: US 7,807,374 B2
(45) Date of Patent: *Oct. 5, 2010

(54) METHODS AND KITS FOR DIAGNOSING OR MONITORING AUTOIMMUNE AND CHRONIC INFLAMMATORY DISEASES

(75) Inventors: Bruce Richardson, Ann Arbor, MI (US); Qianjin Lu, Ann Arbor, MI (US)

(73) Assignees: The Regents of the University of Michigan, Ann Arbor, MI (US); The United States of America as represented by the Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/254,550

(22) Filed: Oct. 20, 2008

(65) Prior Publication Data

US 2009/0123929 A1    May 14, 2009

Related U.S. Application Data

(62) Division of application No. 11/445,415, filed on Jun. 1, 2006, now Pat. No. 7,439,024.

(60) Provisional application No. 60/686,223, filed on Jun. 1, 2005.

(51) Int. Cl.
  *C12Q 1/68* (2006.01)
  *C12P 19/34* (2006.01)

(52) U.S. Cl. .......................................... 435/6; 435/91.2

(58) Field of Classification Search ........................ None
See application file for complete search history.

(56) References Cited

U.S. PATENT DOCUMENTS

| | | | |
|---|---|---|---|
| 4,981,785 A | 1/1991 | Nayak et al. | |
| 5,358,692 A | 10/1994 | Reynolds | |
| 5,538,848 A | 7/1996 | Livak et al. | |
| 5,552,277 A * | 9/1996 | Nelson et al. | 435/6 |
| 5,599,677 A | 2/1997 | Dowell et al. | |
| 5,639,606 A | 6/1997 | Willey | |
| 5,643,765 A | 7/1997 | Willey | |
| 5,672,480 A | 9/1997 | Dowell et al. | |
| 5,781,146 A | 7/1998 | Frederick | |
| 5,786,146 A * | 7/1998 | Herman et al. | 435/6 |
| 5,846,717 A | 12/1998 | Brow et al. | |
| 5,856,094 A * | 1/1999 | Sidransky et al. | 435/6 |
| 5,876,978 A | 3/1999 | Willey et al. | |
| 5,885,530 A | 3/1999 | Babson et al. | |
| 5,985,557 A | 11/1999 | Prudent et al. | |
| 5,994,069 A | 11/1999 | Hall et al. | |
| 6,001,567 A | 12/1999 | Brow et al. | |
| 6,017,704 A | 1/2000 | Herman et al. | |
| 6,090,543 A | 7/2000 | Prudent et al. | |
| 6,159,750 A | 12/2000 | Edmonds | |
| 6,200,756 B1 | 3/2001 | Herman et al. | |
| 6,214,556 B1 * | 4/2001 | Olek et al. | 435/6 |
| 6,251,594 B1 * | 6/2001 | Gonzalgo et al. | 435/6 |
| 6,264,171 B1 * | 7/2001 | Hoium et al. | 254/134.4 |
| 6,265,171 B1 | 7/2001 | Herman et al. | |
| 6,897,069 B1 | 5/2005 | Jarvis et al. | |
| 7,279,281 B2 * | 10/2007 | Richardson et al. | 435/6 |
| 2004/0053876 A1 * | 3/2004 | Turner et al. | 514/44 |

FOREIGN PATENT DOCUMENTS

| WO | WO 01/77373 | 10/2001 |
|---|---|---|
| WO | WO 2005/118872 | 12/2005 |

OTHER PUBLICATIONS de Saint Basile et al., (Eur J Immunol. Jan. 1999;29(1):367-73).*
Richardson, J Nutr. Aug. 2002; 132:2401S-2405S.*
Attwood et al., Cell Mol Life Sci. Feb. 2002; 59(2):241-257.*
Muegge et al., (Ann NY Acad Sci. Mar. 7, 2003;983:55-70. Review.*
Richardson et al., Arth Rheum. Nov. 1990;33(11):1665-1673.*
Liossis et al., Clin Exp Rheum. Nov.-Dec. 1997;15(6):677-84.*
Morimoto et al., J Immunol. Apr. 15, 2000;164(8):4097-104.*
Nakajima et al., J Neuroimmunology 2000 109:188-196.*
Lu et al., J Immunol, May 15, 2003;170(10):5124-32.*
UniProtKB/SwissProt P29965 (CD40L_Human) (Apr. 1, 1993).*
Muegge et al., Ann NY Acad Sci. Mar. 7, 2003;983:55-70. Review.
Mikovits et al., Mol and Cellular Biol. Sep. 1998; 18(9):5166-5177.
Januchowski et al., J Appl Genet 2004; 45(2):237-248.
Courdec et al. Nature. May-Jun. 1998; 5(3):163-75.
Jacquot et al., J Immunol. Sep. 15, 1997;159(6):2652-7.
Kaplan et al., J Immunol. Mar. 15, 2004; 172(6):3652-61.
Muegge et al., Ann NY Acad Sci. Mar. 7, 2003;983:55-70.
Wang et al., Cell Immunol. Sep. 15, 1997;180(2):162-7.
Liossis et al., (Clin Exp Rheum. Nov.-Dec. 1997;15(6):677-84).
Richardson et al., (Arth Rheum. Nov. 1990;33(11):1665-1673).
Attwood et al., "DNA methylation and the regulation of gene transcription," Cell Mol Life Sci 59, 241 (2002).
Cornacchia et al., "Hydralazine and procainamide inhibit T cell DNA methylation and induce autoreactivity," J Immunol 140, 2197 (1988).
Richardson et al., "CD4+ cells treated with DNA methylation inhibitors induce autologous B cell differentiation," Clin Immunol Immunopathol 55, 368 (1990).

(Continued)

*Primary Examiner*—Cherie M Woodward
(74) *Attorney, Agent, or Firm*—Casimir Jones S.C.

(57) ABSTRACT

The present invention relates to compositions and methods for diagnosing, monitoring and/or treating an autoimmune or chronic inflammatory disease. In particular, the present invention provides methods for diagnosing, monitoring and treating an autoimmune disease (e.g., rheumatoid arthritis) or chronic inflammatory disease (e.g., systemic lupus erythematosus) based on detecting or altering (e.g., altering expression or methylation status of) autoimmune or chronic inflammatory disease proteins (e.g., CD70 and CD40L). The present invention also provides kits for detecting methylation status of autoimmune or chronic inflammatory disease proteins (e.g., CD70 and CD40L) and for diagnosing, monitoring and/or treating autoimmune or chronic inflammatory diseases.

13 Claims, 29 Drawing Sheets

OTHER PUBLICATIONS

Yu et al., "Two Types of Ia-Positive T Cells," J Exp Med 152 89s (1980).

Quddus et al., "Treating activated CD4+ T cells with either of two distinct DNA methyltransferase inhibitors, 5-azacytidine or procainamide, is sufficient to cause a lupus-like disease in syngeneic mice," J Clin Invest 92, 38 (1993).

Richardson et al., "Lymphocyte function-associated antigen 1 overexpression and T cell autoreactivity," Arthritis Rheum 37, 1363 (1994).

Yung et al., "Mechanisms of drug-induced lupus. II. T cells overexpressing lymphocyte function-associated antigen 1 become autoreactive and cause a lupuslike disease in syngeneic mice," J Clin Invest 97, 2866 (1996).

Kaplan et al., Arthritis Rheum 46, S282 (2002).

Lu et al., "DNA methylation and chromatin structure regulate T cell perforin gene expression," J Immunol 170, 51249 (2003)).

Richardson et al., "Evidence for impaired T cell DNA methylation in systemic lupus erythematosus and rheumatoid arthritis.," Arthritis Rheum 33, 1665 (1990).

Richardson et al., Phenotypic and functional similarities between 5-azacytidine-treated T cells and a T cell subset in patients with active systemic lupus erythematosus Arthritis Rheum 35, 647 (1992).

Lu et al., "Demethylation of ITGAL (CD11a) regulatory sequences in systemic lupus erythematosus," Arthritis Rheum 46, 1282 (2002).

Hale et al., "Age-related changes in mature CD4+ T cells: cell cycle analysis," Cell Immunol 220, 51 (2002).

Kobata et al., "CD27-CD70 interactions regulate B-cell activation by T cells," Proc Natl Acad Sci U S A 92, 11249 (1995).

Scheinbart et al., "Procainamide inhibits DNA methyltransferase in a human T cell line," J Rheumatol 18, 530 (1991).

Deng et al., "Hydralazine may induce autoimmunity by inhibiting extracellular signal-regulated kinase pathway signaling," Arthritis Rheum 48, 746 (2003).

Deng et al., "Decreased Ras-mitogen-activated protein kinase signaling may cause DNA hypomethylation in T lymphocytes from lupus patients," Arthritis Rheum 44, 397 (2001).

Fauci et al., Polyclonally triggered B cells in the peripheral blood and bone marrow of normal individuals and in patients with systemic lupus erythematosus and primary Sjogren's syndrome Arthritis Rheum 24, 577 (1981).

Linker-Israeli,et al., "CD8+ lymphocytes from patients with systemic lupus erythematosus sustain, rather than suppress, spontaneous polyclonal IgG production and synergize with CD4+ cells to support autoantibody synthesis," Arthritis Rheum 33, 1216 (1990).

Desai-Mehta et al., "Hyperexpression of CD40 ligand by B and T cells in human lupus and its role in pathogenic autoantibody production," J Clin Invest 97, 2063 (1996).

Oelke et al., "Overexpression of CD70 and overstimulation of IgG synthesis by lupus T cells and T cells treated with DNA methylation inhibitors," Arthritis Rheum 50:1850 (2004).

Lu et al., "Methods for Analyzing the Role of DNA Methylation and Chromatin Structure in Regulating T Lymphocyte Gene Expression," Biol Proced Online 6:189 (2004).

Bombardier et al., "Derivation of the Sledai," Arthritis Rheum 35, 360 (1992).

Tan et al., "The 1982 revised criteria for the classification of systemic lupus erythematosus," Arthritis Rheum 25, 1271 (1982).

Arnett et al., "The American Rheumatism Association 1987 revised criteria for the classification of rheumatoid arthritis," Arthritis Rheum 31, 315-324 (1987).

Richardson et al., "Role of DNA methylation in the regulation of cell function: autoimmunity, aging and cancer," J Nutr. Aug. 2002;132(8 Suppl):2401S-2405S.

Mikovits et al., "Infection with human immunodeficiency virus type 1 upregulates DNA methyltransferase, resulting in de novo methylation of the gamma interferon (IFN-gamma) promoter and subsequent downregulation of IFN-gamma production," Mol Cell Biol. Sep. 1998;18(9):5166-77.

Muegge et al., Epigenetic control during lymphoid development and immune responses aberrant regulation, viruses, and cancer, Ann N Y Acad Sci. Mar. 2003;983:55-70.

Nakajima et al., "Involvement of CD70-CD27 interactions in the induction of experimental autoimmune encephalomyelitis," J Neuroimmunol. Sep. 22, 2000;109(2):188-96.

Morimoto et al., "CD134L engagement enhances human B cell Ig production: CD154/CD40, CD70/CD27, and CD134/CD134L interactions coordinately regulate T cell-dependent B cell responses," J Immunol. Apr. 15, 2000;164(8):4097-104.

Courdec et al., "Enhancement of antitumor immunity by expression of CD70 (CD27 ligand) or CD154 (CD40 ligand) costimulatory molecules in tumor cells," Cancer Gene Ther. May-Jun. 1998;5(3):163-75.

Morimoto et al., "CD134L engagement enhances human B cell Ig production: CD154/CD40, CD70/CD27, and CD134/CD134L interactions coordinately regulate T cell-dependent B cell responses," J Immunol. Apr. 15, 2000;164(8):4097-104.

Jacquot et al., "CD27/CD70 interaction contributes to the activation and the function of human autoreactive CD27+ regulatory T cells," Cell Immunol. Jul. 10, 1997;179(1):48-54.

Januchowski et al., "Role of epigenetic DNA alterations in the pathogenesis of systemic lupus erythematosus," J Appl Genet. 2004;45(2):237-48.

Jacquot et al., CD154/CD40 and CD70/CD27 interactions have different and sequential functions in T cell-dependent B cell responses: enhancement of plasma cell differentiation by CD27 signaling,: J Immunol. Sep. 15, 1997; 159(6):2652-7.

Nakano et al., "Targeted disruption of Traf5 gene causes defects in CD40- and CD27-mediated lymphocyte activation," Proc Natl Acad Sci U S A. Aug. 17, 1999;96(17):9803-8.

Kaplan et al., "Demethylation of promoter regulatory elements contributes to perforin overexpression in CD4+ lupus T cells," J Immunol. Mar. 15, 2004;172(6):3652-61.

\* cited by examiner

A. 1.0 µM 5-Azacytidine

B. 5-Azacytidine

C. 20 μM Procainamide

D. Procainamide

E. 20 µM Hydralazine

F. Hydralazine

G. 25 μM PD98059

H. PD98059

I. 40 μM UO126

J. UO126

C.

D.

E.

F.

A

B

SEQUENCE LISTING

<160> NUMBER OF SEQ ID NOS: 20

<210> SEQ ID NO 1
<211> LENGTH: 36
<212> TYPE: DNA
<213> ORGANISM: Artificial Sequence
<220> FEATURE:
<223> OTHER INFORMATION: Synthetic

<400> SEQUENCE: 1
taggaattcg tataatttaa tttttaataa atgtgt        36

<210> SEQ ID NO 2
<211> LENGTH: 37
<212> TYPE: DNA
<213> ORGANISM: Artificial Sequence
<220> FEATURE:
<223> OTHER INFORMATION: Synthetic

<400> SEQUENCE: 2
aactctagat tatccaactc taatccatac aaaaaaa        37

<210> SEQ ID NO 3
<211> LENGTH: 37
<212> TYPE: DNA
<213> ORGANISM: Artificial Sequence
<220> FEATURE:
<223> OTHER INFORMATION: Synthetic

<400> SEQUENCE: 3
gtggaattcg gaataggaag attgaatgtt ttttgtt        37

<210> SEQ ID NO 4
<211> LENGTH: 35
<212> TYPE: DNA

```
<213> ORGANISM: Artificial Sequence
<220> FEATURE:
<223> OTHER INFORMATION: Synthetic

<400> SEQUENCE: 4
ctatctagaa accaacctac ccctctctaa aaata                                    35

<210> SEQ ID NO 5
<211> LENGTH: 36
<212> TYPE: DNA
<213> ORGANISM: Artificial Sequence
<220> FEATURE:
<223> OTHER INFORMATION: Synthetic

<400> SEQUENCE: 5
ggtgaattct ttaaggttag gagtttaagt ttagtt                                  36

<210> SEQ ID NO 6
<211> LENGTH: 36
<212> TYPE: DNA
<213> ORGANISM: Artificial Sequence
<220> FEATURE:
<223> OTHER INFORMATION: Synthetic

<400> SEQUENCE: 6
caatctagaa ctacacattt attaaaaatt aaatta                                  36

<210> SEQ ID NO 7
<211> LENGTH: 37
<212> TYPE: DNA
<213> ORGANISM: Artificial Sequence
<220> FEATURE:
<223> OTHER INFORMATION: Synthetic

<400> SEQUENCE: 7
gttgaattcg gttaatatgg tgaaatttta tttttat                                 37

<210> SEQ ID NO 8
<211> LENGTH: 37
<212> TYPE: DNA
<213> ORGANISM: Artificial Sequence
<220> FEATURE:
<223> OTHER INFORMATION: Synthetic

<400> SEQUENCE: 8
cactctagat acaacaaaca tccaaaaatt aaaaata                                 37

<210> SEQ ID NO 9
<211> LENGTH: 36
<212> TYPE: DNA
<213> ORGANISM: Artificial Sequence
<220> FEATURE:
<223> OTHER INFORMATION: Synthetic

<400> SEQUENCE: 9
gttgaattcg tgaaaattta tttttattaa aaatat                                  36

<210> SEQ ID NO 10
<211> LENGTH: 36
<212> TYPE: DNA
<213> ORGANISM: Artificial Sequence
<220> FEATURE:
<223> OTHER INFORMATION: Synthetic

<400> SEQUENCE: 10
aattctagaa aaatttcacc atattaacca aactaa                                  36
```

```
<210> SEQ ID NO 11
<211> LENGTH: 37
<212> TYPE: DNA
<213> ORGANISM: Artificial Sequence
<220> FEATURE:
<223> OTHER INFORMATION: Synthetic

<400> SEQUENCE: 11
tgagaattca tttttattaa aaatataaaa agttagt                              37

<210> SEQ ID NO 12
<211> LENGTH: 36
<212> TYPE: DNA
<213> ORGANISM: Artificial Sequence
<220> FEATURE:
<223> OTHER INFORMATION: Synthetic

<400> SEQUENCE: 12
ttatctagac taaacttaaa ctcctaacct taaata                               36

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
tgctttggtc ccattggtcg                                                 20

<210> SEQ ID NO 14
<211> LENGTH: 24
<212> TYPE: DNA
<213> ORGANISM: Artificial Sequence
<220> FEATURE:
<223> OTHER INFORMATION: Synthetic

<400> SEQUENCE: 14
tcctgctgag gtcctgtgtg attc                                            24

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
ggacttcgag caagagatgg                                                 20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
agcactgtgt tggcgtacag                                                 20

<210> SEQ ID NO 17
<211> LENGTH: 27
<212> TYPE: DNA
<213> ORGANISM: Artificial Sequence
<220> FEATURE:
```

```
<223> OTHER INFORMATION: Synthetic

<400> SEQUENCE: 17
gctctcgagg tgaaaaccca tctctac                                              27

<210> SEQ ID NO 18
<211> LENGTH: 27
<212> TYPE: DNA
<213> ORGANISM: Artificial Sequence
<220> FEATURE:
<223> OTHER INFORMATION: Synthetic

<400> SEQUENCE: 18
tccaagcttt ctacttgctt caacctg                                              27

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
cagctcgagc aacatggtga aacc                                                 24

<210> SEQ ID NO 20
<211> LENGTH: 23
<212> TYPE: DNA
<213> ORGANISM: Artificial Sequence
<220> FEATURE:
<223> OTHER INFORMATION: Synthetic

<400> SEQUENCE: 20
attctcgagt gtctgctgta tcc                                                  23
```

METHODS AND KITS FOR DIAGNOSING OR MONITORING AUTOIMMUNE AND CHRONIC INFLAMMATORY DISEASES

This application is a Divisional application of U.S. patent application Ser. No. 11/445,415 filed Jun. 1, 2006, now U.S. Pat. No. 7,439,024, which claims priority to U.S. Provisional Patent Application Ser. No. 60/686,223 filed Jun. 1, 2005, each of which is hereby incorporated by reference in its entirety.

This invention was made with government support under AR042525, AR042753 and AG014783 awarded by the National Institutes of Health. The government has certain rights in the invention.

FIELD OF THE INVENTION

The present invention relates to compositions and methods for diagnosing, monitoring and/or treating an autoimmune or chronic inflammatory disease. In particular, the present invention provides methods for diagnosing, monitoring and treating an autoimmune disease (e.g., rheumatoid arthritis) or chronic inflammatory disease (e.g., systemic lupus erythematosus) based on detecting or altering (e.g., altering expression or methylation status of) autoimmune or chronic inflammatory disease markers (e.g., CD70 and CD40L). The present invention also provides kits for detecting methylation status of autoimmune or chronic inflammatory disease markers (e.g., CD70 and CD40L) and for diagnosing, monitoring and/or treating autoimmune or chronic inflammatory diseases.

BACKGROUND OF THE INVENTION

Autoimmune diseases are generally understood to be diseases where the target of the disease is "self" or "self antigen." Among the many types of autoimmune diseases, there are a number of diseases that are believed to involve T cell immunity directed to self antigens, including, for example, multiple sclerosis (MS), Type I diabetes, and rheumatoid arthritis (RA).

RA is a chronic inflammatory disorder characterized by joint pain. The course of the disease is variable, but can be both debilitating and mutilating. According to conservative estimates approximately 50,000,000 individuals are afflicted with RA worldwide. Those individuals are not only subjected to life-long disability and misery, but as current evidence suggests, their life expectancy is compromised as well.

Systemic lupus erythematosus (SLE) is a chronic inflammatory disease that can affect various parts of the body including skin, blood, kidneys, and joints. SLE may manifest as a mild disease or be serious and life-threatening. More than 16,000 cases of SLE are reported in the United States each year, with up to 1.5 million cases diagnosed. Although SLE can occur at any age, and in either sex, it has been found to occur 10-15 times more frequently in women.

SLE is characterized by the production of auto-antibodies having specificity for a wide range of self-antigens. SLE auto-antibodies mediate organ damage by directly binding to host tissues and by forming immune complexes that deposit in vascular tissues and activate various immune cells. SLE induced damage to the host targets the skin, kidneys, vasculature, joints, various blood elements, and the central nervous system (CNS). The severity of disease, the spectrum of clinical involvement, and the response to therapy vary widely among patients. The clinical heterogeneity of SLE makes it challenging to diagnose, monitor and manage.

When a patient is diagnosed with an autoimmune disease such as RA and SLE, the choice of appropriate therapeutic interventions would be considerably facilitated by diagnostic and prognostic indicators that accurately reflect the current severity of the disease, predict future severity, and monitor response to therapy. Thus, there is a need in the art for reliable diagnostic and prognostic methods to monitor disease activity and response to therapy in patients suffering from autoimmune and chronic inflammatory diseases.

SUMMARY OF THE INVENTION

The present invention relates to compositions and methods for diagnosing, monitoring and/or treating an autoimmune or chronic inflammatory disease. In particular, the present invention provides methods for diagnosing, monitoring and treating an autoimmune disease (e.g., rheumatoid arthritis) or chronic inflammatory disease (e.g., systemic lupus erythematosus) based on detecting or altering (e.g., altering expression or methylation status of) autoimmune or chronic inflammatory disease markers (e.g., CD70 and CD40L). The present invention also provides kits for detecting methylation status of autoimmune or chronic inflammatory disease markers (e.g., CD70 and CD40L) and for diagnosing, monitoring and/or treating autoimmune or chronic inflammatory diseases.

Accordingly, in some embodiments, the present invention provides a method for detecting methylation status of CD70 in a subject, comprising providing a biological sample from the subject, wherein the biological sample comprises CD70 and exposing the sample to reagents for detecting methylation status of CD70. In some embodiments, the reagents detect methylation status of the 5' untranslated region of CD70. In further embodiments, the 5' untranslated region comprises the −338 to −515 (e.g., −466 to −515) region of CD70. In some embodiments, the biological sample is selected from the group comprising a bone marrow sample, a blood sample, a serum sample, a platelet sample, a nucleic acid sample, a DNA sample, a tissue sample, a urine sample, and purified or filtered forms thereof. In some embodiments, the detecting comprises use of a polymerase chain reaction. In other embodiments, the detecting comprises differential antibody binding. In still other embodiments, the detecting comprises restriction enzyme digestion. In yet other embodiments, the detecting comprises use of oligonucleotide binding assays. In some embodiments, the detecting comprises use of a microarray. In other embodiments, the detecting comprises use of bisulfite sequencing.

The present invention also provides a method for detecting methylation status of CD70 in a subject, comprising providing a biological sample from a subject, wherein the biological sample comprises the 5' untranslated CD70 region and detecting methylation status of the −466 to −515 region of the 5' untranslated CD70 region in the biological sample. In some embodiments, the analyzed portion of the 5' untranslated CD70 region is from −338 to −466. The present invention is not limited by the region analyzed. For example, as described below and shown in the figures, numerous additional differentially methylated regions find use with the methods of the present invention.

The present invention additionally provides a method of diagnosing or monitoring an autoimmune or chronic inflammatory disease in a subject, comprising: providing nucleic acid from a subject and detecting the methylation status of CD70 in the nucleic acid. In some embodiments, the method detects the methylation status of the −338 to −515 (e.g., −446 to −515) region of the 5' untranslated CD70 region. In some embodiments, the method further detects the methylation status of perforin. In other embodiments, the method further detects the methylation status of CD11a. In still other embodiments, the method detects the methylation status of IgE FCRγ1. In still other embodiments, the method detects the methylation status of CD30. In still other embodiments, the method detects the methylation status of CD11c. In some embodiments, the methylation status of CD40L is detected. In some embodiments, the method detects the methylation status of two or more of perforin, CD11a, CD30, CD11c, CD40L and IgE FCRγ1. In some embodiments, the chronic inflammatory disease is systemic lupus erythematosis (SLE). In some embodiments, PCR is used for detection. In some embodiments, the present invention provides a method of diagnosing or detecting an autoimmune or chronic inflammatory disease in a subject comprising detecting, individually or in combination, the methylation status of CD70, CD11a, CD30, CD11c, CD40L and IgE FCRγ1.

The present invention additionally provides a method of diagnosing or monitoring an autoimmune or chronic inflammatory disease in a subject, comprising: providing nucleic acid from a subject and detecting the methylation status of CD40L in the nucleic acid. In some embodiments, the method detects the methylation status of the 125 to −400 (e.g., 125 to −110 or the −350 to −400) region of the 5' untranslated CD40L region. In some embodiments, the method further detects the methylation status of perforin. In other embodiments, the method further detects the methylation status of CD11a. In still other embodiments, the method detects the methylation status of IgE FCRγ1. In still other embodiments, the method detects the methylation status of CD30. In still other embodiments, the method detects the methylation status of CD11c. In some embodiments, the methylation status of CD70 is detected. In some embodiments, the method detects the methylation status of two or more of perforin, CD11a, CD30, CD11c, CD70 and IgE FCRγ1. In some embodiments, the chronic inflammatory disease is systemic lupus erythematosis (SLE). In some embodiments, PCR is used for detection. In some embodiments, the autoimmune disease is rheumatoid arthritis.

The present invention further provides a kit comprising reagents for detecting methylation status of CD70 in a subject. In some embodiments, the kit further comprises a positive control that indicates CD70 methylation status. In some embodiments, the kit comprises instructions for using the kit for detecting methylation status of CD70. In some embodiments, the kit further comprises instructions for diagnosing or monitoring an autoimmune or chronic inflammatory disease in the subject based on methylation status of CD70. In further embodiments, the kit instructions comprise instructions required by the U.S. Food and Drug Administration for in vitro diagnostic kits. In some embodiments, the kit comprises instructions for diagnosing or monitoring an autoimmune or chronic inflammatory disease based on methylation status of perforin. In other embodiments, the kit comprises reagents and/or instructions for diagnosing or monitoring an autoimmune or chronic inflammatory disease based on methylation status of CD11a. In still further embodiments, the kit comprises instructions and/or reagents for diagnosing or monitoring an autoimmune or chronic inflammatory disease based on methylation status of IgE FCRγ1. In still further embodiments, the kit comprises instructions and/or reagents for diagnosing or monitoring an autoimmune or chronic inflammatory disease based on methylation status of CD11c and/or CD40L. In still further embodiments, the kit comprises instructions and/or reagents for diagnosing or monitoring an autoimmune or chronic inflammatory disease based on methylation status of CD30. In some embodiments, the kit comprises instructions for diagnosing or monitoring an autoimmune or chronic inflammatory disease based on methylation status of two or more of perforin, CD11a, CD30, CD11c, CD40L and IgE FCRγ1. In some embodiments, PCR is used for detection.

The present invention also provides a kit for detecting gene expression associated with SLE, comprising reagents for detecting methylation status of CD70 and a positive control that indicates test results for CD70 methylation status. In some embodiments, the kit comprises instructions for using the kit for detecting methylation status of CD70. In some embodiments, the kit comprises instructions for diagnosing or monitoring SLE based on methylation status of CD70. In further embodiments, the instructions comprise instructions required by the U.S. Food and Drug Administration for in vitro diagnostic kits. In some embodiments, the kit comprises instructions and/or reagents for diagnosing or monitoring SLE based on methylation status of perforin. In other embodiments, the kit comprises instructions and/or reagents for diagnosing or monitoring SLE based on methylation status of CD11a. In still other embodiments, the kit comprises instructions and/or reagent for diagnosing or monitoring SLE based on methylation status of IgE FCRγ1. In still other embodiments, the kit comprises instructions and/or reagent for diagnosing or monitoring SLE based on methylation status of CD30. In still other embodiments, the kit comprises instructions and/or reagent for diagnosing or monitoring SLE based on methylation status of CD11c. In some embodiments, the kit comprises instructions for diagnosing or monitoring SLE based on methylation status of two or more of perforin, CD11a, CD30, CD11c, CD40L and IgE FCRγ1.

DEFINITIONS

Figure 1:
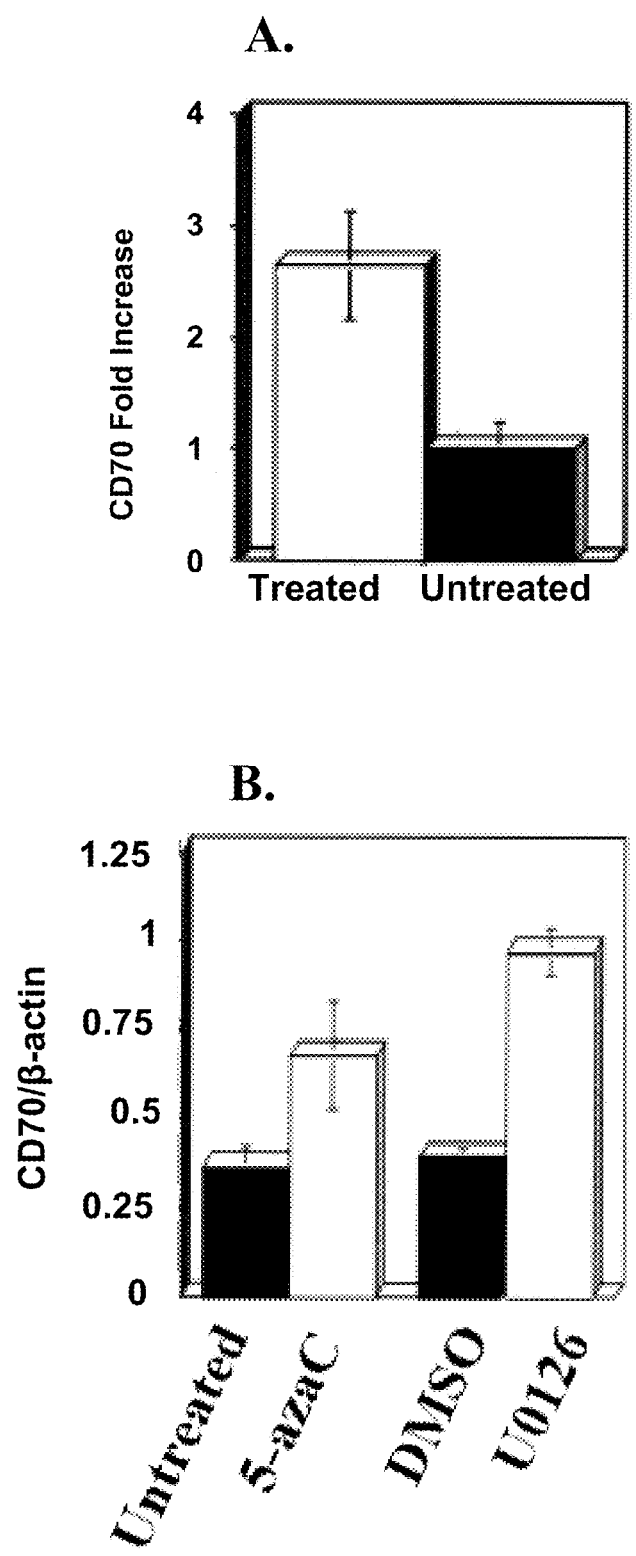
FIG. 1 shows the effect of DNA methylation inhibition on CD70 expression.

As used herein, the term "autoimmune disease" refers generally to diseases which are characterized as having a component of self-recognition. Examples of autoimmune diseases include, but are not limited to, Autoimmune hepatitis, Multiple Sclerosis, Systemic Lupus Erythematosus, Myasthenia Gravis, Type I diabetes, Rheumatoid Arthritis, Psoriasis, Hashimoto's Thyroiditis, Grave's disease, Ankylosing Spondylitis Sjogrens Disease, CREST syndrome, Scleroderma and many more. Most autoimmune diseases are also chronic inflammatory diseases. This is defined as a disease process associated with long-term (>6 months) activation of inflammatory cells (leukocytes). The chronic inflammation leads to damage of patient organs or tissues. Many diseases are chronic inflammatory disorders, but are not know to have an autoimmune basis. For example, Atherosclerosis, Congestive Heart Failure, Crohn's disease, Ulcerative Colitis, Polyarteritis nodosa, Whipple's Disease, Primary Sclerosing Cholangitis and many more.

The clinical manifestations of these diseases range from mild to severe. Mild disease encompasses symptoms that may be function-altering and/or comfort-altering, but are neither immediately organ-threatening nor life-threatening. Severe disease entails organ-threatening and/or life-threatening symptoms. For example, severe autoimmune disease is often associated with clinical manifestations such as nephritis, vasculitis, central nervous system disease, premature atherosclerosis or lung disease, or combinations thereof, that require aggressive treatment and may be associated with premature death. Anti-phospholipid antibody syndrome is often associated with arterial or venous thrombosis. Any statistically significant correlation that is found to exist between autoimmune or chronic inflammatory disease markers (e.g., CD70 or CD40L) methylation and any clinical parameters of an autoimmune or inflammatory disease enables the use of an autoimmune or chronic inflammatory disease marker (e.g., CD70 or CD40L) methylation assay as part of a diagnostic battery for that disease or group of diseases.

Diseases can exhibit ranges of activities. As used herein, disease activity (e.g., "active lupus") refers to whether the pathological manifestations of the disease are fulminant, quiescent, or in a state between these two extremes. For example, a patient suffering from SLE having active disease could be diagnosed or monitored through detecting a hypomethylated form of an autoimmune or chronic inflammatory disease marker (e.g., CD70 or CD40L) described in the present invention, whereas a patient having inactive disease would manifest comparatively higher or normal levels of autoimmune or chronic inflammatory disease markers (e.g., CD70 or CD40L) methylation.

The term "epitope" as used herein refers to that portion of an antigen that makes contact with a particular antibody.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having autoimmune or chronic inflammatory disease" refers to a subject that presents one or more symptoms indicative of an autoimmune or chronic inflammatory disease (e.g., hives or joint pain) or is being screened for an autoimmune or chronic inflammatory disease (e.g., during a routine physical). A subject suspected of having an autoimmune or chronic inflammatory disease may also have one or more risk factors. A subject suspected of having an autoimmune or chronic inflammatory disease has generally not been tested for autoimmune or chronic inflammatory disease. However, a "subject suspected of having autoimmune or chronic inflammatory disease" encompasses an individual who has received an initial diagnosis but for whom the severity of the autoimmune or chronic inflammatory disease is not known. The term further includes people who once had autoimmune or chronic inflammatory disease but whose symptoms have ameliorated.

As used herein, the term "subject at risk for autoimmune or chronic inflammatory disease" refers to a subject with one or more risk factors for developing an autoimmune or chronic inflammatory disease. Risk factors include, but are not limited to, gender, age, genetic predisposition, environmental expose, previous incidents of autoimmune or chronic inflammatory disease, preexisting non-autoimmune or chronic inflammatory diseases, and lifestyle.

As used herein, the term "characterizing autoimmune or chronic inflammatory disease in subject" refers to the identification of one or more properties of a sample in a subject, including but not limited to, the presence of calcified tissue and the subject's prognosis. Autoimmune or chronic inflammatory disease may be characterized by the identification of the expression of one or more autoimmune or chronic inflammatory disease marker genes, including but not limited to, the autoimmune or chronic inflammatory disease markers disclosed herein.

As used herein, the term "autoimmune or chronic inflammatory disease marker genes" refers to a gene whose expression level and/or whose methylation status, or other characteristic, alone or in combination with other genes, is correlated with autoimmune or chronic inflammatory disease or prognosis of autoimmune or chronic inflammatory disease. The correlation may relate to either an increased or decreased expression, or an increased or decreased methylation, of the gene. For example, the expression or low levels of methylation (e.g., as compared to normal, healthy controls) of the gene may be indicative of autoimmune or chronic inflammatory disease, or lack of expression or high levels of methylation (e.g., as compared to normal, healthy controls) of the gene may be correlated with poor prognosis in an autoimmune or chronic inflammatory disease patient. Autoimmune or chronic inflammatory disease marker expression and methylation status may be characterized using any suitable method, including but not limited to, those described in illustrative Examples 1-14 below.

As used herein, the term "a reagent that specifically detects expression levels" refers to reagents used to detect the expression of one or more genes and the term "a reagent that specifically detects methylation status" refers to reagents used to detect the methylation status of one or more genes (e.g., including but not limited to, the autoimmune and chronic inflammatory disease markers of the present invention). Examples of suitable reagents include but are not limited to, nucleic acid probes capable of specifically hybridizing to the gene of interest, PCR primers capable of specifically amplifying the gene of interest, PCR primers that function in the context of a methylation sensitive PCR reaction, and antibodies capable of specifically binding to proteins expressed by the gene of interest. Other non-limiting examples can be found in the description and examples below.

As used herein, the term "detecting a decreased or increased expression relative to non-autoimmune or chronic inflammatory disease control" refers to measuring the level of expression of a gene (e.g., the level of mRNA or protein) relative to the level in a non-autoimmune or chronic inflammatory disease control sample. Gene expression can be measured using any suitable method, including but not limited to, those described herein.

As used herein, the term "detecting a change in gene expression (e.g., of CD70, IgE FCRγ1, CD30, CD40L or CD11c) in said autoimmune or chronic inflammatory disease sample in the presence of said test compound relative to the absence of said test compound" refers to measuring an altered level of expression (e.g., increased or decreased) in the presence of a test compound relative to the absence of the test compound. Gene expression can be measured using any suitable method, including but not limited to, those described in Examples 1-14 below.

As used herein, the term "instructions for using said kit for detecting autoimmune or chronic inflammatory disease in said subject" includes instructions for using the reagents contained in the kit for the detection and characterization of autoimmune or chronic inflammatory disease in a sample from a subject. In some embodiments, the instructions further comprise the statement of intended use required by the U.S. Food and Drug Administration (FDA) in labeling in vitro diagnostic products.

As used herein, the term "autoimmune or chronic inflammatory disease expression profile map" refers to a presentation of expression levels of genes in a particular type of autoimmune or chronic inflammatory disease. The map may be presented as a graphical representation (e.g., on paper or on a computer screen), a physical representation (e.g., a gel or array) or a digital representation stored in computer memory. In preferred embodiments, maps are generated from pooled samples comprising samples from a plurality of patients with the same type of autoimmune or chronic inflammatory disease.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "providing a prognosis" refers to providing information regarding the impact of the presence of autoimmune or chronic inflammatory disease (e.g., as determined by the diagnostic methods of the present invention) on a subject's future health (e.g., expected morbidity or mortality).

As used herein, the term "subject diagnosed with an autoimmune or chronic inflammatory disease" refers to a subject who has been tested and found to have autoimmune or chronic inflammatory disease. The autoimmune or chronic inflammatory disease may be diagnosed using any suitable method, including but not limited to, biopsy, x-ray, blood test, and the diagnostic methods of the present invention.

As used herein, the term "initial diagnosis" refers to results of initial autoimmune or chronic inflammatory disease diagnosis (e.g. the presence or absence of autoimmune or chronic inflammatory disease). An initial diagnosis does not include information about the severity of the autoimmune or chronic inflammatory disease.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (mRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics, e.g., hypomethylation) when compared to the wild-type gene or gene product. It is noted that naturally occurring mutants can be isolated; these are identified by the fact that they have altered characteristics (including altered nucleic acid sequences) when compared to the wild-type gene or gene product.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the term "methylation status" refers to the presence or absence of methylation within a gene, specifically, to the presence or absence of methylation of deoxycytosine (dC) bases in CG pairs within a gene, the presence of which serves as one of the mechanisms by which gene expression is suppressed (See, e.g., Attwood et al., Cell Mol Life Sci 59, 241 (2002)).

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization (1985)). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent (50×Denhardt's contains per 500 ml: 5 g Ficoll (Type 400, Pharamcia), 5 g BSA (Fraction V; Sigma)) and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA 69:3038 (1972)). Other nucleic acids will not be replicated by this amplification enzyme. Similarly, in the case of T7 RNA polymerase, this amplification enzyme has a stringent specificity for its own promoters (Chamberlin et al., Nature 228:227 (1970)). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 (1989)). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press (1989)).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target." In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31-9.58 (1989)).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 (1989)).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 (1973)), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk⁻ cell lines, the CAD gene that is used in conjunction with CAD-deficient cells and the mammalian hypoxanthine-guanine phosphoribosyl (hprt) gene that is used in conjunction with hprt⁻ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., autoimmune and chronic inflammatory disease). Test compounds comprise both known and potential therapeutic compounds. A test compound can be determined to be therapeutic by screening using the screening methods of the present invention. In some embodiments of the present invention, test compounds include antisense compounds.

As used herein, the term "sample" is used in its broadest sense. In one sense, it is meant to include a specimen or culture obtained from any source, as well as biological and environmental samples. Biological samples may be obtained from animals (including humans) and refers to a biological material or compositions found therein, including, but not limited to, bone marrow, blood, serum, platelet, plasma, interstitial fluid, urine, cerebrospinal fluid, nucleic acid, DNA, tissue, and purified or filtered forms thereof. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention relates to compositions and methods for diagnosing, monitoring and/or treating an autoimmune or chronic inflammatory disease. In particular, the present invention provides methods for diagnosing, monitoring and treating an autoimmune disease (e.g., rheumatoid arthritis) or chronic inflammatory disease (e.g., systemic lupus erythematosus) based on detecting or altering (e.g., altering expression or methylation status of) autoimmune or chronic inflammatory disease markers (e.g., CD70 and CD40L). The present invention also provides kits for detecting methylation status of autoimmune or chronic inflammatory disease markers (e.g., CD70 and CD40L) and for diagnosing, monitoring and/or treating autoimmune or chronic inflammatory diseases.

I. Markers for Autoimmune or Chronic Inflammatory Disease

A. Identification of Markers

The present invention provides markers whose expression is specifically altered in autoimmune or chronic inflammatory disease. Such markers find use in the diagnosis and characterization of autoimmune or chronic inflammatory disease.

Experiments conducted during the development of the present invention resulted in the identification of genes whose expression level was altered (e.g., increased or decreased) in autoimmune and/or chronic inflammatory disease. In particular, experiments conducted during the development of the present invention identified methylation patterns associated with particular genomic sequences that correlate certain classes of diseases. In particular, the present invention provides compositions, kits, and methods for detecting the methylation status of one or more of CD70, IgE FCRγ1, CD11a, CD30, CD40L, and CD11c for diagnostic, drug screening, research, and therapeutic applications.

As reported herein, CD4+ T cell DNA hypomethylation contributes to the development of drug-induced and idiopathic systemic lupus erythematosus (SLE) and rheumatoid arthritis (RA). As used herein, the term "DNA methylation" refers to the methylation of deoxycytosine (dC) bases in CG pairs, and it is one of the mechanisms by which gene expression is suppressed (See, e.g., Attwood et al., Cell Mol Life Sci 59, 241 (2002)). CD4+ T cells treated in vitro with the DNA methylation inhibitors 5-azacytidine (5-azaC), procainamide, or hydralazine become autoreactive, killing autologous or syngeneic macrophages and promoting antibody production (See, e.g., Cornacchia et al., J Immunol 140, 2197 (1988); Richardson et al., Clin Immunol Immunopathol 55, 368 (1990); Quddus et al., J Clin Invest 92, 38 (1993); Yung et al., Arthritis Rheum 40, 1436 (1997)). Adoptive transfer of the autoreactive cells causes a lupus-like disease (See, e.g., Quddus et al., J Clin Invest 92, 38 (1993); Yung et al., Arthritis Rheum 40, 1436 (1997)). The autoreactivity is in part due to an overexpression of the adhesion molecule lymphocyte function-associated antigen 1 (LFA-1; CD11a/CD18) (See, e.g., Richardson et al., Arthritis Rheum 37, 1363 (1994); Yung et al., J Clin Invest 97, 2866 (1996)), and abnormal perforin expression contributes to the macrophage killing (See, e.g., Kaplan et al., Arthritis Rheum 46, S282 (2002); Lu et al., J Immunol 170, 51249 (2003)).

Genomic deoxymethylcytosine (dmC) content is decreased in T cells from patients with active SLE, similar to that in T cells treated with 5-azaC, procainamide, and hydralazine (See, e.g., Richardson et al., Arthritis Rheum 33, 1665 (1990)). Overexpression of LFA-1 is observed on a CD4+, perforin expressing, cytotoxic, autoreactive lupus T cell subset with major histocompatibility complex specificity identical to that of T cells treated with DNA methylation inhibitors (See, e.g., Kaplan et al., Arthritis Rheum 46, S282 (2002); Richardson et al., Arthritis Rheum 35, 647 (1992)). Furthermore, the same LFA-1 and perforin regulatory sequences are demethylated in CD4+ T cells from patients with active SLE, similar to results observed in T cells treated with 5-azaC or procainamide (See, e.g., Kaplan et al., Arthritis Rheum 46, S282 (2002); Lu et al., Arthritis Rheum 46, 1282 (2002)). Together, these studies show that T cell DNA hypomethylation is important to the pathogenesis of autoimmunity in animal models and in humans with drug-induced and idiopathic lupus.

Novel findings reported herein demonstrate methylation-sensitive genes through treating phytohemagglutinin (PHA)—stimulated human T lymphocytes with 5-azaC, and the subsequent analysis of gene expression using oligonucleotide arrays. For example, a gene that reproducibly increased expression >2-fold is CD70, also known as CD27 ligand (CD27L) (See Example 2, FIGS. 1A and B). Also increased were perforin, CD11a, CD11c, CD30, IgE FCRγ1, CD40L, among others.

CD70 is a member of the tumor necrosis factor (TNF) family that is expressed on activated CD4+ and CD8+ T cells and B cells (See e.g., Lens et al., Semin Immunol 10, 491 (1998)). Adding cells transfected with CD70 increases pokeweed mitogen (PWM)—stimulated IgG synthesis in T cell-dependent B cell assays, indicating that CD70 has B cell-costimulatory functions resembling those of CD40L (See, e.g., Kobata et al., Proc Natl Acad Sci USA 92, 11249 (1995)). This shows that T cells overexpressing CD70 as a result of either DNA methylation inhibitor treatment or the DNA hypomethylation associated with lupus provide additional B cell-costimulatory signals.

CD70 expression is increased on T cells treated with a panel of DNA methylation inhibitors (See Example 3, FIGS. 2A-J). The DNA methylation inhibitors used included the direct DNA methyltransferase inhibitors 5-azaC and procainamide (See, e.g., Scheinbart et al., J Rheumatol 18, 530 (1991)), as well as PD98059, U0126, and hydralazine, which decrease DNA methyltransferase expression by inhibiting ERK pathway signaling (See, e.g., Deng et al., Arthritis Rheum 48, 746 (2003)). While an understanding of the mechanism is not necessary to practice the present invention and the present invention is not limited to any particular mechanism of action, it is likely that ERK pathway inhibition is more relevant to idiopathic SLE in humans than is direct DNA methyltransferase inhibition, because T cells from patients with active lupus have impaired ERK pathway signaling, associated with decreased DNA methyltransferase levels and hypomethylated DNA (See, e.g., Deng et al., Arthritis Rheum 44, 397 (2001)).

Figure 3:
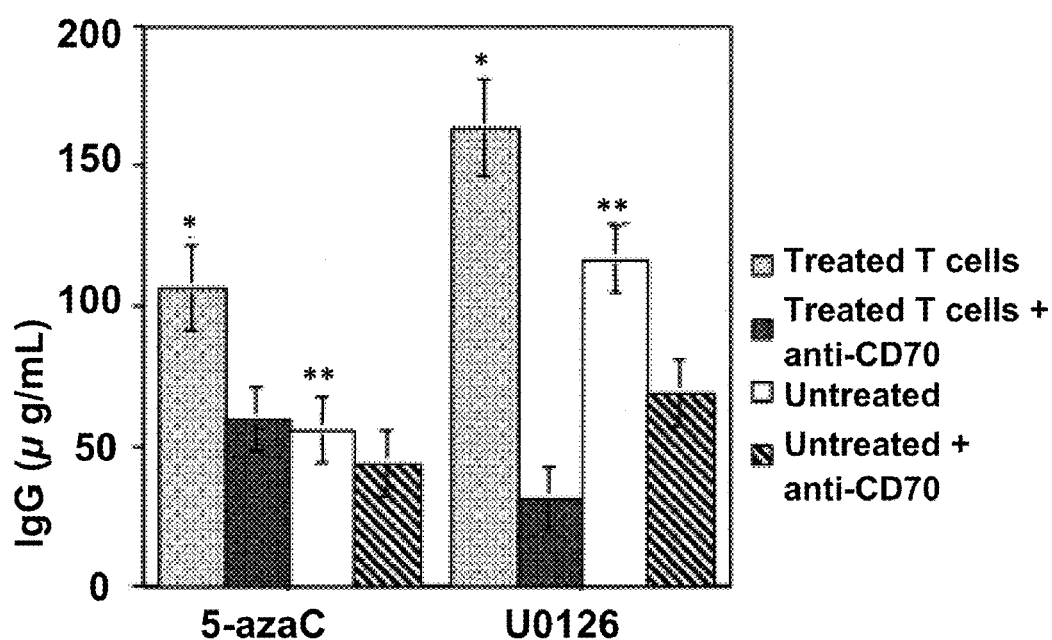
FIG. 3 shows increased B cell costimulation by polyclonal T cells treated with DNA methylation inhibitors, and reversal with anti-CD70.
Figure 4:
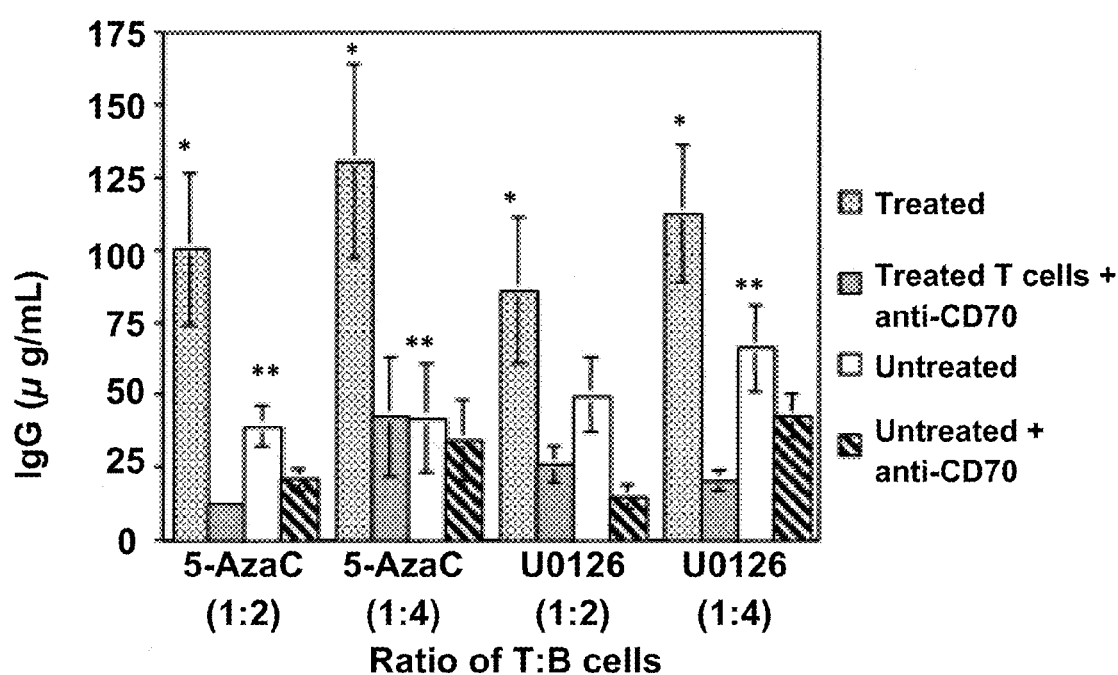
FIG. 4 shows increased B cell costimulation by cloned T cells treated with DNA methylation inhibitors, and reversal with anti-CD70.

Hypomethylated T cells overexpressing CD70 overstimulate the production of IgG by B cells (See Example 4, FIGS. 3 and 4). Initial studies compared untreated polyclonal T cells with the same cells treated with a DNA methyltransferase inhibitor and a MEK inhibitor. The drug-treated cells enhanced PWM induced IgG secretion, and the effect was reversed with anti-CD70, indicating that T cell CD70 overexpression contributes to the increase in IgG synthesis (See Example 4, FIG. 3). The possibility that the effects might have been indirect due to effects of the drugs on a T cell subset lacking CD70, but requiring CD70+ cells, is unlikely because cloned T cells (tetanus toxoid-reactive human CD4+ T cell line—TT48E) gave similar results (See Example 4, FIG. 4).

The possibility that anti-CD70 delivered a suppressive signal through B cell CD70 was tested by pretreating the T cell clones with anti-CD70 before adding them to the B cells, thereby resulting in suppressing the IgG response (See Example 4, FIG. 4). Controls using LPS and purified B cells indicate that anti-CD70 does not have a direct suppressive effect on B cells (See Example 4, FIG. 3). Similar results were obtained with the cloned CD4+ T cell line (See Example 4, FIG. 4). These results, show that CD70 on T cells contributes to increased B cell IgG production.

Figure 5:
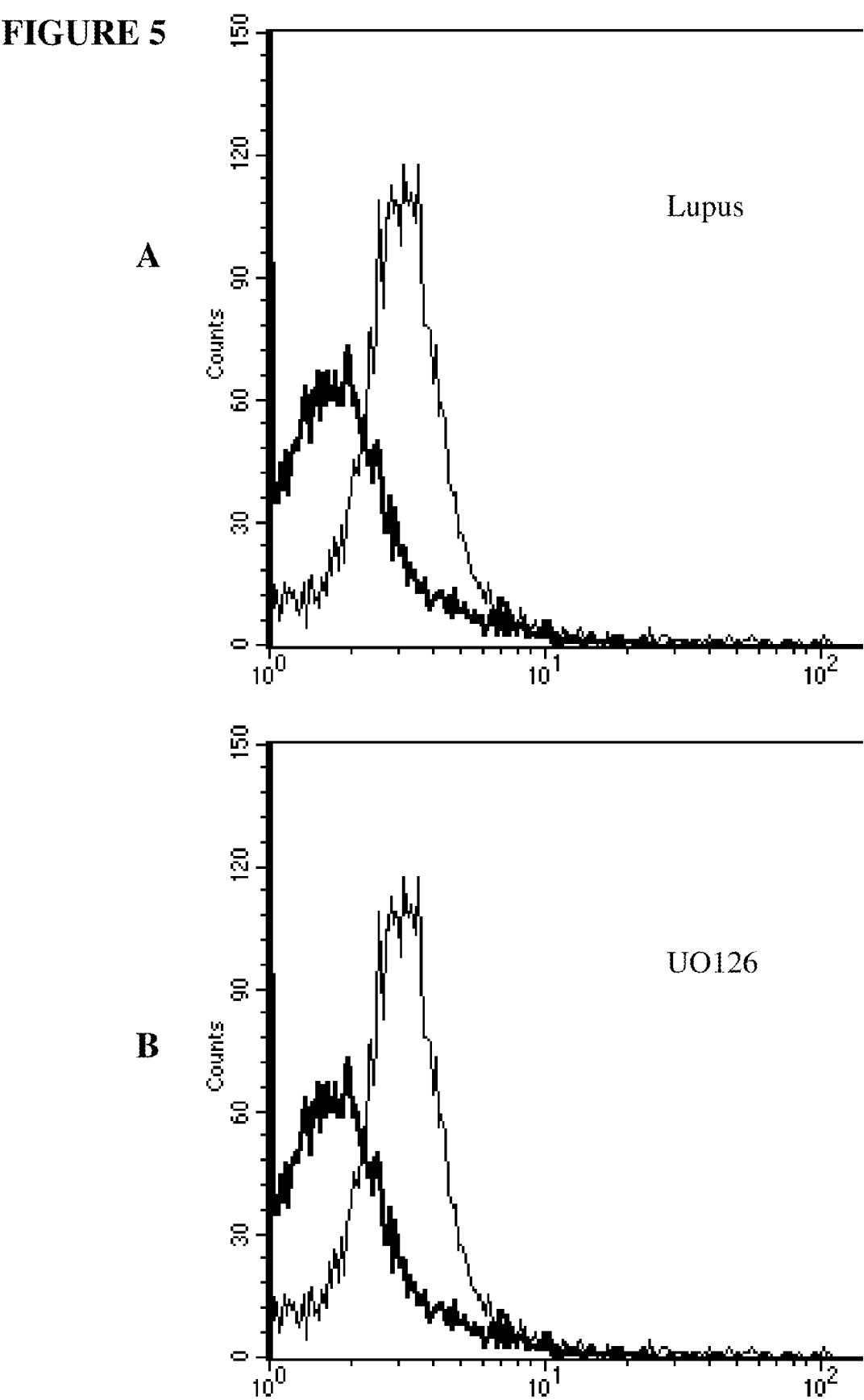
FIG. 5 shows overexpression of CD70 on T cells from patients with systemic lupus erythematosus (SLE).
Figure 5:
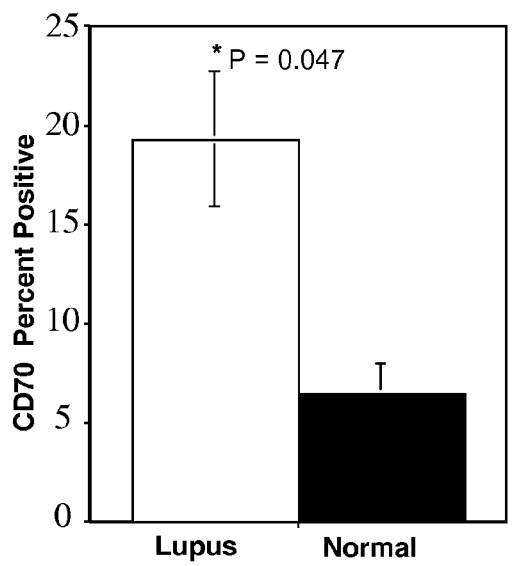
Figure 5:
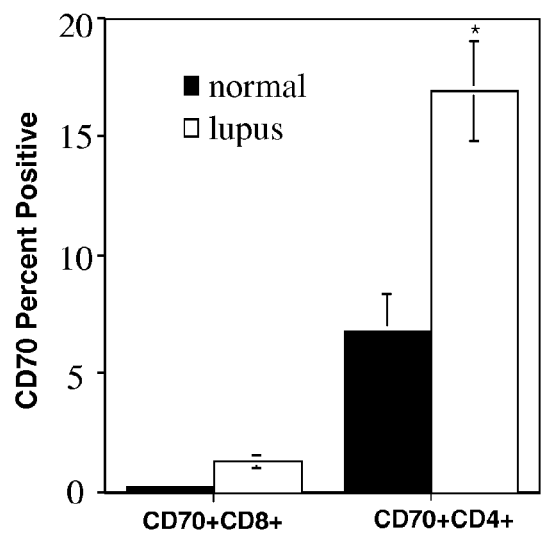
Figure 5:
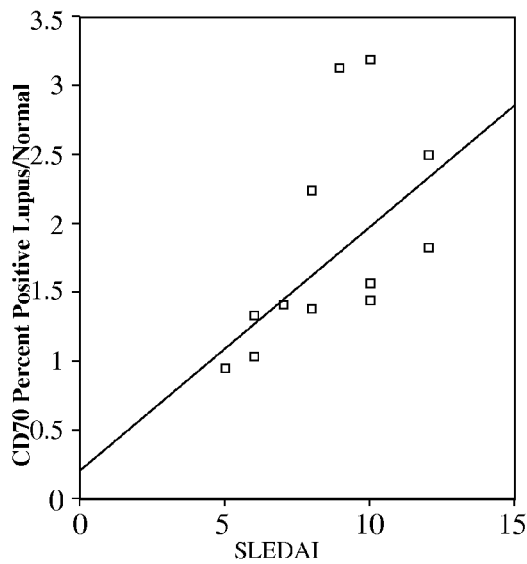
Figure 5:
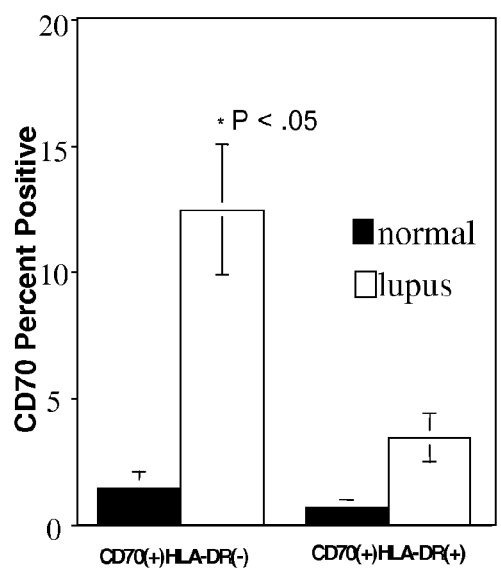

Similar studies were performed on T cells from SLE patients. Flow cytometry studies examining CD70 expression on T cells from patients with active lupus and age-, race-, and sex-matched normal controls demonstrated that CD70 was overexpressed on CD4+ T cells from the lupus patients and that the degree of overexpression was directly proportional to disease activity (See Example 5, FIG. 5). This is similar to the expression of CD11a and perforin, two other methylation-sensitive genes, and reflects DNA hypomethylation that characterizes T cells from patients with active disease (See e.g., Lu et al., Arthritis Rheum 46, 1282 (2002); Kaplan et al., J Immunol 172, 3652 (2004), herein incorporated by reference in their entireties; and Example 7). Again, the observation that T cells treated with DNA methylation inhibitors caused a lupus-like disease shows that DNA hypomethylation induces the autoimmune disease, rather than just reflecting an effect secondary to the disease process.

Figure 6:
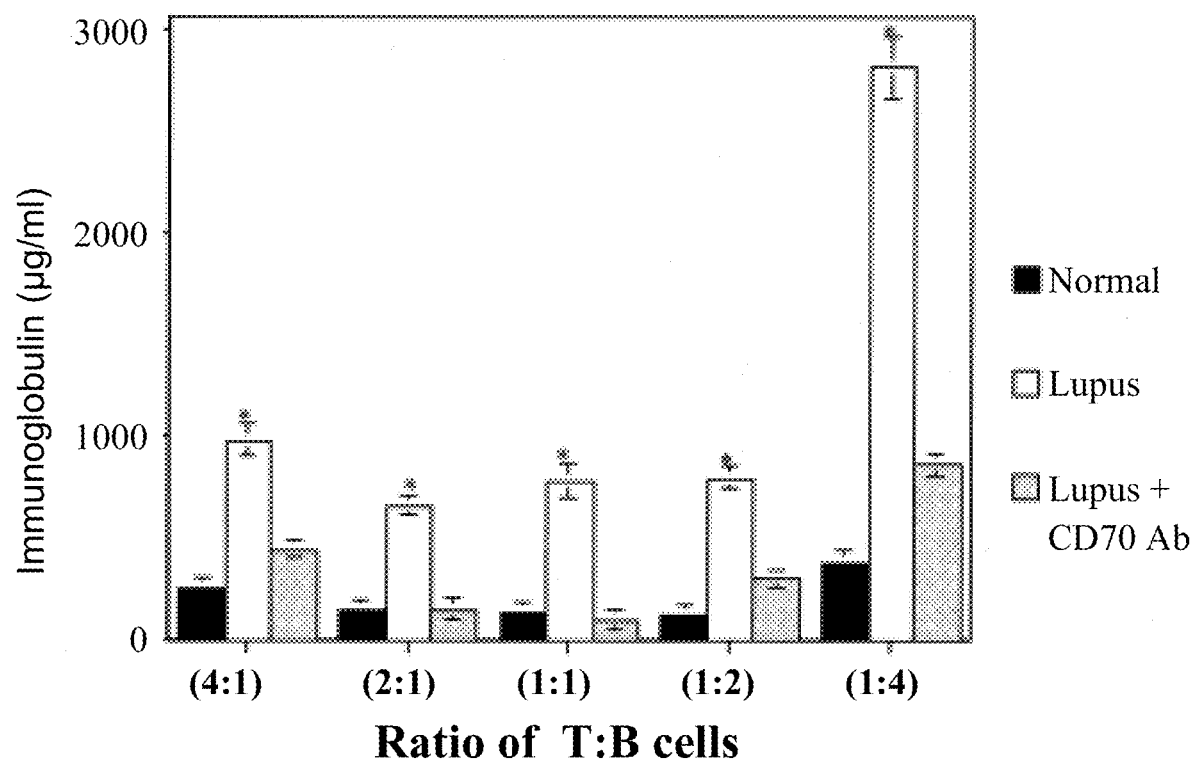
FIG. 6 shows anti-CD70 inhibition of IgG synthesis induced by lupus T cells.

B cells in the peripheral blood of patients with active lupus are abnormally activated and secrete polyclonal IgG (See Example 6, FIG. 6). While some of the antibodies secreted are the autoantibodies usually associated with SLE, other B cells secrete antibodies to antigens present on sheep erythrocytes and even keyhole limpet hemocyanin (See e.g., Fauci et al., Arthritis Rheum 24, 577 (1981)), suggesting that there is nonspecific polyclonal activation. T cells from patients with active lupus stimulated IgG synthesis by autologous B cells in the absence of added antigen or mitogen (Example 6, FIG. 6), similar to data reported by others (See e.g., Linker-Israeli, et al., Arthritis Rheum 33, 1216 (1990)). Pretreatment of the T cells with anti-CD70 abrogated this response. These studies show that T cell CD70 is important for the abnormal B cell stimulation in lupus. The present studies also show that CD70 overexpression on lupus T cells contributes to B cell stimulation, together with other molecules, such as CD40L (See, e.g., Desai-Mehta et al., J Clin Invest 97, 2063 (1996)), and that inhibiting any of these molecules is sufficient to decrease the antibody response to normal levels.

Demethylation of promoter regulatory elements within the CD70 promoter contributes to CD70 overexpression in CD4+ lupus T cells. DNA was isolated from the CD4+ T cells of 7 healthy individuals, bisulfite treated, and 1000 bp 5' to the putative CD70 transcription start site was amplified by PCR. For each individual, 5 fragments were cloned and sequenced. Each dot on the X axis represents a potentially methylatable CG pair, and the Y axis represents the average methylation of the 35 determinations for each point (See Example 7, FIG. 7). The horizontal bar identifies a region containing 6 CG pairs that is demethylated by methylation inhibitors and in lupus (See Example 7, FIG. 7).

Regulatory elements in the CD70 promoter are hypomethylated in individuals with active lupus. Bisulfite sequencing implicated 6 CG pairs found within the CD70 promoter in a region −338 to −515 (e.g., −446 to −515) of the transcriptional start site that were hypomethylated in lupus patients compared with healthy controls. The average methylation status of the 6 CG pairs for healthy versus lupus individuals is shown (See Example 7, FIG. 8, N and Lupus, respectively).

Figure 8:
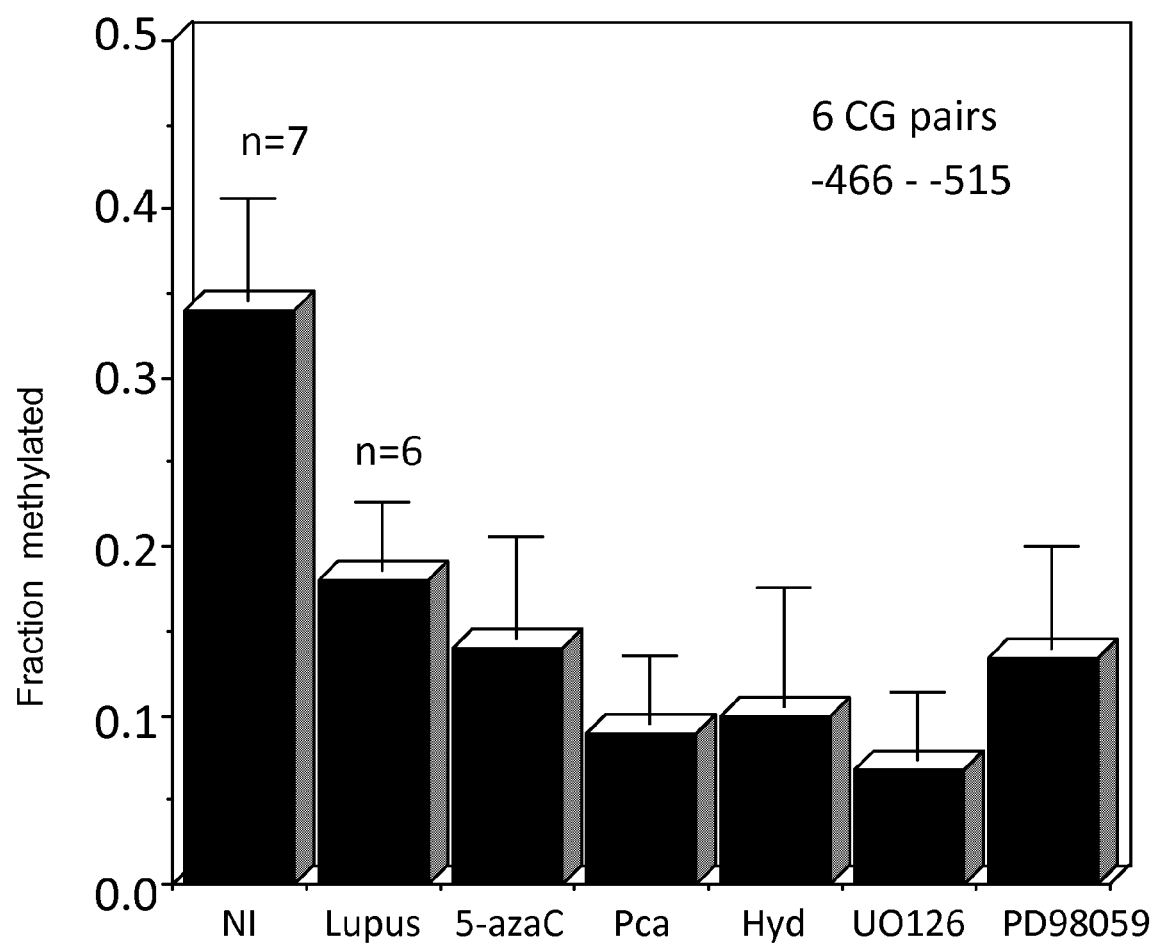
FIG. 8 shows the effect of lupus and DNA methylation inhibitors on a regulatory element in the CD70 promoter.

CD4+ T cells from 5 individuals were also stimulated with PHA, treated with the irreversible DNA methyltransferase inhibitor 5-azacytidine (5-azaC), and the methylation status of the 6 CG pairs similarly analyzed from the 25 fragments sequenced (See Example 7, FIG. 8, 5-azaC). PHA stimulation has no effect on the methylation status of this region. Similar patterns of promoter hypomethylation were observed in stimulated T cells treated with the MEK inhibitor PD98059 (3 donors, 15 fragments), the competitive DNA methyltransferase inhibitor procainamide (Pca, 4 donors, 20 fragments), the ERK pathway inhibitor hydralazine (Hyd, 3 donors, 15 fragments), or the MEK inhibitor U0126 (2 donors, 10 fragments) (See Example 7, FIG. 8, Pca, Hyd, U0126 and PD85059, respectively). Hence, lupus T cells, T cells treated with the lupus inducing drugs Pca and Hyd, and T cells treated with either DNA methyltransferase inhibitors or ERK pathway inhibitors, all demethylate this region of the CD70 promoter (See Example 7, FIG. 8).

Thus, the present invention identified methods for diagnosing and monitoring individuals with autoimmune or chronic inflammatory diseases (e.g., SLE or RA) resulting from hypomethylation of the CD70 or CD40L promoters or overexpression of CD70 or CD40L on CD4+ T cells. Hence, the present invention provides methods for diagnosing or monitoring autoimmune diseases (e.g., systemic lupus erythematosus (SLE)) based on detecting methylation status of CD70 and/or CD40L. The present invention also provides kits for detecting methylation status of CD70, perforin, CD11a, CD11c, CD30, IgE FCRγ1, and CD40L individually, or kits for determining the methylation of a combination of two or more of CD70, perforin, CD11a, CD11c, CD30, IgE FCRγ1, CD40L, and for diagnosing or monitoring autoimmune or chronic inflammatory diseases. These methods and kits find use as diagnostics, in drug screening, in research applications, and in monitoring therapies.

Accordingly, in some embodiments, the present invention provides a method for detecting methylation status of CD70, perforin, CD11a, CD11c, CD30, IgE FCRγ1, and/or CD40L in a subject, comprising providing a biological sample from the subject, wherein the biological sample comprises CD70, perforin, CD11a, CD11c, CD30, IgE FCRγ1, and/or CD40L and exposing the sample to reagents for detecting methylation status of CD70, perforin, CD11a, CD11c, CD30, IgE FCRγ1, and/or CD40L alone or in combination with other lupus markers (e.g., perforin, CD11a, CD11c, CD30, IgE FCRγ1, CD40L, etc.). The present invention also provides methods employing IgE FCRγ1, CD 11c, CD40L, or CD30 alone or in combination with other markers for characterizing autoimmune of chronic inflammatory diseases.

The present invention also provides a method of diagnosing or monitoring an autoimmune or chronic inflammatory disease in a subject, comprising: providing nucleic acid from a subject and detecting the methylation status of CD70, alone or in combination with other markers of autoimmune or chronic inflammatory disease (e.g., perforin, CD11a, CD30, CD11c, IgE FCRγ1, CD40L, etc.). The present invention also provides methods employing IgE FCRγ1, CD11c, CD40L, or CD30 alone or in combination with other markers.

Several methods are contemplated to be useful in the present invention to determine methylation status of genes (e.g., CD70 or CD40L). One method is based on the inability of methylation-sensitive restriction enzymes (MSRE) to cleave sequences that contain one or more methylated CpGs, followed by Southern Blot (SB) hybridization with probes identifying fragments after digestion (See, e.g., Ng et al., Blood 89, 2500 (1997); Gonzalez et al., Leukemia 14, 183 (2000)). Another method uses the same background (MSRE)

but followed by a PCR (See, e.g., Tasaka et al., Br J Haematol 101, 558 (1998); Gonzalez et al., Leukemia 14, 183 (2000)). Gene sequencing has also been used to find methylated cytosines. In a preferred embodiment, methylation-specific PCR (MSP), based on the modification of cytosine to uracil by bisulfite treatment, is used (See e.g., Herman et al., Proc Natl Acad Sci USA 93, 9821 (1996); Clark et al., Nuc Acids Res 22, 2990 (1994)). In a particularly preferred embodiment, fluorogenic probes are used with MSP (See, e.g., Cottrell and Laird, Ann N Y Acad. Sci. 983, 120 (2003)). In some embodiments, detecting comprises use of methylation sensitive PCR (See, e.g., Matsuyama et al., Nucleic Acids Research, Vol. 31, 4490-4496 (2003)). In some embodiments, detecting comprises use of oligonucleotide binding assays. In other embodiments, the detecting comprises use of a microarray. In one microarray method, the use of colorimetric silver using DNA microarrays coupled with linker-PCR is used for detection of methylation (See, e.g., Ji et al., Clin Chim Acta. 342, 145 (2004)). It is not intended that the present invention be limited to any of these particular methods of detecting gene methylation status. Indeed, any method useful for detecting gene methylation status is contemplated to be useful in the present invention.

The present invention provides a kit comprising reagents for detecting methylation status of one or more of CD70 perforin, CD11a, CD11c, CD30, IgE FCRγ1, and CD40L in a subject. The present invention also provides kits for detecting methylation status of CD70, IgE FCRγ1, CD30, CD40L or CD11c alone or in combination with other markers.

The present invention also provides a kit for detecting gene expression associated with autoimmune or chronic inflammatory disease (e.g., SLE), comprising reagents for detecting methylation status of CD70 and/or CD40L and a positive control that indicates test results for CD70 and/or CD40L methylation status.

Figure 10:
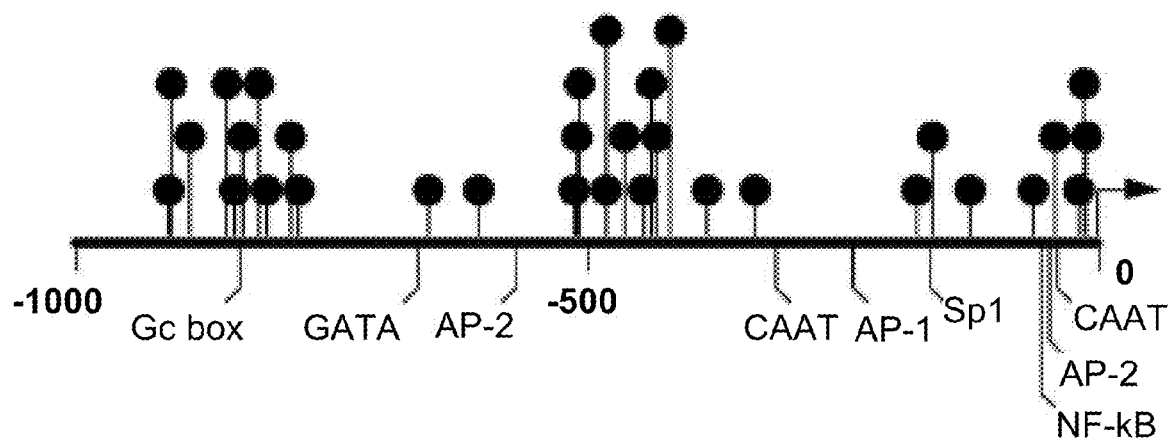
FIG. 10. shows the CD70 (TNFSF7) promoter and 5' flanking region sequence and relevant features. The filled circles represent the potentially methylatable CG pairs, and the broken arrow the putative transcription start site. The locations of potential transcription factor binding sites and CAAT boxes are also shown.
Figure 11:
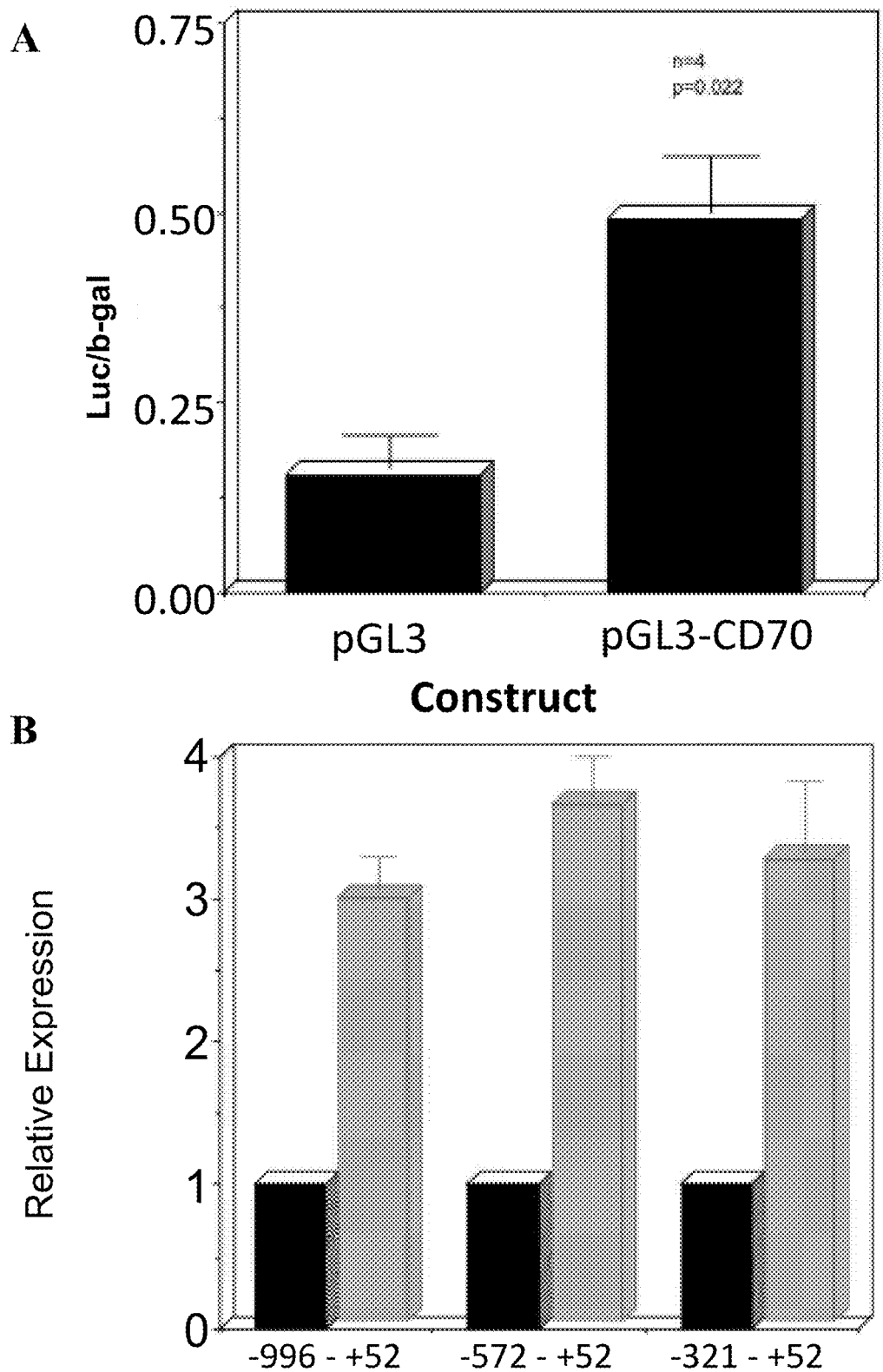
FIG. 11. shows CD70 promoter activity. (A) Shows activity of a 1018 bp fragment (−996 to +52) cloned into pGL3-Basic while (B) shows activity of the fragments spanning the indicated regions. The results of pGL3-Basic constructs containing the promoter fragments (gray bars) are normalized to the paired empty vector control (black bars) and represent the mean±SEM of 2 independent experiments.

An ~300 bp fragment of the CD70 (TNFSF7) gene possessing promoter activity was identified using deletional analysis and transient transfection of reporter constructs (See, e.g., Example 10, FIG. 11). The promoter region contains binding sites for several transcription factors including AP-1, Sp1, NF-κB and AP-2 (See, FIG. 10). Bisulfite sequencing of primary CD4+ and CD8+ T cells revealed complete demethylation of the promoter sequence, with progressively greater methylation in the more distal 5' regions (See, e.g., Example 11, FIG. 12). Hypomethylation of regulatory regions is characteristic of a transcriptionally permissive chromatin configuration, and active promoters are typically hypomethylated (Attwood et al., Cell Mol Life Sci 59:241 (2002)). Thus, in some embodiments, the present invention provides methods of identifying or characterizing an autoimmune disease (e.g., SLE) based on methylation of the CD70 promoter (See, e.g., Example 12, FIG. 13). In some embodiments, hypomethylation is correlated with active disease. The present invention also provides methods for determining a subjects response to therapy. For example, in some embodiments, a subject can be categorized as responding favorably to therapy for autoimmune disease based on an increase in methylation of CD70 or the CD40L promoter, a decrease in expression of CD70 (e.g., decreased mRNA or transcript levels) and/or a decrease in the expression of the CD70 protein. In some embodiments, the methylation status of IgE FCRγ1, CD30, CD40L or CD11c, alone or in combination with other markers, such as CD70, are used to identify or characterize autoimmune disease.

Treating CD4+, but not CD8+, T cells with 2 direct Dnmt inhibitors (5-azaC and Pca) (See, e.g., Friedman et al., Mol Pharmacol 19:314 (1981); Scheinbart et al., J Rheumatol 18:530 (1991)) or 3 ERK pathway inhibitors (PD98059, U0126 and Hyd) known to decrease Dnmt expression (Deng et al., Arthritis Rheum 48:746 (2003)), all increased steady state levels of CD70 mRNA (See, e.g., Example 13, FIG. 16). While a mechanism is not necessary to practice the present invention, and the invention is not limited to a particular mechanism, it is contemplated that, since a property common to all 5 agents is DNA methylation inhibition, that methods of the present invention function to identify or characterize autoimmune disease comprising the characterizing methylation status (e.g., demethylation) of sequences affecting gene expression (e.g., demethylation of genes involved in autoimmune disease). The present invention identified that all 5 agents tested during development of the present invention demethylate a sequence located within 200 bp upstream of the promoter (See, e.g., Example 13, FIGS. 13 and 17). Patch methylation of reporter constructs indicated that methylation of the affected region can suppress promoter function, as reflected by transient transfection assays. Thus, in some embodiments, the present invention provides methods of identifying, characterizing/monitoring, or treating a subject having or suspected of having an autoimmune disease comprising characterizing or altering the status (e.g., the methylation status or activity) of the CD 70 promoter. In some embodiments, the present invention provides methods for altering (e.g., increase) methylation of genes involved in autoimmune disease (e.g., CD70) in order to treat subjects showing symptoms of autoimmune disease.

The present invention further provides a method of identifying genes involved in autoimmune disease. In some embodiments, the genes identified are aberrantly expressed due to increased or decreased methylation patterns as compared to healthy controls.

B. Detection of Markers of Autoimmune or Chronic Inflammatory Disease

In some embodiments, the present invention provides methods for detection of expression of autoimmune or chronic inflammatory disease markers (e.g., SLE or RA markers). In preferred embodiments, expression is measured directly (e.g., at the RNA or protein level). In some embodiments, expression is detected in tissue samples (e.g., biopsy tissue). In other embodiments, expression is detected in bodily fluids (e.g., including but not limited to, plasma, serum, whole blood, mucus, and urine).

For example, using the compositions and methods of the present invention, it was determined that treatment with methylation inhibitors increase CD40L mRNA (See, e.g., Example 14, FIGS. 18-22). Thus, in some embodiments, the present invention provides methods of identifying or characterizing an autoimmune disease (e.g., RA or SLE), or response thereof to therapy, based on the level of CD40L expression (e.g., mRNA or transcript levels).

The present invention further provides panels and kits for the detection of markers. In preferred embodiments, the presence of an autoimmune or chronic inflammatory disease marker is used to provide a prognosis to a subject. For example, the detection of high levels of CD70 or CD40L, as compared to controls, in a sample is indicative of an autoimmune or chronic inflammatory disease that is active. The information provided is also used to direct the course of treatment. For example, if a subject is found to have a marker indicative of a severe state of autoimmune or chronic inflammatory disease, additional therapies (e.g., anti-inflammatories) can be started at a earlier point when they are more likely to be effective. In addition, if a subject is found to have an autoimmune or chronic inflammatory disease that is not responsive to a specific therapy, the expense and inconvenience of such therapies can be avoided.

The present invention is not limited to the markers described above. Any suitable marker that correlates with autoimmune or chronic inflammatory disease or the progression such disease may be utilized, including but not limited to, those described in the illustrative examples below (e.g., CD70, CD40L, perforin, CD11a, CD11c, CD30, IgE FCRγ1, etc). Additional markers are also contemplated to be within the scope of the present invention. Any suitable method may be utilized to identify and characterize autoimmune or chronic inflammatory disease markers suitable for use in the methods of the present invention, including but not limited to, those described in illustrative Examples 1-13 below. For example, in some embodiments, markers identified as being up or down-regulated in autoimmune or chronic inflammatory disease using the T cell stimulation and methylation pattern expression methods of the present invention are further characterized using tissue microarray, immunohistochemistry, Northern blot analysis, siRNA or antisense RNA inhibition, mutation analysis, investigation of expression with clinical outcome, as well as other methods disclosed herein.

In some embodiments, the present invention provides a panel for the analysis of a plurality of markers. The panel allows for the simultaneous analysis of multiple markers correlating with autoimmune or chronic inflammatory disease. For example, a panel may include markers identified as correlating with a chronic inflammatory disease but not an autoimmune disease, an autoimmune disease but not a chronic inflammatory disease, or both, in a subject that is/are likely or not likely to respond to a given treatment. Depending on the subject, panels may be analyzed alone or in combination in order to provide the best possible diagnosis and prognosis. Markers for inclusion on a panel are selected by screening for their predictive value using any suitable method, including but not limited to, those described in the illustrative examples below.

In some embodiments, the present invention provides methylation sensitive PCR for identifying or characterizing autoimmune or chronic inflammatory disease. In some embodiments, individual markers are analyzed. In other embodiments, a panel of multiple markers are analyzed.

In other embodiments, the present invention provides an expression profile map comprising expression profiles of autoimmune or chronic inflammatory disease of various severity or prognoses. Such maps can be used for comparison with patient samples. In some embodiments comparisons are made using the method described in Example 11. However, the present invention is not limited to the method described in Example 11. Any suitable method may be utilized, including but not limited to, by computer comparison of digitized data. The comparison data is used to provide diagnoses and/or prognoses to patients.

1. Detection of RNA

In some preferred embodiments, detection of autoimmune or chronic inflammatory disease markers (e.g., including but not limited to, those disclosed herein) is detected by measuring the expression of corresponding mRNA in a tissue or other sample (e.g., a blood sample). mRNA expression may be measured by any suitable method, including but not limited to, those disclosed below.

In some embodiments, RNA is detection by Northern blot analysis. Northern blot analysis involves the separation of RNA and hybridization of a complementary labeled probe.

In other embodiments, RNA expression is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific nucleic acid (e.g., RNA) sequences by using structure-specific enzymes to cleave a complex formed by the hybridization of overlapping oligonucleotide probes.

In still further embodiments, RNA (or corresponding cDNA) is detected by hybridization to an oligonucleotide probe. A variety of hybridization assays using a variety of technologies for hybridization and detection are available. For example, in some embodiments, TaqMan assay (PE Biosystems, Foster City, Calif.; See e.g., U.S. Pat. No. 5,538,848, which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR(RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

2. Detection of Protein

In other embodiments, gene expression of autoimmune or chronic inflammatory disease markers is detected by measuring the expression of the corresponding protein or polypeptide. Protein expression may be detected by any suitable method. In some embodiments, proteins are detected by immunohistochemistry method of Example 5. In other embodiments, proteins are detected by their binding to an antibody raised against the protein. The generation of antibodies is described below.

Antibody binding is detected by techniques known in the art (e.g., radioimmunoassay, ELISA (enzyme-1 inked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to autoimmune or chronic inflammatory disease markers is utilized.

In other embodiments, the immunoassay described in U.S. Pat. Nos. 5,599,677 and 5,672,480; each of which is herein incorporated by reference.

3. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of autoimmune or chronic inflammatory disease to respond to a specific therapy) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or severity of disease.

4. Kits

In yet other embodiments, the present invention provides kits for the detection and characterization of autoimmune or chronic inflammatory disease. In some embodiments, the kits contain antibodies specific for an autoimmune or chronic inflammatory disease marker, in addition to detection reagents and buffers. In other embodiments, the kits contain reagents specific for the detection of mRNA or cDNA (e.g., oligonucleotide probes or primers). For example, in some embodiments, the kits contain primers and reagents needed to perform methylation sensitive PCR for detection and characterization of autoimmune or chronic inflammatory disease. In preferred embodiments, the kits contain all of the components necessary to perform a detection assay, including all controls, directions for performing assays, and any necessary software for analysis and presentation of results.

5. In vivo Imaging

In some embodiments, in vivo imaging techniques are used to visualize the expression of autoimmune or chronic inflammatory disease markers in an animal (e.g., a human or non-human mammal). For example, in some embodiments, autoimmune or chronic inflammatory disease marker mRNA or protein is labeled using a labeled antibody specific for the autoimmune or chronic inflammatory disease marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the autoimmune or chronic inflammatory disease markers of the present invention are described below.

The in vivo imaging methods of the present invention are useful in the diagnosis and characterization (e.g., response to treatment) of autoimmune or chronic inflammatory disease that express the autoimmune or chronic inflammatory disease markers of the present invention (e.g., SLE or RA). In vivo imaging is used to visualize the presence of a marker indicative of the autoimmune or chronic inflammatory disease. Such techniques allow for diagnosis without the use of an unpleasant biopsy. The in vivo imaging methods of the present invention are also useful for providing prognoses to autoimmune or chronic inflammatory disease patients. For example, the presence of a marker indicative of autoimmune or chronic inflammatory disease likely to respond to therapy can be detected. The in vivo imaging methods of the present invention can further be used to detect sites of inflammation in multiple parts of the body.

In some embodiments, reagents (e.g., antibodies) specific for the autoimmune or chronic inflammatory disease markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In some embodiments, the present invention provides compositions (e.g., antibodies) and methods of monitoring relapsing-remitting (RR) multiple sclerosis (MS), as conventional magnetic resonance (MR) imaging (MRI) has proved to be a valuable tool to assess the lesion burden and activity over time (See, e.g., Rovaris and Fillipi, J Rehab Res Dev, Volume 39,243 (2002)). In some embodiments, the present invention provides methods of in vivo assessment of lung inflammatory cell activity in patients with COPD or asthma (See, Eur Respir J Apr.; 21(4):567 (2003). The compositions and methods of the present invention are not limited to any particular autoimmune or chronic inflammatory disease. Indeed, the compositions and methods of the present invention find use in identifying, monitoring and/or treating a variety of autoimmune or chronic inflammatory diseases including, but not limited to Autoimmune hepatitis, Multiple Sclerosis, Systemic Lupus Erythematosus, Myasthenia Gravis, Type I diabetes, Rheumatoid Arthritis, Psoriasis, Hashimoto's Thyroiditis, Grave's disease, Ankylosing Spondylitis Sjogrens Disease, CREST syndrome, Scleroderma Atherosclerosis, Congestive Heart Failure, Crohn's disease, Ulcerative Colitis, Polyarteritis nodosa, Whipple's Disease, Primary Sclerosing Cholangitis and many more.

In other embodiments, antibodies are radioactively labeled. The use of antibodies for in vivo diagnosis is well known in the art. Sumerdon et al., (Nucl. Med. Biol 17:247-254 (1990)) have described an optimized antibody-chelator for the radioimmunoscintographic imaging of tumors using Indium-111 as the label. Griffin et al., (J Clin One 9:631-640 (1991)) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 (1991)). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 (1980)) for In-111 and Tc-99m, and by Scheinberg et al. (Science 215:1511 (1982)). Other chelating agents may also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 (1982)) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A preferred method of labeling immunoglobulins with Tc-99m is that described by Wong et al. (Int. J. Appl. Radiat. Isot., 29:251 (1978)) for plasma protein, and recently applied successfully by Wong et al. (J. Nucl. Med., 23:229 (1981)) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific autoimmune or chronic inflammatory disease marker of the present invention, to insure that the antigen binding site on the antibody will be protected. The antigen is separated after labeling.

In still further embodiments, in vivo biophotonic imaging (XENOGEN, Almeda, Calif.) is utilized for in vivo imaging. This real-time in vivo imaging utilizes luciferase. The luciferase gene is incorporated into cells, microorganisms, and animals (e.g., as a fusion protein with a autoimmune and chronic inflammatory disease marker of the present invention). When active, it leads to a reaction that emits light. A CCD camera and software is used to capture the image and analyze it.

II. Antibodies

The present invention provides isolated antibodies. In preferred embodiments, the present invention provides monoclonal antibodies that specifically bind to an isolated polypeptide comprised of at least five amino acid residues of the autoimmune or chronic inflammatory disease markers described herein (e.g., CD70, CD40L, etc.). These antibodies find use in the diagnostic methods described herein.

An antibody against an autoimmune or chronic inflammatory disease protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 (1975)). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a autoimmune or chronic inflammatory disease protein or autoantibody of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against an autoimmune or chronic inflammatory disease marker of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, an autoimmune or chronic inflammatory disease marker of the present invention (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

III. Drug Screening

In some embodiments, the present invention provides drug screening assays (e.g., to screen for anti-autoimmune or anti-chronic inflammatory disease drugs). The screening methods of the present invention utilize autoimmune or chronic inflammatory disease markers identified using the methods of the present invention (e.g., including but not limited to, CD70, CD40L, perforin, CD11a, CD30, CD11c, and IgE FCRγ1). For example, in some embodiments, the present invention provides methods of screening for compound that alter (e.g., increase or decrease) the expression of autoimmune or chronic inflammatory disease marker genes. In some embodiments, candidate compounds are antisense agents (e.g., oligonucleotides) directed against autoimmune or chronic inflammatory disease markers. See Section IV below for a discussion of antisense therapy. In other embodiments, candidate compounds are antibodies that specifically bind to an autoimmune or chronic inflammatory disease marker of the present invention.

In one screening method, candidate compounds are evaluated for their ability to alter autoimmune or chronic inflammatory disease marker expression by contacting a compound with a cell expressing a autoimmune or chronic inflammatory disease marker and then assaying for the effect of the candidate compounds on expression. In some embodiments, the effect of candidate compounds on expression of an autoimmune or chronic inflammatory disease marker gene is assayed for by detecting the level of autoimmune or chronic inflammatory disease marker mRNA expressed by the cell. mRNA expression can be detected by any suitable method (e.g., by the methods discussed in Examples 8 and 12 below. In other embodiments, the effect of candidate compounds on expression of autoimmune or chronic inflammatory disease marker genes is assayed by measuring the level of polypeptide encoded by the autoimmune or chronic inflammatory disease markers (See, e.g., Example 3). The level of polypeptide expressed can be measured using any suitable method, including but not limited to, those disclosed herein.

Specifically, the present invention provides screening methods for identifying modulators, i.e., candidate or test compounds or agents (e.g., proteins, peptides, peptidomimetics, peptoids, small molecules or other drugs) which bind to autoimmune or chronic inflammatory disease markers of the present invention, have an inhibitory (or stimulatory) effect on, for example, autoimmune or chronic inflammatory disease marker expression or autoimmune or chronic inflammatory disease markers activity, or have a stimulatory or inhibitory effect on, for example, the expression or activity of an autoimmune or chronic inflammatory disease marker substrate. Compounds thus identified can be used to modulate the activity of target gene products (e.g., autoimmune or chronic inflammatory disease marker genes) either directly or indirectly in a therapeutic protocol, to elaborate the biological function of the target gene product, or to identify compounds that disrupt normal target gene interactions. Compounds which inhibit the activity or expression of autoimmune or chronic inflammatory disease markers are useful in the treatment of autoimmune or chronic inflammatory disease (e.g., SLE, RA, MS, etc.)

In one embodiment, the invention provides assays for screening candidate or test compounds that are substrates of an autoimmune or chronic inflammatory disease marker protein or polypeptide or a biologically active portion thereof. In another embodiment, the invention provides assays for screening candidate or test compounds that bind to or modulate the activity of an autoimmune or chronic inflammatory disease marker protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 (1994)); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 (1993); Erb et al., Proc. Natl. Acad. Sci. USA 91:11422 (1994); Zuckermann et al., J. Med. Chem. 37:2678 (1994); Cho et al., Science 261:1303 (1993); Carrell et al., Angew. Chem. Int. Ed. Engl. 33.2059 (1994); Carell et al., Angew. Chem. Int. Ed. Engl. 33:2061 (1994); and Gallop et al., J. Med. Chem. 37:1233 (1994).

Libraries of compounds may be presented in solution (e.g., Houghten, Biotechniques 13:412-421 (1992)), or on beads (Lam, Nature 354:82-84 (1991)), chips (Fodor, Nature 364:555-556 (1993)), bacteria or spores (U.S. Pat. No. 5,223,409; herein incorporated by reference), plasmids (Cull et al., Proc. Nad. Acad. Sci. USA 89:18651869 (1992)) or on phage (Scott and Smith, Science 249:386-390 (1990); Devlin Science 249: 404-406 (1990); Cwirla et al., Proc. Natl. Acad. Sci. 87:6378-6382 (1990); Felici, J. Mol. Biol. 222:301 (1991)).

In one embodiment, an assay is a cell-based assay in which a cell that expresses an autoimmune or chronic inflammatory disease marker protein or biologically active portion thereof is contacted with a test compound, and the ability of the test compound to modulate the autoimmune or chronic inflammatory disease marker's activity is determined. Determining the ability of the test compound to modulate autoimmune or chronic inflammatory disease marker activity can be accomplished by monitoring, for example, B cell stimulation or changes in enzymatic activity. The cell, for example, can be of mammalian origin.

The ability of the test compound to modulate autoimmune or chronic inflammatory disease marker binding to a compound, e.g., an autoimmune or chronic inflammatory disease marker substrate, can also be evaluated. This can be accomplished, for example, by coupling the compound, e.g., the substrate, with a radioisotope or enzymatic label such that binding of the compound, e.g., the substrate, to an autoimmune or chronic inflammatory disease marker can be determined by detecting the labeled compound, e.g., substrate, in a complex.

Alternatively, the autoimmune or chronic inflammatory disease marker is coupled with a radioisotope or enzymatic label to monitor the ability of a test compound to modulate autoimmune or chronic inflammatory disease marker binding to an autoimmune or chronic inflammatory disease markers substrate in a complex. For example, compounds (e.g., substrates) can be labeled with $^{125}I$, $^{35}S$ $^{14}C$ or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., an autoimmune or chronic inflammatory disease marker substrate) to interact with an autoimmune or chronic inflammatory disease marker with or without the labeling of any of the interactants can be evaluated. For example, a microphysiometer can be used to detect the interaction of a compound with an autoimmune or chronic inflammatory disease marker without the labeling of either the compound or the autoimmune or chronic inflammatory disease marker (McConnell et al. Science 257:1906-1912 (1992)). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and autoimmune or chronic inflammatory disease markers.

In yet another embodiment, a cell-free assay is provided in which an autoimmune or chronic inflammatory disease marker protein or biologically active portion thereof is contacted with a test compound and the ability of the test compound to bind to the autoimmune or chronic inflammatory disease marker protein or biologically active portion thereof is evaluated. Preferred biologically active portions of the autoimmune or chronic inflammatory disease markers proteins to be used in assays of the present invention include fragments that participate in interactions with substrates or other proteins, e.g., fragments with high surface probability scores.

Cell-free assays involve preparing a reaction mixture of the autoimmune or chronic inflammatory disease target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 15 the assay should be maximal. An FRET binding event can be conveniently measured through standard fluorometric detection means well known in the art (e.g., using a fluorimeter).

In another embodiment, determining the ability of the autoimmune or chronic inflammatory disease marker proteins to bind to a target molecule can be accomplished using real-time Biomolecular Interaction Analysis (BIA) (see, e.g., Sjolander and Urbaniczky, Anal. Chem. 63:2338-2345 (1991) and Szabo et al. Curr. Opin. Struct. Biol. 5:699-705 (1995)). "Surface plasmon resonance" or "BIA" detects biospecific interactions in real time, without labeling any of the interactants (e.g., BIACORE). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize autoimmune or chronic inflammatory disease markers, an anti-autoimmune or anti-chronic inflammatory disease marker antibody or its target molecule to facilitate separation of complexed from non-complexed forms of one or both of the proteins, as well as to accommodate automation of the assay. Binding of a test compound to an autoimmune or chronic inflammatory disease marker protein, or interaction of an autoimmune or chronic inflammatory disease marker protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-autoimmune or chronic inflammatory disease marker fusion proteins or glutathione-S-transferase/target fusion proteins can be adsorbed onto glutathione Sepharose beads (SIGMA-ALDRICH, St. Louis, Mo.) or glutathione-derivatized microtiter plates, which are then combined with the test compound or the test compound and either the non-adsorbed target protein or autoimmune or chronic inflammatory disease marker protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of autoimmune or chronic inflammatory disease markers binding or activity determined using standard techniques. Other techniques for immobilizing either autoimmune or chronic inflammatory disease marker proteins or a target molecule on matrices include using conjugation of biotin and streptavidin. Biotinylated autoimmune or chronic inflammatory disease marker protein or target molecules can be prepared from biotin-NHS (N-hydroxy-succinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with autoimmune or chronic inflammatory disease marker protein or target molecules but which do not interfere with binding of the autoimmune or chronic inflammatory disease marker proteins to its target molecule. Such antibodies can be derivatized to the wells of the plate, and unbound target or autoimmune or chronic inflammatory disease marker proteins trapped in the wells by antibody conjugation. Methods for detecting such complexes, in addition to those described above for the GST-immobilized complexes, include immunodetection of complexes using antibodies reactive with the autoimmune or chronic inflammatory disease marker protein or target molecule, as well as enzyme-linked assays which rely on detecting an enzymatic activity associated with the autoimmune or chronic inflammatory disease marker protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 (1993)); chromatography (gel filtration chromatography, ion-exchange chromatography); electrophoresis (see, e.g., Ausubel et al., eds. Current Protocols in Molecular Biology 1999, J. Wiley: New York); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit 11:141-8 (1998);

Hageand Tweed J. Chromatogr. Biomed. Sci. Appl 699:499-525 (1997)). Further, fluorescence energy transfer may also be conveniently utilized, as described herein, to detect binding without further purification of the complex from solution.

The assay can include contacting the autoimmune or chronic inflammatory disease marker protein or biologically active portion thereof with a known compound that binds the autoimmune or chronic inflammatory disease marker to form an assay mixture, contacting the assay mixture with a test compound, and determining the ability of the test compound to interact with an autoimmune or chronic inflammatory disease marker protein, wherein determining the ability of the test compound to interact with an autoimmune or chronic inflammatory disease marker protein includes determining the ability of the test compound to preferentially bind to autoimmune or chronic inflammatory disease markers or biologically active portion thereof, or to modulate the activity of a target molecule, as compared to the known compound.

To the extent that autoimmune or chronic inflammatory disease markers can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, autoimmune or chronic inflammatory disease marker protein can be used as a "bait protein" in a two-hybrid assay or three-hybrid assay (see, e.g., U.S. Pat. No. 5,283,317; Zervos et al., Cell 72:223-232 (1993); Madura et al., J. Biol. Chem. 268.12046-12054 (1993); Bartel et al., Biotechniques 14:920-924 (1993); Iwabuchi et al., Oncogene 8:1693-1696 (1993); and Brent WO 94/10300; each of which is herein incorporated by reference), to identify other proteins, that bind to or interact with autoimmune or chronic inflammatory disease markers ("autoimmune disease- or chronic inflammatory disease-binding proteins") and are involved in autoimmune or chronic inflammatory disease marker activity. Such autoimmune or chronic inflammatory disease marker-binding proteins can be activators or inhibitors of signals by the autoimmune or chronic inflammatory disease marker proteins or targets as, for example, downstream elements of an autoimmune or chronic inflammatory disease markers-mediated signaling pathway.

Modulators of autoimmune or chronic inflammatory disease marker expression can also be identified. For example, a cell or cell free mixture is contacted with a candidate compound and the expression of autoimmune or chronic inflammatory disease marker mRNA or protein evaluated relative to the level of expression of autoimmune or chronic inflammatory disease marker mRNA or protein in the absence of the candidate compound. When expression of autoimmune or chronic inflammatory disease marker mRNA or protein is greater in the presence of the candidate compound than in its absence, the candidate compound is identified as a stimulator of autoimmune or chronic inflammatory disease marker mRNA or protein expression. Alternatively, when expression of autoimmune or chronic inflammatory disease marker mRNA or protein is less (i.e., statistically significantly less) in the presence of the candidate compound than in its absence, the candidate compound is identified as an inhibitor of autoimmune or chronic inflammatory disease marker mRNA or protein expression. The level of autoimmune or chronic inflammatory disease marker mRNA or protein expression can be determined by methods described herein for detecting autoimmune or chronic inflammatory disease markers mRNA or protein.

A modulating agent can be identified using a cell-based or a cell free assay, and the ability of the agent to modulate the activity of an autoimmune or chronic inflammatory disease marker protein can be confirmed in vivo, e.g., in an animal such as an animal model for a disease (e.g., an animal with lupus or arthritis) or T cells from an autoimmune or chronic inflammatory disease subject, or cells from an autoimmune or chronic inflammatory disease cell line.

This invention further pertains to novel agents identified by the above-described screening assays (See e.g., below description of autoimmune or chronic inflammatory disease therapies). Accordingly, it is within the scope of this invention to further use an agent identified as described herein (e.g., an autoimmune or chronic inflammatory disease marker modulating agent, an antisense autoimmune or chronic inflammatory disease marker nucleic acid molecule, a siRNA molecule, an autoimmune or chronic inflammatory disease marker specific antibody, or an autoimmune or chronic inflammatory disease marker-binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments as described herein.

IV. Autoimmune and/or Chronic Inflammatory Disease Therapies

In some embodiments, the present invention provides therapies for autoimmune or chronic inflammatory disease (e.g., SLE or RA). In some embodiments, therapies target autoimmune or chronic inflammatory disease markers (e.g., including but not limited to, CD70, perforin, IgE FCRγ1, CD30, CD40L or CD11c).

A. Antisense Therapies

In some embodiments, the present invention targets the expression of autoimmune or chronic inflammatory disease markers. For example, in some embodiments, the present invention employs compositions comprising oligomeric antisense compounds, particularly oligonucleotides (e.g., those identified in the drug screening methods described above), for use in modulating the function of nucleic acid molecules encoding autoimmune or chronic inflammatory disease markers of the present invention, ultimately modulating the amount of autoimmune or chronic inflammatory disease marker expressed. This is accomplished by providing antisense compounds that specifically hybridize with one or more nucleic acids encoding autoimmune or chronic inflammatory disease markers of the present invention. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription (e.g., via transcription factor decoys). The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of autoimmune or chronic inflammatory disease markers of the present invention. In the context of the present invention, "modulation" means either an increase (stimulation) or a decrease (inhibition) in the expression of a gene. For example, expression may be inhibited to potentially prevent inflammation or arthritis. For example, any means may be used to for modulation including RNAi (See, e.g., U.S. Pat. No. 6,897,069, and U.S. Pub. No. 2004-0053876, published Mar. 18, 2004, herein incorporated by reference in their entireties for all purposes).

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding an autoimmune or chronic inflammatory disease marker of the present invention. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

In some embodiments, target sites for antisense inhibition are identified using commercially available software programs (e.g., Biognostik, Gottingen, Germany; SysArris Software, Bangalore, India; Antisense Research Group, University of Liverpool, Liverpool, England; GeneTrove, Carlsbad, Calif.). In other embodiments, target sites for antisense inhibition are identified using the accessible site method described in PCT Publication WO 01/98537 A2, herein incorporated by reference.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular —$CH_2$—, —NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$—, and —O—N($CH_3$)—$CH_2$—$CH_2$— (wherein the native phosphodiester backbone is represented as —O—P—O—$CH_2$—) of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O(($CH_2$)$_n$O)$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON(($CH_2$)$_n$$CH_3$))$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, S$CH_3$, OCN, Cl, Br, CN, $CF_3$, OC$F_3$, SOC$H_3$, S$O_2$$CH_3$, ON$O_2$, N$O_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2$$CH_2$O$CH_3$, also known as 2'-O-(2-methoxyethyl) or 2'-MOE) (Martin et al., Helv. Chim. Acta 78:486 (1995)) i.e., an alkoxyalkoxy group. A further preferred modification includes 2'-dimethylaminooxyethoxy (i.e., a O($CH_2$)$_2$ON($CH_3$)$_2$ group), also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$.

Other preferred modifications include 2'-methoxy(2'-O—$CH_3$), 2'-aminopropoxy(2'-O$CH_2$$CH_2$$CH_2$$NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2. degree ° C. and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-5-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisense oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

B. Genetic Therapies

The present invention contemplates the use of any genetic manipulation for use in modulating the expression of autoimmune or chronic inflammatory disease markers of the present invention. Examples of genetic manipulation include, but are not limited to, gene knockout (e.g., removing the autoimmune and chronic inflammatory disease marker gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

C. Antibody Therapy

In some embodiments, the present invention provides antibodies that target cells that express an autoimmune or chronic inflammatory disease marker of the present invention (e.g., CD70, CD40L, CD11a, CD11c, etc.). Any suitable antibody (e.g., monoclonal, polyclonal, or synthetic) may be utilized in the therapeutic methods disclosed herein. In preferred embodiments, the antibodies used for autoimmune or chronic inflammatory disease therapy are humanized-antibodies. Methods for humanizing antibodies are well known in the art (See e.g., U.S. Pat. Nos. 6,180,370, 5,585,089, 6,054,297, and 5,565,332; each of which is herein incorporated by reference).

In some embodiments, the therapeutic antibodies comprise an antibody generated against an autoimmune or chronic inflammatory disease marker of the present invention, wherein the antibody is conjugated to a cytotoxic agent. In some embodiments, an autoimmune or chronic inflammatory disease specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of autoreactive cells (e.g., autoreactive T and B cells). The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention may include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments may include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some preferred embodiments, deglycosylated ricin A chain is utilized.

In any event, it is proposed that agents such as these may, if desired, be successfully conjugated to an antibody, in a manner that will allow their targeting, internalization, release or presentation to blood components at the site of the targeted autoimmune or chronic inflammatory diseased cells as required using known conjugation technology (See, e.g., Ghose et al., Methods Enzymol., 93:280 (1983)).

For example, in some embodiments the present invention provides immunotoxins targeted an autoimmune or chronic inflammatory disease marker of the present invention (e.g., hepsin, pim-1, EZH2, Annexin, CTBP, GP73, and AMACR). Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 (1988)).

In preferred embodiments, antibody based therapeutics are formulated as pharmaceutical compositions as described below. In preferred embodiments, administration of an antibody composition of the present invention results in a measurable decrease in autoimmune or chronic inflammatory disease (e.g., decrease or elimination T cell autoreactivity).

D. Pharmaceutical Compositions

The present invention further provides pharmaceutical compositions (e.g., comprising the antisense or antibody compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the autoimmune or chronic inflammatory disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

V. Transgenic Animals Expressing Autoimmune or Chronic Inflammatory Disease Marker Genes The present invention contemplates the generation of transgenic animals comprising an exogenous autoimmune or chronic inflammatory disease marker gene of the present invention or mutants and variants thereof (e.g., truncations or single nucleotide polymorphisms). In preferred embodiments, the transgenic animal displays an altered phenotype (e.g., increased or decreased presence of markers) as compared to wild-type animals. Methods for analyzing the presence or absence of such phenotypes include but are not limited to, those disclosed herein. In some preferred embodiments, the transgenic animals further display an increased or decreased inflammation or arthritis or evidence of autoimmune or chronic inflammatory disease.

The transgenic animals of the present invention find use in drug (e.g., autoimmune or chronic inflammatory disease therapy) screens. In some embodiments, test compounds (e.g., a drug that is suspected of being useful to treat autoimmune or chronic inflammatory disease) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 (1985)). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 (1976)). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. (1986)). The viral vector system used to introduce the transgene is typically a replication-defective retrovirus carrying the transgene (Jahner et al., Proc. Natl. Acad Sci. USA 82:6927 (1985)). Transfection is easily and efficiently obtained by culturing the blastomeres on a monolayer of virus-producing cells (Stewart, et al., EMBO J., 6:383 (1987)). Alternatively, infection can be performed at a later stage. Virus or virus-producing cells can be injected into the blastocoele (Jahner et al., Nature 298:623 (1982)). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra (1982)). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT Publication WO 90/08832 (1990), and Haskell and Bowen, Mol. Reprod. Dev., 40:386 (1995)).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 (1981); Bradley et al., Nature 309:255 (1984); Gossler et al., Proc. Acad. Sci. USA 83:9065 (1986); and Robertson et al., Nature 322:445 (1986)). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 (1988)). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

EXPERIMENTAL

The following examples are provided in order to demonstrate and further illustrate certain preferred embodiments and aspects of the present invention and are not to be construed as limiting the scope thereof.

In the experimental disclosure that follows, the following abbreviations apply: g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade); U (units), kb (kilobase); bp (base pair); hr (hour); min (minute); FALCON (FALCON, Franklin Lakes, N.J.); REMEL (REMEL, Inc., Lenexa, Kans.); SIGMA-ALDRICH (SIGMA-ALDRICH, St. Louis, Mo.); PROMEGA (PROMEGA, Madison, Wis.); ROCHE (ROCHE, Indianapolis, Ind.); PHARMINGEN (BD-PHARMINGEN, San Diego, Calif.); Miltenyi (Miltenyi Biotec, Sunnyvale/Auburn, Calif.); COSTAR (Corning Inc., Acton, Mass.); DAKO (DAKOCYTOMATION, Glostrup, Denmark); Southern Biotech, (Southern Biotechnology Associates, Inc Birmingham Ala.), MOLECULAR DEVICES (MOLECULAR DEVICES Corp., Sunnyvale, Calif.); SYSTAT (SYSTAT Software Inc., Richmond, Calif.); and Corbett (Corbett Research, Sydney Australia).

Example 1

Materials and Methods

Subjects. Subjects of the present invention were of two groups (See, e.g., Table 1 and Table 2). For one of the groups, systemic lupus erythematosus (SLE) patients were recruited from the outpatient and inpatient services at the University of Michigan. For the second group, SLE and rheumatoid arthritis (RA) patients were recruited from the outpatient Rheumatology clinics and inpatient services at the University of Michigan. For both groups, age-, race-, and sex-matched control subjects were recruited by advertising. The study protocols were approved by the University of Michigan Institutional Review Board. Patients with SLE and RA met the American College of Rheumatology criteria for these diseases (See, e.g., Tan et al., Arthritis Rheum 25, 1271 (1982); Arnett et al., Arthritis Rheum 31, 315-324 (1987)), and SLE disease activity was assessed by the SLE-Disease Activity Index (SLEDAI) (See, e.g., Bombardier et al., Arthritis Rheum 35, 360 (1992)). Active disease was defined as a SLEDAI score$\geq$5. Relevant clinical information regarding the study subjects is shown in Tables 1 and 2.

TABLE 1

| Patient | Age/race/sex | SLEDAI score or diagnosis | Medications |
|---|---|---|---|
| SLE patients | | | |
| 1 | 49/W/F | 6 | HCQ |
| 2 | 28/B/F | 10 | MMF 2 gm, HCQ, Pred. 15 mg/day |
| 3 | 38/B/F | 10 | MMF 2.5 gm, HCQ, Pred. 12 mg/day |
| 4 | 25/W/F | 7 | Pred. 5 mg/day |
| 5 | 23/W/M | 5 | HCQ, Pred. 5 mg/day |
| 6 | 53/W/F | 12 | Pred. 60 mg/day |
| 7 | 23/W/F | 12 | HCQ, Pred. 20 mg/day |
| 8 | 30/W/F | 8 | MMF 2.5 gm, HCQ, Pred. 20 mg/day |
| 9 | 31/W/F | 6 | MMF 2 gm, HCQ, quinacrine, Pred. 10 mg/day |
| 10 | 24/W/F | 8 | MMF 2 gm, HCQ, Pred. 36 mg/day |
| 11 | 41/W/F | 10 | Pred. 15 mg/day |
| 12 | 54/W/F | 2 | HCQ |
| 13 | 38/W/F | 0 | Pred. 1.5 mg/day |
| 14 | 43/W/F | 0 | Pred. 5 mg/day, MTX, MMF |
| Control patients | | | |
| 15 | 65/W/F | Dermatomyositis | Pred. 10 mg/day, MTX, MMF |
| 16 | 39/W/F | CNS vasculitis | Pred. 15 mg/day, CYC |
| 17 | 34/W/F | WG | Pred. 40 mg/day, CYC, etanercept |

SLEDAI (Systemic Lupus Erythematosus Disease Activity Index); HCQ (hydroxychloroquine); MMF (mycophenolate mofetil); Pred. (prednisone); MTX (methotrexate); CNS (central nervous system); CYC (cyclophosphamide); WG (Wegener's granulomatosis).

TABLE 2

| Patient | Age/Race/Gender | SLEDAI/Dx | Medications |
|---|---|---|---|
| 1 | 32/W/F | 2 | Quin/Plaq/MTX/Pred 7.5 |
| 2 | 40/W/F | 4 | Leflunomide |
| 3 | 31/W/F | 4 | Quin/Plaq |
| 4 | 56/W/F | 2 | Pred 10 |
| 5 | 30/H/F | 4 | MM 2.0 q/Pred 10 |
| 6 | 40/B/F | 6 | MM 2.0/Pred 5 |

TABLE 2-continued

| Patient | Age/Race/Gender | SLEDAI/Dx | Medications |
|---|---|---|---|
| 7 | 47/W/F | 8 | Methylprednisolone 60 |
| 8 | 23/W/F | 6 | MM 1.5/Pred 5 |
| 9 | 54/W/F | 8 | Azathioprine/Pred 5 |
| 10 | 28/B/F | 8 | Plaq/Pred 5 |
| 11 | 21/W/F | 12 | Plaq/MM 1.0/Pred 10 |
| 12 | 60/W/F | RA | MTX |
| 13 | 54/A/F | RA | MTX |
| 14 | 54/W/F | RA | none |

[a]Quin, quinacrine: Plaq, plaquenil; MTX, methotrexate; Pred, prednisone; MM, mycophenylate mofetil.

Cells and cell culture. Peripheral blood mononuclear cells (PBMCS) were isolated by density-gradient centrifugation. T cells were then isolated by E-rosetting (See, e.g., Golbus et al., Clin Immunol Immunopathol 46, 129 (1988)). Purity, assessed by staining with fluorescein isothiocyanate (FITC)—conjugated anti-CD3 and flow cytometry, was typically 87-94%. Where indicated, the cells were cultured in RPMI 1640/10% fetal calf serum (FCS) supplemented with interleukin-2 (IL-2) (See, e.g., Richardson et al., Clin Immunol Immunopathol 55, 368 (1990)), in round-bottomed 5-ml culture tubes (FALCON). Cells were stimulated with 1 μg/ml of PHA (REMEL) for 16 hours, then cultured in 24-well plates at a density of $1 \times 10^6$ for an additional 72 hours in the presence of 2-deoxy-5-azaC or 5-azaC(SIGMA-ALDRICH), procainamide (SIGMA-ALDRICH), hydralazine (SIGMA-ALDRICH), or the MEK inhibitors U0126 (PROMEGA) or PD98059 (PROMEGA). In other studies, PHA-stimulated PBMCs were cultured in RPMI 1640/10% FCS and treated with indomethacin, chloroquine, hydrocortisone, and 6-mercaptopurine (6-MP) (all from SIGMA-ALDRICH). TT48E, a cloned, CD4+, tetanus toxoid-reactive human T cell line, was cultured as previously described (Cornacchia et al., J Immunol 140, 2197 (1988); Richardson et al., Arthritis Rheum 35, 647 (1992)).

In other studies, T cells were isolated by negative selection using magnetic beads and instructions provided by the manufacturer (Pan T cell Isolation Kit, Miltenyi), and the CD4+ or CD8+ subset was similarly isolated by magnetic cell sorting. Jurkat cells (E6-1) were cultured as previously described (See, e.g., Cornacchia et al., J Immunol 140:2197 (1998)). Purified human CD4+ T cells were first stimulated with plate bound anti-CD3 and soluble anti-CD28. Briefly, 24 well plates were coated with 300 μl of anti-CD3 (10 μg/ml in PBS—SouthernBiotech) 18 hours 4° C., washed, then $2 \times 10^6$ purified T cells were added to the wells in 2 ml RPMI 1640/10% FCS containing 2 μg/ml anti-CD28 (SouthernBiotech). The plates were incubated 37° C. in a humidified atmosphere containing 5% $CO_2$ for 18-24 hours, then treated with 5 μm 5-azaC (ALDRICH), 50 μm Pca (SIGMA), 20 μm Hyd (ALDRICH), 40 μm U0126 (PROMEGA) or 25 μm PD98059 (PROMEGA), and cultured for 3 additional days as described (See, e.g., Oelke et al., Arthritis Rheum 50:1850 (2004)).

Oligonucleotide array analysis. Messenger RNA (mRNA) was isolated from untreated or 2-deoxy-5-azaC-treated T cells, and analyzed using AFFYMETRIX U95A oligonucleotide arrays (See, e.g., Lu et al., J Immunol 170, 5124 (2003)).

Real time reverse transcription-polymerase chain reaction (RT-PCR). CD70 transcripts were quantitated by real time RT-PCR using a LIGHTCYCLER(ROCHE) or a ROTOR-GENE 3000 (Corbett) according to previously published protocols (See, e.g., Lu et al., J Immunol 170, 5124 (2003); Oelke et al., Arthritis Rheum 50:1850 (2004)). CD70 mRNA levels were quantitated relative to β-actin transcripts (See, e.g., Lu et al., J Immunol 170, 5124 (2003)). The following primers were used: forward, 5'-TGCTTTGGTCCCATTGGTCG-3' (SEQ ID NO: 13) and reverse, 5'-TCCTGCTGAGGTCCT-GTGTGATTC-3' (SEQ ID NO: 14); β-actin forward: 5'-GGACTTCGAGCAAGAGATGG-3'(SEQ ID NO: 15), Reverse: 5'-AGCACTGTGTTGGCGTACAG (SEQ ID NO: 16).

Flow cytometric analysis. The following fluorochrome-conjugated monoclonal antibodies were obtained from BD PHARMINGEN (San Diego, Calif.): FITC-conjugated anti-human CD70, CD2, or isotype-matched controls; phycoerythrin (PE)—conjugated anti-CD2, CD4, and CD8; and CyChromeconjugated anti-HLA-DR, CD2, and isotype controls. Staining and multicolor flow cytometric analysis were performed (See, e.g., Hale et al., Cell Immunol 220, 51 (2002)) using saturating concentrations of antibody.

T cell and B cell costimulation assays. E-rosette—purified T cells were stimulated for 16 hours with PHA and then treated with the indicated chemicals for an additional 72 hours as described above. Where indicated, T cell subsets were isolated by negative selection using magnetic beads (Miltenyi). B cells ($1-4 \times 10^5$) enriched by negative selection using magnetic beads (Miltenyi) and assessed to be 70-85% pure using PE-conjugated anti-human CD21 (PHARMINGEN), were added to washed, drug-treated autologous T cells, at T cell to B cell ratios of 4:1, 2:1, 1:1, 1:2, and 1:4. Where indicated, 0.625 μg/ml of PWM (ALDRICH) was added. The cells were cultured in RPMI 1640/10% FBS/penicillin/streptomycin for 8 days in 96-well roundbottomed plates (Costar) containing a 200 μl total volume (performed in duplicate). Cells were supplemented with 50 μl of medium on day 4. Where indicated, 1 μg/ml of anti-CD70 monoclonal antibody (HNE51) (DAKO) was added to the cultures. TT48E cells were similarly stimulated with PHA (1 μg/ml) for 18 hours, treated with the indicated drugs for 3 days, then similarly cultured with autologous B cells for 8 days. Where indicated, the TT48E cells were pretreated with 1 μg/ml of anti-CD70 for 30 minutes at 4° C., then washed and added to the B cells, according to protocols described by others (See, e.g., Kobata et al., Proc Natl Acad Sci USA 92, 11249 (1995)).

CD4+ T cells were similarly isolated from lupus patients by first purifying the T cells by E-rosetting, then depleting the CD8+ T cells using magnetic beads (Miltenyi). These cells were then similarly cultured with purified autologous B cells. Where indicated, the T cells were pretreated with anti-CD70.

IgG enzyme-linked immunosorbent assays (ELISAs). IgG was measured in the supernatants of the T cell-B cell cultures (See, e.g., Richardson et al., Clin Immunol Immunopathol 55, 368 (1990)). Briefly, 96-well flatbottomed polystyrene plates (Costar) were coated with 1 μg/ml of goat anti-human IgG (Southern Biotech) and washed. Unreacted combining sites were sealed with 3% bovine serum albumin (BSA) in phosphate buffered saline (PBS) by incubation at 4° C. for 16 hours. Pooled supernatants from duplicate wells were diluted 1:5 in PBS/1% BSA, and 50 μl was added to the wells. Serial dilutions of purified human IgG (Sigma) were used for quantitation. Following incubation and washing, goat anti-human IgG conjugated with horseradish peroxidase (Southern Biotech) was added, and cells were incubated for 2 hours at room temperature. The wells were washed 3 times with PBS/0.1% Tween 20, and color was developed using Sigma Fast tablets. The plates were read at 405 nm using a SpectraMax spectrophotometer (Molecular Devices). All determinations were performed in quadruplicate.

Statistical analysis. The difference between means was tested by Student's unpaired t-test or ANOVA with post hoc testing using the Bonferroni correction. Power, regression analyses, and analysis of variance were performed using Systat 10 software (Richmond, Calif.).

Bisulfite sequencing. The putative CD70 promoter was identified using the published CD70 cDNA sequence and Tfsitescan software. Deoxycytosine (dC) and deoxymethylcytosine (d'''C) bases in the gene promoter and 5' flanking sequences were identified by bisulfite treatment of purified DNA followed by nested PCR amplification of 3 sequential fragments to span the entire region. The primers were designed to avoid CG pairs and to account for the conversion of dC to dU by the bisulfite. EcoRI sites were added to the forward primers, and XbaI to the reverse, to facilitate cloning. The amplified fragments were then cloned into PBS+, and 5 clones sequenced for each fragment. The primers used were:

Fragment 1:
  Round I:
    Forward Primer (−291~−256): SEQ ID NO: 1
    Reverse Primer (+400~+436): SEQ ID NO: 2
  Round II:
    Forward Primer (−211~−175): SEQ ID NO: 3
    Reverse Primer (−5~+29): SEQ ID NO: 4

Fragment 2:
  Round I:
    Forward Primer (−609~−580): SEQ ID NO: 5
    Reverse Primer (−278~−242): SEQ ID NO: 6
  Round II:
    Forward Primer (−581~−545): SEQ ID NO: 7
    Reverse Primer (−330~−288): SEQ ID NO: 8

Fragment 3:
  Round I:
    Forward Primer (−966~−931): SEQ ID NO: 9
    Reverse Primer (−543~−580): SEQ ID NO: 10
  Round II:
    Forward Primer (−956~−920): SEQ ID NO: 11
    Reverse Primer (−567~−603): SEQ ID NO: 12

Promoter characterization: A 1018 bp fragment containing the CD70 (TNFSF7) promoter and predicted transcription start site, identified using Tfsitescan software, was amplified from primary human CD4+ T cells by PCR using the following primers, numbered relative to the predicted transcription start site:

```
Forward (-966):
GCTCTCGAGGTGAAAACCCATCTCTAC        (SEQ ID NO: 17)

Reverse (+52):
TCCAAGCTTTCTACTTGCTTCAACCTG        (SEQ ID NO: 18)
```

The forward primer contains an XhoI site at the 5' end, and the reverse a HindIII site at the 3' end. The amplified fragment was cloned into pGL3-Basic, and sequenced by the University of Michigan DNA Sequencing Core to exclude Taq error.

TNFSF7 promoter constructs with 5' deletions were generated by PCR amplification of genomic DNA using the following forward primers:

```
F1(-966):
GCTCTCGAGGTGAAAACCCATCTCTAC        (SEQ ID NO: 17)

F2(-572):
CAGCTCGAGCAACATGGTGAAACC           (SEQ ID NO: 19)

F3(-321):
ATTCTCGAGTGTCTGCTGTATCC,           (SEQ ID NO: 20)
all with an XhoI site added.
```

In all cases the reverse primer was: TCCAAGCTTTC-TACTTGCTTCAACCTG (SEQ ID NO: 18) with a HindIII site added. These primer combinations generated fragments of 1018 bp (−966 to +52), 624 bp (−572 to +52), and 412 bp (−360 to +52), respectively. The promoter fragments were digested with XhoI and HindIII and inserted upstream of a luc reporter gene in the pGL3 vector (PROMEGA). The constructs were then transfected into Jurkat cells by electroporation using previously described protocols and a previously described β-galactosidase expression construct as control (See, e.g., Lu et al., Biol Proced Online 6:189 (2004)).

Patch methylation and transfections: The 1018 bp (−966 to +52) TNFSF7 gene promoter fragment, cloned into the luciferase-containing vector pGL3-Basic, was digested with the following restriction endonucleases:

Region 1 (−966 to −490): XhoI and NruI

Region 2 (−490 to −229): NruI and ApaI

Region 3 (−229 to +52): ApaI and HindIII

The 3 fragments were gel purified, methylated with SssI and S-adenosylmethionine (See, e.g., Lu et al., Biol Proced Online 6:189 (2004)), and then religated back into the reporter construct. Completeness of methylation was tested by digestion with NarI for regions 1 and 2, and EagI for region 3. Controls included a mock methylated construct, prepared by omitting the SssI. The methylated or mock methylated constructs were transfected into Jurkat cells by electroporation and expression measured relative to β-galactosidase controls (See, e.g., Lu et al., Biol Proced Online 6:189 (2004)).

Example 2

Identification of Methylation-Sensitive T Cell Genes

Oligonucleotide arrays were used to identify T cell genes affected by DNA methylation inhibition. Purified T cells were stimulated with PHA and treated with 2-deoxy-5-azaC as described in Materials and Methods. Three 3 days later, gene expression was compared in treated and untreated cells using oligonucleotide arrays. Overall, 118 genes reproducibly increased ≧2-fold, and 12 genes decreased ≧2-fold. In 2 independent experiments, CD70 expression increased 2.6±0.6-fold (mean±SEM) in treated cells relative to untreated controls (See FIG. 1A). These results were confirmed using real time RT-PCR to compare CD70 mRNA levels in untreated cells and cells treated with 5-azaC and the ERK pathway inhibitor U0126. U0126 inhibits DNA methylation by decreasing levels of DNA methyltransferase 1 (Dnmt1) and Dnmt3a (See, e.g., Deng et al., Arthritis Rheum 48, 746 (2003)). Both drugs increased the expression of CD70 mRNA relative to that of beta-actin (See FIG. 1B).

Example 3

Comparison of DNA Methylation Inhibitors on CD70 Expression

The effects of DNA methylation inhibitors on T cell CD70 expression were further confirmed by treating T cells with a panel of DNA methylation inhibitors and measuring CD70 by flow cytometry. The panel of inhibitors used included 5-azaC, an irreversible DNA methyltransferase inhibitor (See, e.g., Glover and Leyland-Jones, Cancer Treat Rep 71, 959 (1987)) procainamide, a competitive DNA methyltransferase inhibitor (See e.g., Scheinbart et al., J Rheumatol 18, 530 (1991)), and the ERK pathway inhibitors PD98059, U0126, and hydralazine. Kinetic analyses performed by flow cytometry on days 1, 3, 5, and 7 after treatment with all 5 drugs demonstrated that the increase in CD70 expression was maximal at 3 days after treatment. Histograms represent the CD70 expression in untreated, PHA-stimulated T cells (See FIG. 2A, filled histogram) and in T cells treated with 1 μM 5-azaC for 3 days (See FIG. 2A, open histograms). A small increase is observable. The effect of a range of 5-azaC concentrations on CD70 expression was also tested, with 1 μM producing the greatest effect (P=0.001 overall by analysis of variance; n=5 experiments) (See FIG. 2B). The relatively small magnitude of the change probably reflects the fact that 5-azaC has significant toxicities (See, e.g., Glover and Leyland-Jones, Cancer Treat Rep 71, 959 (1987)). Histograms depict the CD70 expression on untreated T cells (See FIG. 2C, solid histogram) and T cells treated with 20 μM procainamide (See FIG. 2C, open histogram) and an increase in the ratio of the mean fluorescence intensity (MFI) of CD70 expression with increase dosage of procainamide (See FIG. 2D) (P=0.032; n=6 experiments).

Figure 2:
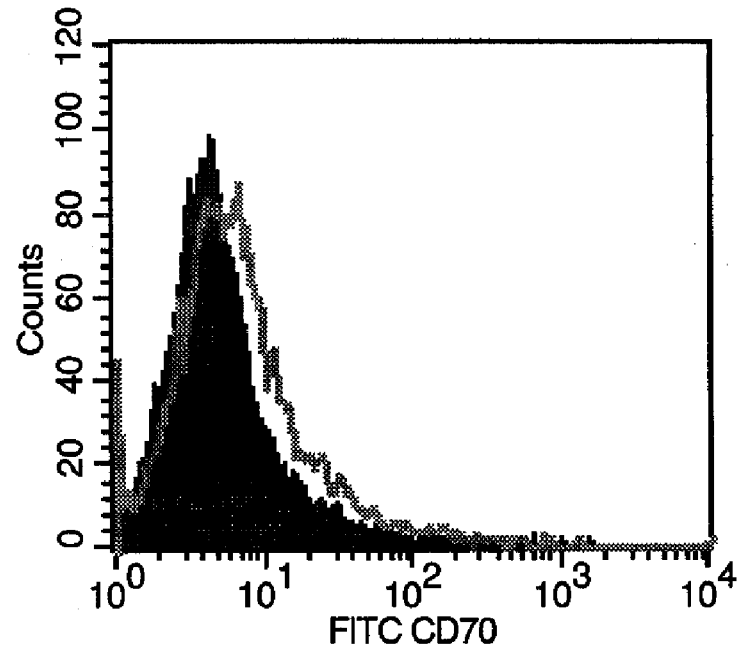
FIG. 2 shows increased CD70 expression induced by DNA methylation inhibitors.
Figure 2:
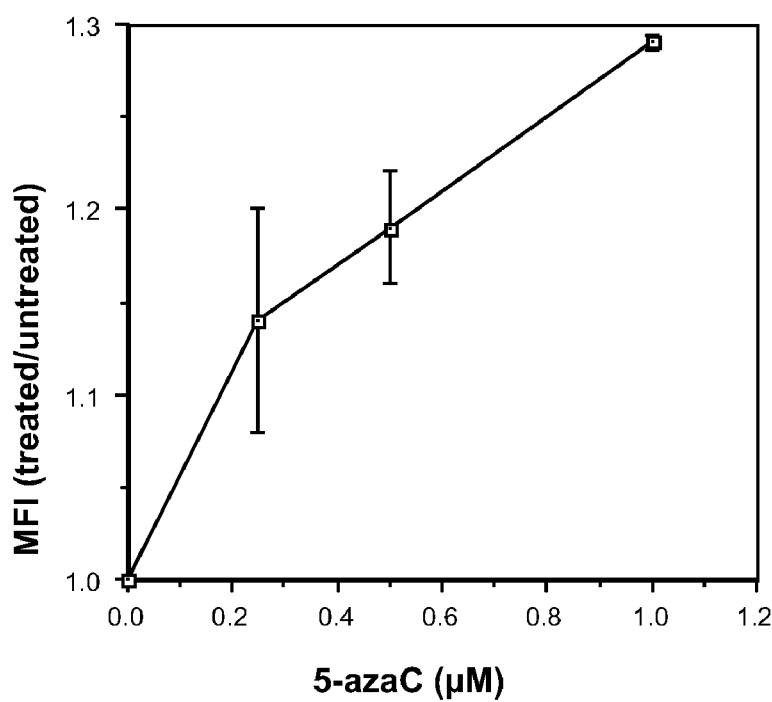
Figure 2:
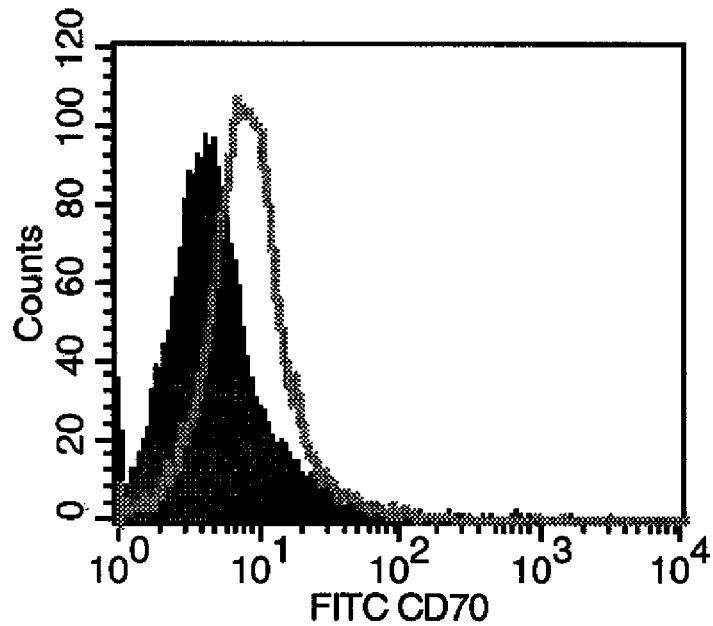
Figure 2:
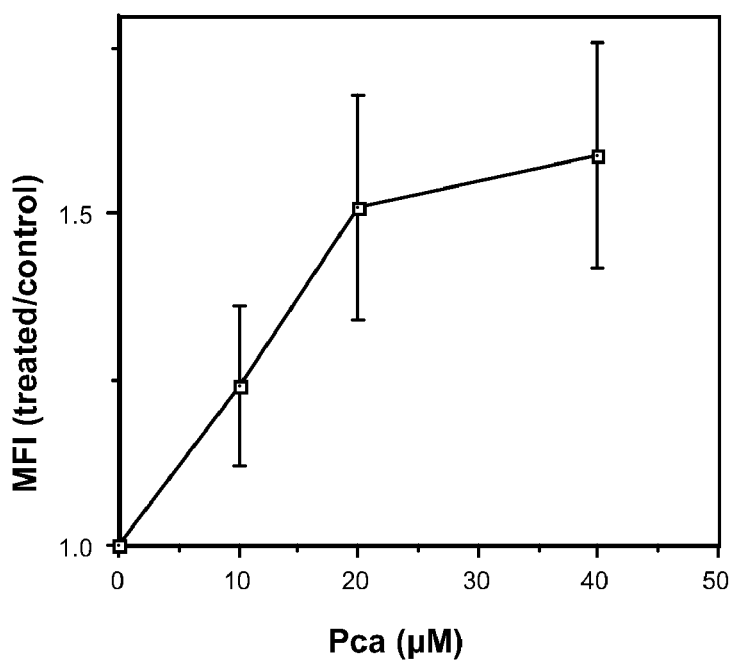
Figure 2:
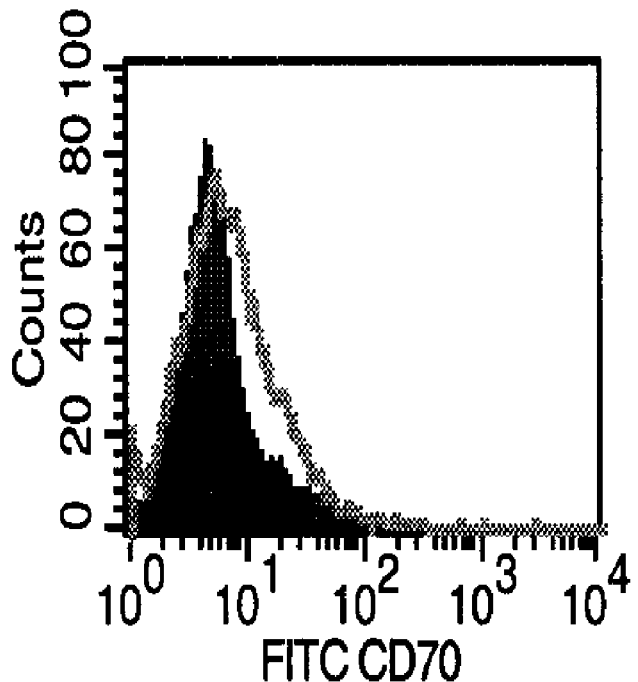
Figure 2:
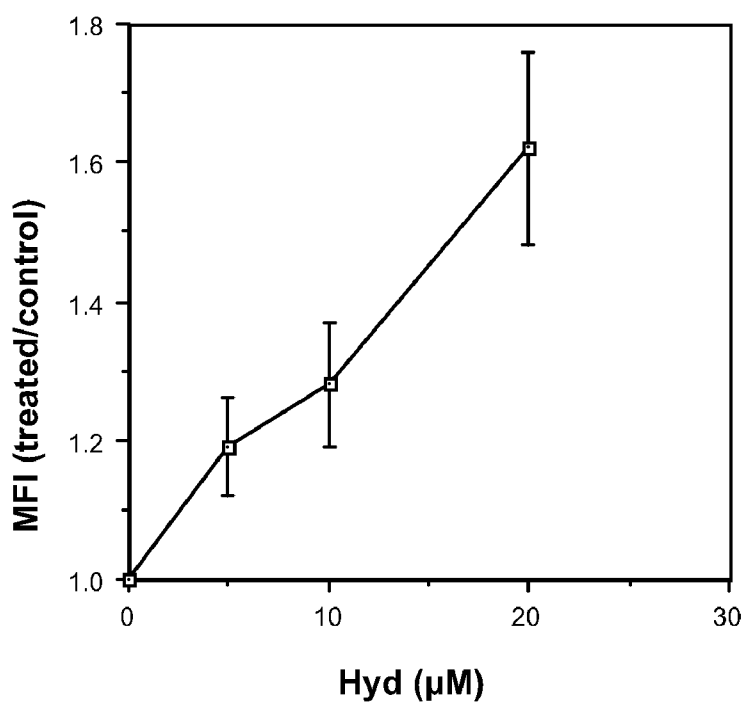
Figure 2:
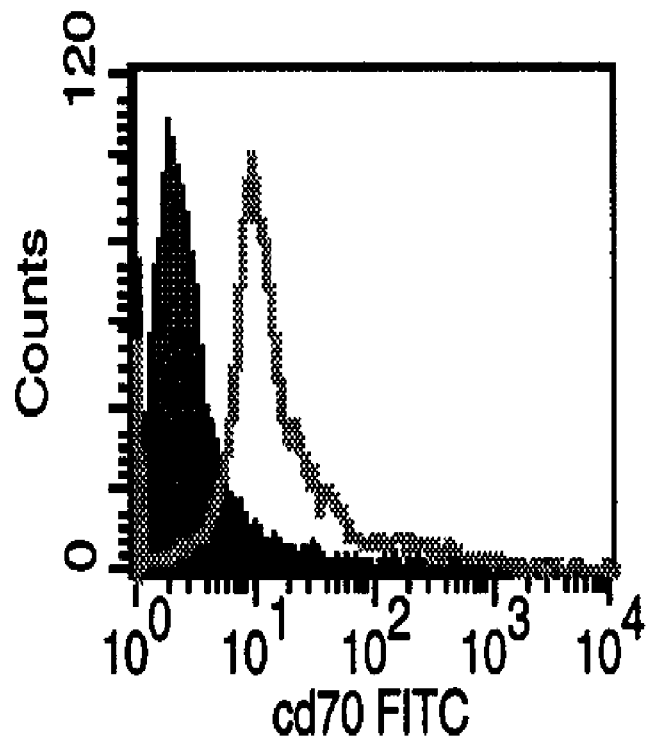
Figure 2:
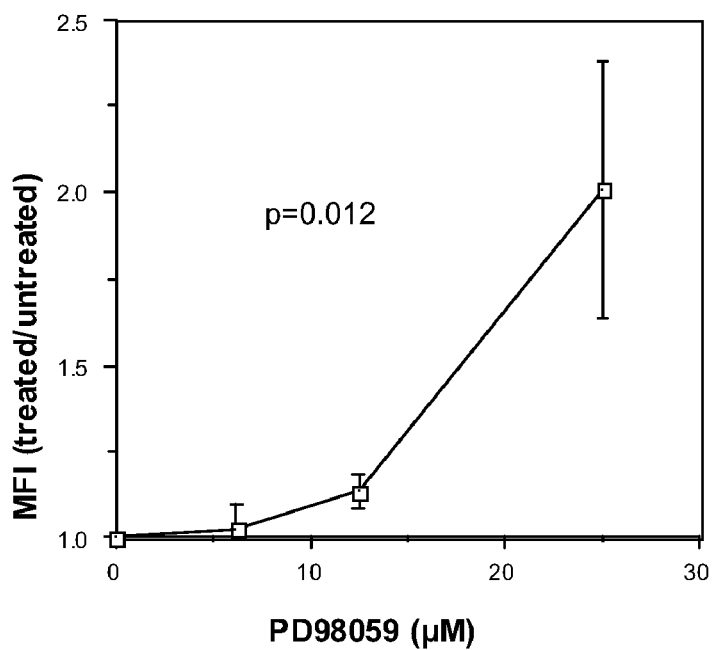
Figure 2:
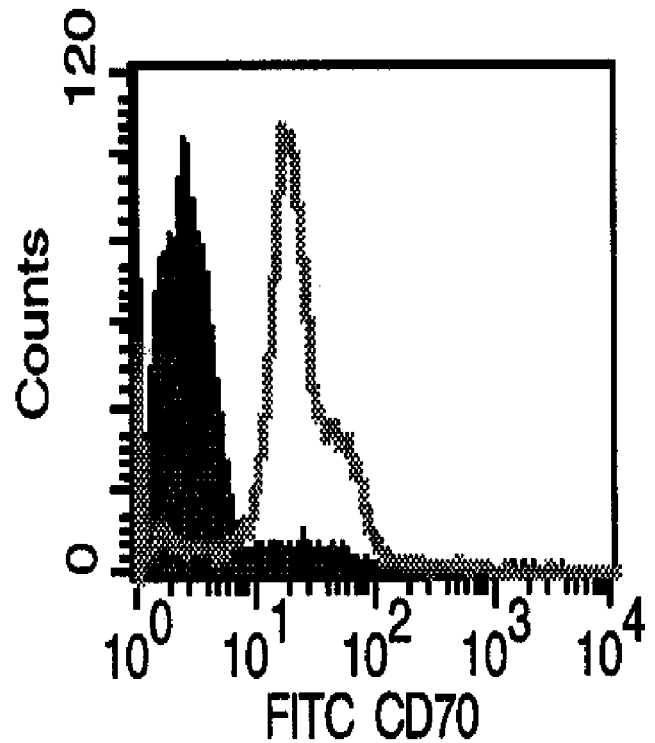
Figure 2:
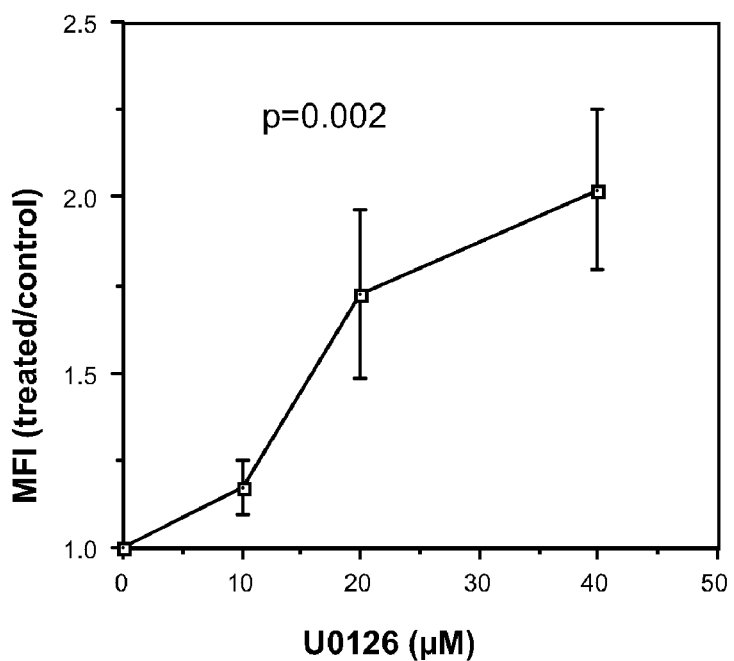

Similarly, histograms represent CD 70 expression on untreated (FIG. 2E, filled histogram) versus T cells treated with 20 μM hydralazine (FIG. 2E, open histogram). A dose-response curve using increasing concentrations of hydralazine is shown (FIG. 2F, P=0.003, n=6). CD70 expression on untreated T cells (FIG. 2G., filled histogram) versus T cells treated with 25 μM PD98059 (FIG. 2G, open histogram) and a dose response curve using increasing concentrations of PD98059 (FIG. 2H, P=0.012; n=5) demonstrate an increase in CD70 expression with treatment. The expression of CD70 on untreated T cells (FIG. 2I, filled histogram) and T cells treated with 40 μM U0126 (FIG. 2I, open histogram), and the dose-response curve using increasing amounts of U0126 (FIG. 2J, P=0.002; n=5) demonstrate an increase in CD70 expression with treatment. In this series of experiments, there was no significant difference in the maximum increase caused by the DNA methyltransferase inhibitor procainamide and the ERK pathway inhibitors PD98059 and U0126.

Studies were performed examining the effects of the DNA methylation inhibitors on CD70 expression in CD4+ and CD8+ T cell subsets. 1 μM 5-azaC increased CD70 MFI on CD4+ T cells by 1.53±0.45-fold (P=0.025; n=5 experiments), 25 μM PD98059 increased the MFI by 1.63±0.43-fold (P=0.032; n=3), and 40 μM U0126 increased the MFI by 3.20±0.44-fold (P=0.039; n=4). In contrast to the CD4+ population, the increase in CD70 MFI was smaller on CD8+ T cells and did not reach statistical significance for any of the drugs tested. However, this smaller increase may account for the suggestion of 2 populations seen in T cells treated with U0126 (FIG. 2I, where CD70 MFI increased 2.83±0.95-fold (P=0.085)). This also most likely accounts for the greater increase in expression observed on the CD4+ population relative to the polyclonal cells, particularly for the cells treated with U0126.

It was possible that the drug treatments selected for overgrowth or survival of a T cell subset that overexpressed CD70. To exclude this possibility, the cloned human tetanus toxoid-reactive T cell clone TT48E was treated with 1 μM 5-azaC and 40 μM U0126 for 3 days as above. In 6 serial experiments, CD70 expression increased 1.69±0.33-fold (P=0.048) on the 5-azaC-treated cells and 1.87±0.37-fold (P=0.004) on the U0126-treated cells. This is evidence against subset selection by the drug treatment. The smaller increase observed in the U0126-treated cloned cells relative to the uncloned cells may reflect differences between the cloned line and primary polyclonal cells.

Example 4

Effect of DNA Methylation Inhibitors on CD70-Dependent B Cell Help

Since CD70 participates in T cell-dependent B cell stimulation (See e.g., Kobata et al., Proc Natl Acad Sci USA 92, 11249 (1995)), the effects of DNA methylation inhibitors on CD70-dependent B cell help were examined. Unfractionated T cells were stimulated with PHA, treated with 5-azaC or U0126 as above, and 3 days later, the treated cells were cultured with PWM and varying numbers of autologous B cells, with and without anti-CD70. Eight days later, total IgG in the supernatants was measured by ELISA. Optimal results were routinely observed at T cell to B cell ratios of 1:4 (see below). B cells cultured with 5-azaC-treated T cells and with U0126-treated T cells secreted greater amounts of IgG than did B cells cultured with the same numbers of untreated T cells (P<0.05) (See, e.g., FIG. 3). This finding is consistent with earlier reports that increasing the CD70 expression by transfection increases B cell IgG production in similar systems (See e.g., Kobata et al., Proc Natl Acad Sci USA 92, 11249 (1995)). Furthermore, the addition of anti-CD70 decreased IgG production by the treated cells (P<0.05). A suppressive effect of anti-CD70 on B cells was unlikely, because stimulating purified B cells with lipopolysaccharide (LPS) then adding the same amount of anti-CD70 yielded no significant inhibition of IgG synthesis (B cells plus LPS 136±9 μg/ml and B cells plus LPS and anti-CD70 125±8 μg/ml).

These results were confirmed using the cloned, CD4+, tetanus toxoid-reactive human T cell line TT48E. The T cells were again treated for 3 days with 5-azaC or U0126. To further exclude the possibility that anti-CD70 interacted with CD70 on B cells, the T cells were pretreated with anti-CD70 for 30 minutes at 4° C., washed, and then cultured with autologous B cells. Since reports indicate T cells treated with DNA methylation inhibitors also induce T cell autoreactivity and that the autoreactive cells can directly stimulate B cell IgG secretion (See e.g., Richardson et al., Clin Immunol Immunopathol 55, 368 (1990)), these studies were performed without the addition of PWM. The cloned T cells treated with either 5-azaC or U0126 induced B cells produce greater amounts of IgG than did untreated T cells (FIG. 4, P<0.05). Furthermore, pretreatment of the T cells with anti-CD70 decreased IgG synthesis, indicating a direct effect on T cells (FIG. 4).

Example 5

Overexpression of CD70 on T Cells from Patients with Active Lupus

T cells from patients with active lupus have decreased levels of total genomic dmC (See e.g., Richardson et al., Arthritis Rheum 33, 1665 (1990)), and the same CD11a and perforin sequences demethylate in lupus T cells as in T cells treated with 5-azaC (See e.g., Kaplan et all Arthritis Rheum 46, S282 (2002); Lu et al., Arthritis Rheum 46, 1282 (2002)). It was therefore sought to be determined whether CD70 is also overexpressed on lupus T cells. Histograms show CD70 expression on T cells from a patient with active lupus (Lupus) (SLEDAI score 12) and a matched control subject (C) (FIG. 5A). CD70 expression on PHA-stimulated normal T cells with (dark histogram) and without (light histogram) U0126 treatment is also shown (FIG. 5B). A similar pattern of overexpression was seen in lupus T cells as in the drug-treated T cells. The percentage of peripheral blood T lymphocytes expressing CD70 in 11 patients with active lupus and 11 healthy controls is compared (FIG. 5C). Significantly more T cells from lupus patients expressed CD70 (P=0.047). CD70 expression on CD4+ and CD8+ T cells from normal controls and lupus patients was also compared. Significantly more CD4+ T cells from the lupus patients expressed CD70 than did those from the controls (P<0.05), and relatively few CD8+ T cells expressed CD70 (FIG. 5D).

Since T cell DNA methylation decreases in proportion to lupus disease activity, we determined whether disease activity affects T cell CD70 expression. To minimize inter-experimental variability, each lupus patient was paired with an age-, sex-, and race-matched control subject for this analysis. The ratio of the CD70 MFI on T cells from lupus patients and controls was determined and plotted against disease activity, as determined by the SLEDAI (FIG. 5E). The increase in CD70 expression was directly related to disease activity (P=0.036 by regression analysis). We similarly studied 3 patients with inactive lupus (SLEDAI score 2, 0, and 0, respectively). The CD70 MFI ratio in patients and controls was 0.94±0.05, indicating no overexpression in patients with inactive disease.

Since CD70 is preferentially expressed on activated T cells (See e.g., Lens et al., Semin Immunol 10, 491 (1998)) and since T cells from patients with active lupus are frequently activated (See e.g., Yu et al., J Exp Med 152 89s (1980)), it was determined whether CD70 expression on T cells from patients with active lupus reflected T cell activation. Purified T cells from 4 patients with active lupus (Table 1: patients 7, 8, 10, and 11) and 4 control subjects were stained with anti-HLA-DR and anti-CD70 and analyzed by flow cytometry. CD70 was preferentially expressed on HLA-DR-negative lupus patients' T cells (FIG. 5F, P<0.05). Using the data shown in FIG. 5F, an unpaired t-test, and alpha level of 0.05, as few as 2 subjects per group would give 90% power to detect a difference in CD70 expression on HLA-DR-negative T cells. The CD70 overexpression on T cells lacking activation markers is similar to the overexpression of LFA-1 and perforin on T cells (See e.g., Kaplan et all Arthritis Rheum 46, S282 (2002)) and suggests that mechanisms other than T cell activation likely contribute to CD70 overexpression.

The possibility existed that higher immunosuppression might contribute to this finding. However, the patients were taking different combinations of immunosuppressive agents, which does not support this possibility. Still, many of the patients were receiving prednisone. Therefore, CD70 expression on CD4+ T cells from 3 patients receiving prednisone and various cytotoxic agents but with autoimmune diseases other than lupus (Table 1) and 3 matched healthy controls were analyzed. No increase in CD70 was seen (0.59±0.29% CD4+, CD70+ cells in patients versus 0.65±0.51% in controls). To further exclude this possibility, PBMCs were stimulated with PHA, then stimulated and unstimulated cells were cultured for 24 hours in the presence or absence of graded concentrations (1-100 µM) of medications representative of the classes commonly used to treat lupus and not requiring metabolism for activation. These included indomethacin (for nonsteroidal antiinflammatory drugs), chloroquine (for antimalarials), hydrocortisone. (for steroids), and 6-MP (for azathioprine). CD70 and CD4 expression were then measured by flow cytometry. No increase in CD70 expression was seen on stimulated or unstimulated CD4+ cells. Thus, other mechanisms, such as DNA hypomethylation, could play a role.

Example 6

Contribution of CD70 to B Cell Activation by Lupus T Cells

To determine if CD70 overexpression on lupus T cells could contribute to B cell activation similar to T cells demethylated with 5-azaC or U0126, T cells from 3 patients with active lupus and 3 healthy controls were treated with anti-CD70 for 30 minutes at 4° C. as above, then cultured for 8 days with purified autologous B cells at varying T cell to B cell ratios without PWM. At all ratios tested, lupus T cells stimulated IgG synthesis significantly better (P<0.05) than controls and that a T cell:B cell ratio of 1:4 resulted in optimal B cell activation (FIG. 6). Using the results shown for a T cell:B cell ratio of 1:4, an unpaired t-test, and alpha level of 0.05, there was 94% power to detect a difference between the lupus patients and controls with 3 subjects per group. Furthermore, anti-CD70 significantly decreased (P<0.05) IgG production to levels that were not significantly different from those in controls at all cell ratios tested, similar to the results in experimentally hypomethylated T cells (See FIGS. 3 and 4).

Example 7

Figure 7:
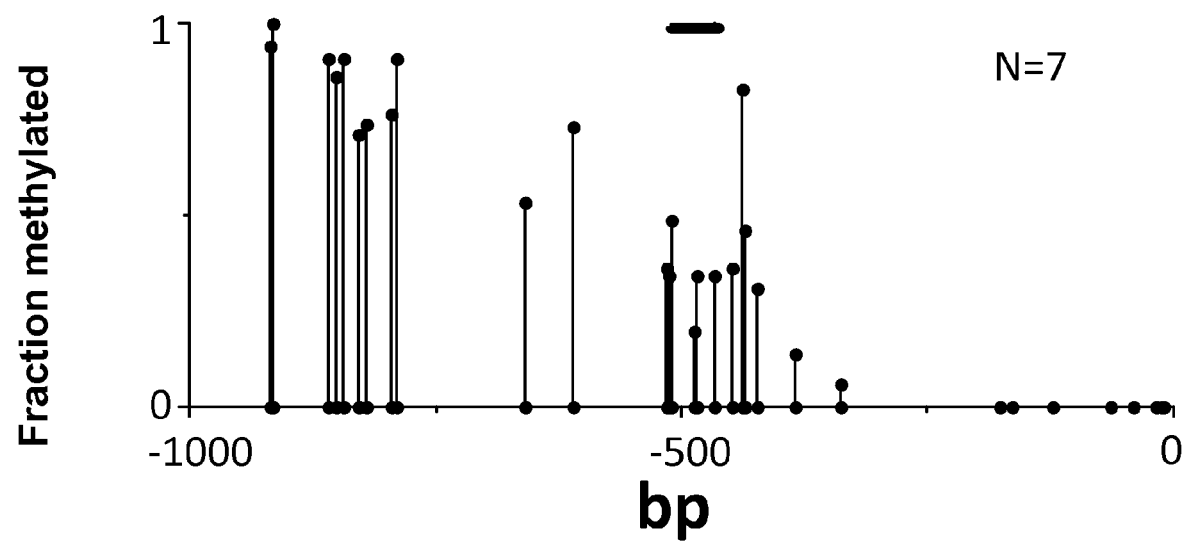
FIG. 7 shows methylation status of the CD70 promoter in CD4+ T cells.

Demethylation of Promoter Regulatory Elements Contributes to CD70 Overexpression in CD4+ Lupus T Cells Demethylation of promoter regulatory elements contributes to CD70 overexpression in CD4+ lupus T cells. DNA was isolated from the CD4+ T cells of 7 healthy individuals, bisulfite treated, and 1000 bp 5' to the putative CD70 transcription start site (as determined by Tfsitescan) was amplified by PCR. For each individual, 5 fragments were cloned and sequenced. Each dot on the X axis represents a potentially methylatable CG pair, and the Y axis represents the average methylation of the 35 determinations for each point (FIG. 7). The horizontal bar identifies a region containing 6 CG pairs that is demethylated by methylation inhibitors and in lupus (FIG. 7).

The effect of lupus and DNA methylation inhibitors on a regulatory element in the CD70 promoter was examined. DNA was isolated from the CD4+ T cells of 7 healthy individuals or 6 lupus patients, bisulfite treated, the region from −466--515, containing 6 CG pairs was amplified by PCR, and 5 fragments sequenced from each individual. The average methylation status of the 6 CG pairs for healthy versus lupus individuals is shown (FIG. 8, NI and Lupus, respectively). CD4+ T cells from 5 individuals were also stimulated with PHA, treated with the irreversible DNA methyltransferase inhibitor 5-azacytidine (5-azaC), and the methylation status of the 6 CG pairs similarly analyzed from the 25 fragments sequenced (FIG. 8, 5-azaC). PHA stimulation has no effect on the methylation status of this region. Similar studies were performed on stimulated T cells treated with the MEK inhibitor PD98059 (3 donors, 15 fragments), the competitive DNA methyltransferase inhibitor procainamide (Pca, 4 donors, 20 fragments), the ERK pathway inhibitor hydralazine (Hyd, 3 donors, 15 fragments), or the MEK inhibitor U0126 (2 donors, 10 fragments) (FIG. 8, Pca, Hyd, U0126 and PD85059, respectively). Results are presented as the mean±SEM of the average methylation of the 6 CG pairs, measured from the 10-35 determinations/group. Lupus T cells, T cells treated with the lupus inducing drugs Pca and Hyd, and T cells treated with either DNA methyltransferase inhibitors or ERK pathway inhibitors, all demethylate this region (FIG. 8).

Experiments conducted during the development of the present invention also demonstrated that DNA methylation inhibitors increased CD11c expression 6.8-fold as measured by mRNA level.

Example 8

Effect of DNA Methylation Inhibitors on CD70 mRNA

Figure 9:
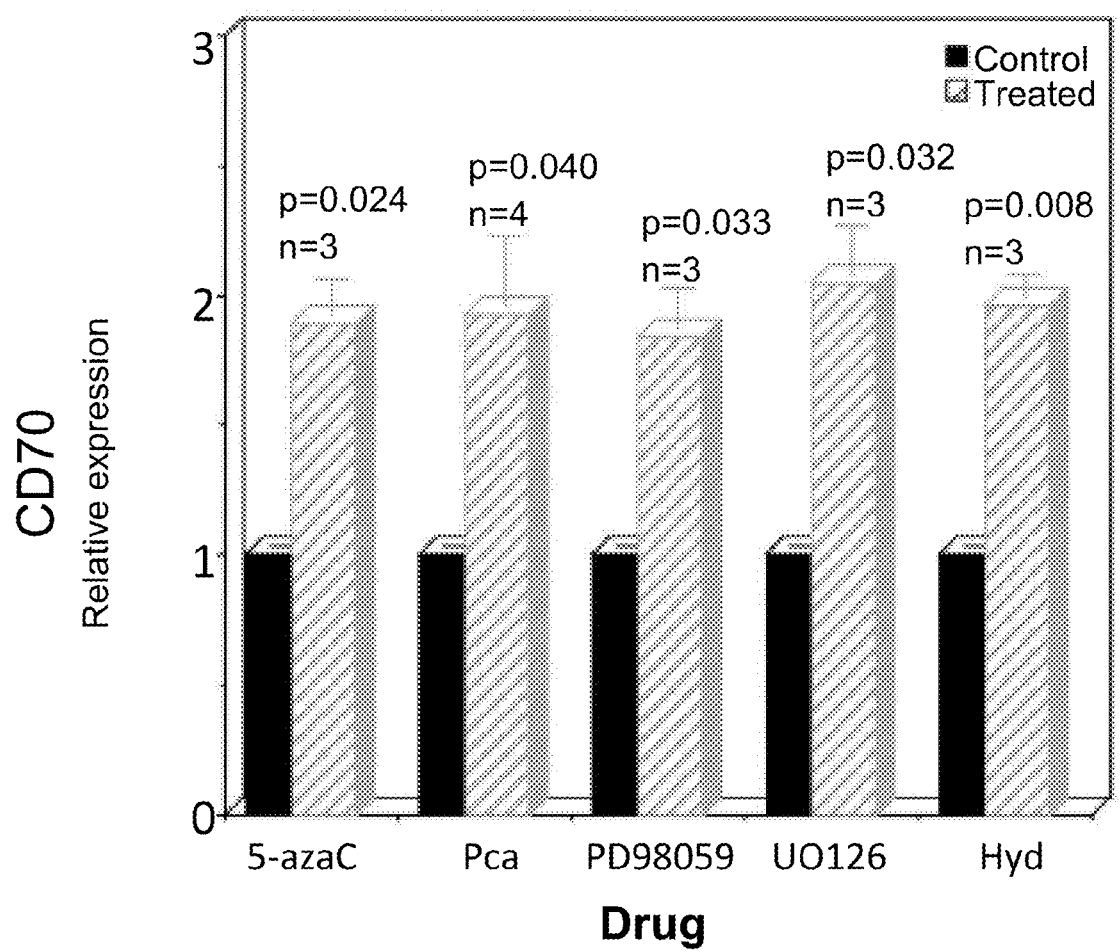
FIG. 9. shows Dnmt and ERK pathway inhibitors increase CD70 mRNA in CD4+ T cells.

Studies conducted during the development of the present invention demonstrated that 5-azaC, Pca, Hyd, U0126, and PD98059 increased CD70 expression on CD4+ T cells (See, e.g., Example 7). Thus, studies were also performed to determine if CD70 mRNA levels increased as well. Maintenance DNA methylation is a post-synthetic event (See, e.g., Attwood et al., Cell Mol Life Sci 59:241 (2002)), and Dnmt inhibitors must be present during S phase to inhibit methylation of the daughter cells. CD4+ T cells were stimulated with anti-CD3+ anti-CD28 and 18-24 hours later treated with the indicated Dnmt inhibitors (5 μm 5-azaC or 50 μm Pca) and ERK pathway inhibitors (20 μm Hyd, 40 μm U0126 or 25 μm PD98059) for 3 days. 3 days later CD70 transcripts were measured in untreated (See, e.g., FIG. 9 black bars) and treated (FIG. 9 crosshatched bars) cells relative to β-actin by real time RT-PCR. Results are present the mean±SEM of the indicated number of repeats, normalized to the untreated control. Each of these drugs increase CD70 transcripts (See, e.g., FIG. 9).

Example 9

Characterization of the CD70 Promoter

It was next determined if the 5 DNA methylation inhibitors affect the same regulatory sequences. The CD70 (TNFSF7) promoter has not been characterized, but the TNFSF7 genomic sequence is available from the human genome database (See, e.g., NCBI accession number NT 011255). Provided in FIG. 10 is a graphic representation of the TNFSF7 promoter with the locations of the potentially methylatable CG pairs, start site, CAAT boxes and putative transcription factor binding motifs indicated (filled circles represent the potentially methylatable CG pairs, and the broken arrow the putative transcription start site, with the locations of potential transcription factor binding sites and CAAT boxes also shown).

Promoter activity was then tested. A 1018 bp fragment (−996 to +52) containing the putative transcription start site was amplified by PCR, verified by sequencing, then cloned into pGL3-Basic. The construct or the pGL3 vector without insert were then transfected into Jurkat cells by electroporation using β-galactosidase as a control. The results are presented relative to β-galactosidase, and represent the mean±SEM of 4 independent experiments (See, e.g., FIG. 11) FIG. 11A presents data demonstrating that the TNFSF7 fragment has promoter activity (p=0.02 by t-test). Two 5' truncated fragments were similarly generated by PCR, and the entire fragment (−966 to +52) or the truncated mutants (−572 to +52 and −360 to +52) were transfected into Jurkat cells (FIG. 11B). The first 321 bp 5' to the predicted start site has promoter activity essentially identical to the longer fragments, suggesting that the majority of the promoter activity is located within this region.

Example 10

Methylation Patterns of the CD70 Promoter and 5' Flanking Region

Figure 12:
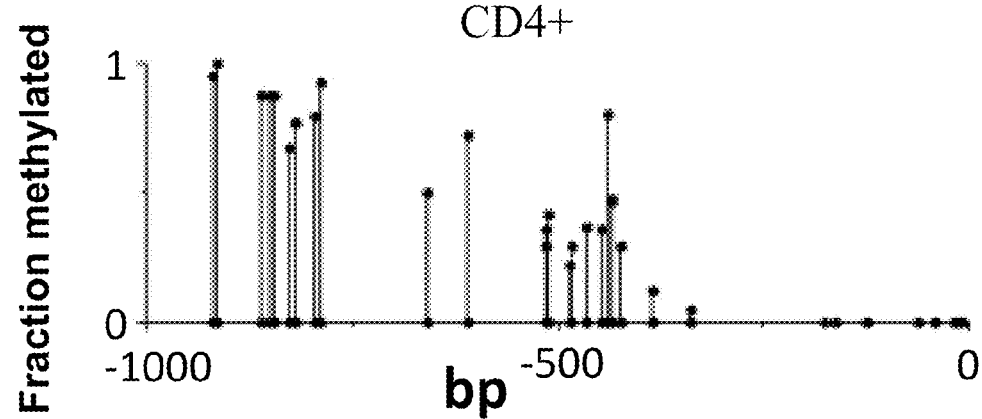
FIG. 12 shows CD70 promoter methylation patterns in CD4+ and CD8+ T cells. (A) CD4+ T cells. (B) CD8+ T cells.
Figure 12:
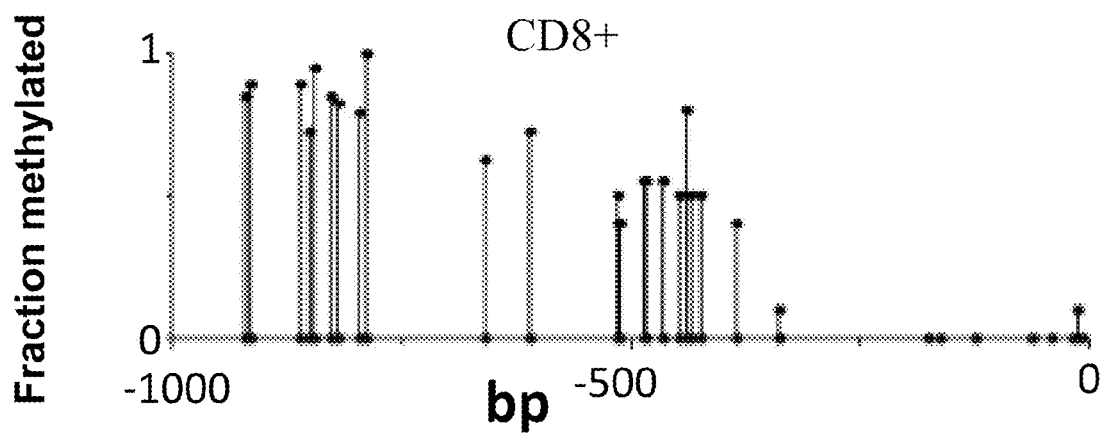
Figure 13:
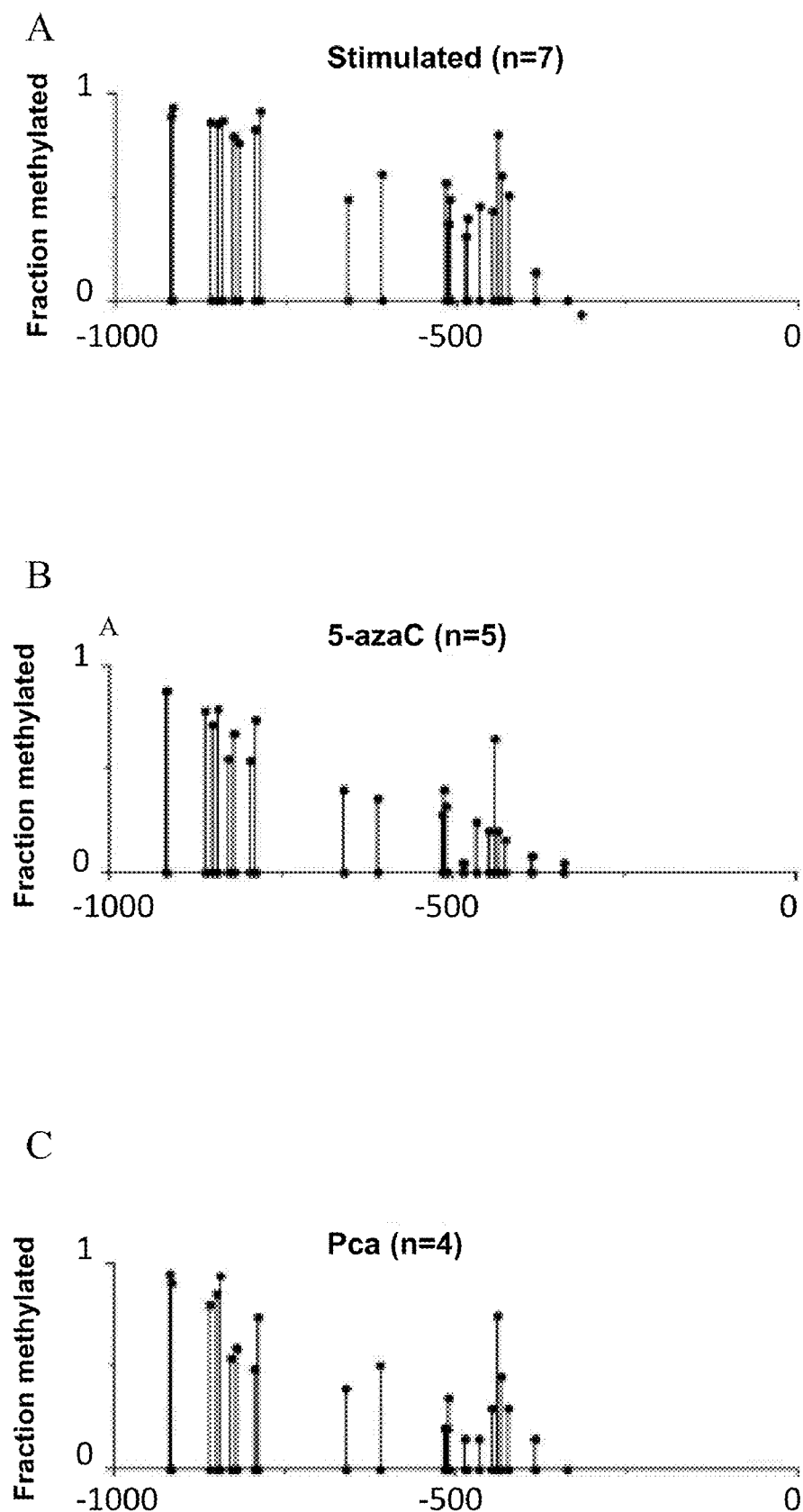
FIG. 13. shows CD70 promoter methylation patterns in CD4+ T cells treated with DNA methylation inhibitors: (A) non-treated controls; (B) 5-azaC; (C) Pca; (D) U0126; (E) PD98059; and (F) Hyd.
Figure 13:
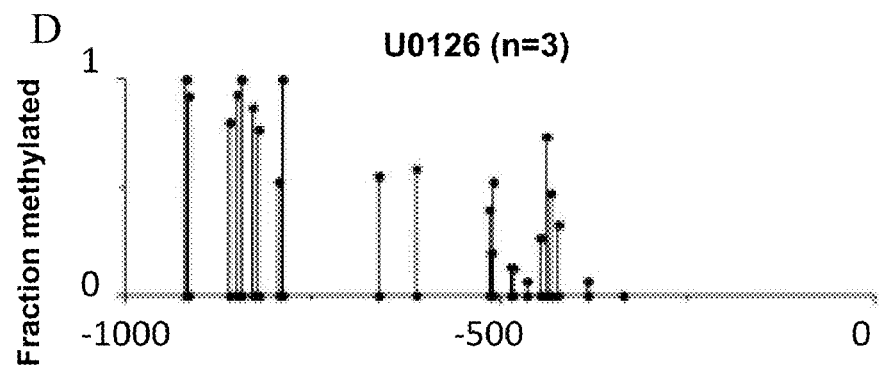
Figure 13:
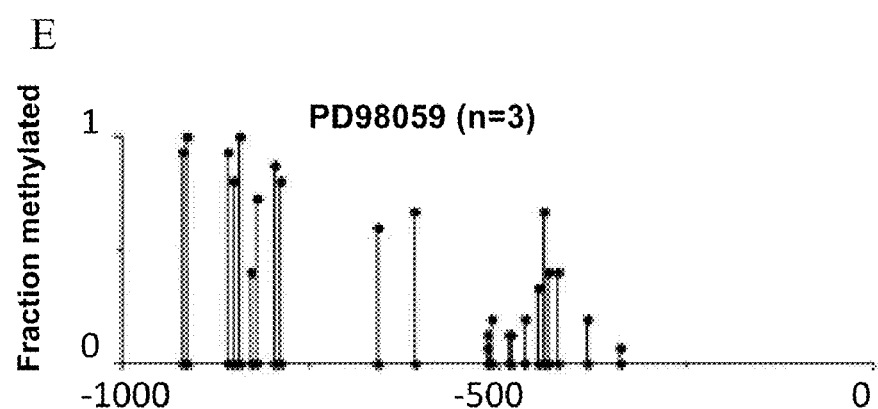
Figure 13:
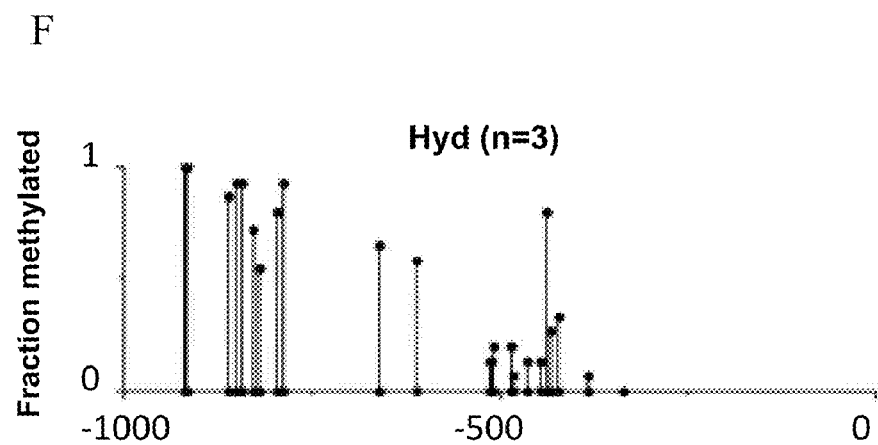

The methylation status of the CD70 (TNFSF7) promoter was then analyzed (See, e.g., FIG. 12). CD4+ and CD8+ T cells were isolated from the peripheral blood of healthy subjects, DNA isolated, treated with bisulfite, then the region shown in FIG. 10 was amplified in 3 sequential fragments as described in Materials and Methods. Briefly, DNA was isolated from primary CD4+ T cells of healthy volunteers, treated with sodium bisulfite, the region shown in FIG. 10 amplified by PCR in 3 sequential fragments, cloned, and 5 clones from each amplified fragment were sequenced for each donor. The dots on the X axis represent the location of each CG pair, and the dot above represents the mean fraction that is methylated.

The amplified fragments were cloned and 5 clones sequenced from each amplified fragment from each subject. FIG. 12A shows the average methylation of each of the 32 CG pairs in CD4+ T cells from 4 donors (bp −211 to +29) or 8 donors (bp −956 to −288), thus representing a total of 20-40 determinations per CG pair. FIG. 12B shows a similar analysis of the same region in CD8+ T cells from 4 healthy donors, representing 20 determinations for each CG pair. In both subsets, the region from the transcription start site to −300, corresponding to the region with promoter activity (FIG. 11B), is nearly completely demethylated, consistent with an active gene. The region from −−400 to −700 is partially methylated, while the more distal region (−750 to −1000) is nearly completely methylated. Although there appears to be a small decrease in methylation in the region from −515 to −300 in CD4+ T cells, the average methylation in this region was not significantly different from CD8+ T cells (p=0.175), and overall, the pattern of methylation in CD4+ and CD8+ T cells is essentially the same.

Example 11

Effect of DNA Methylation Inhibitors on CD70 Promoter Methylation

Figure 14:
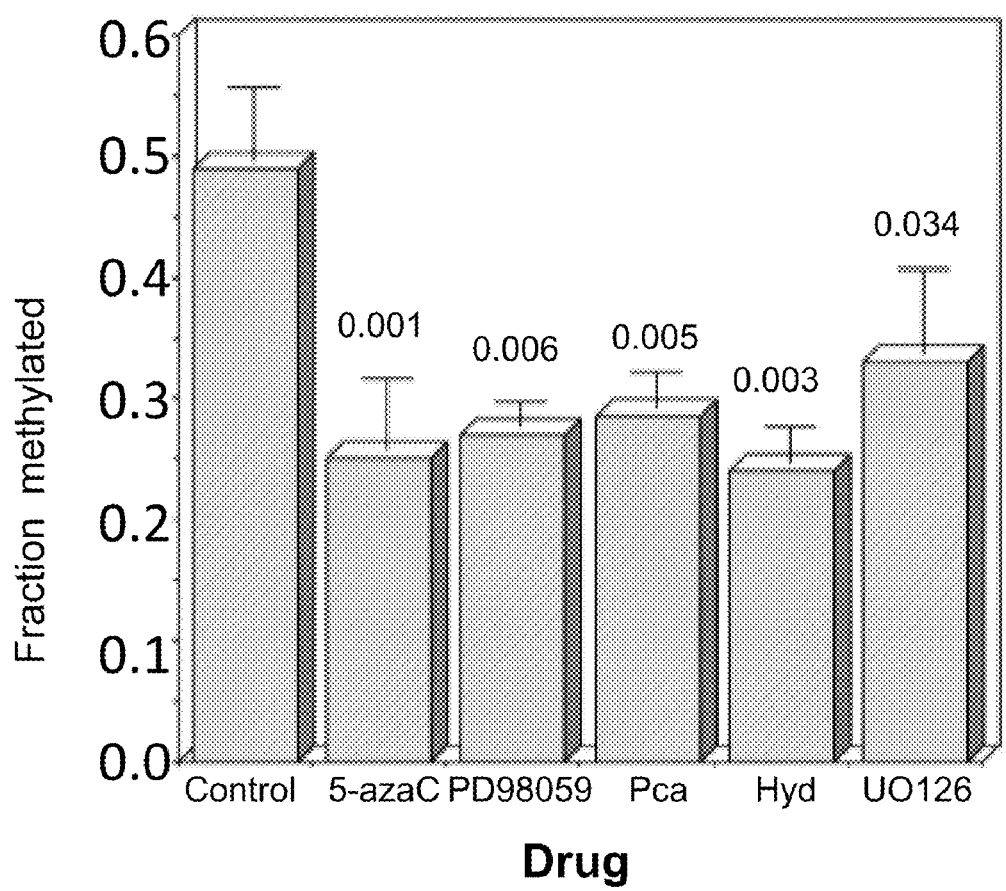
FIG. 14 shows the average methylation of the −515 to −423 sequence affected by treatment with DNA methylation inhibitors.

The effects of the DNA methylation inhibitors on the methylation status of this region were then compared. FIG. 13A shows the average methylation of each CG pair in the methylated region (−956 to −288) in CD4+ T cells from 7 healthy controls stimulated with anti-CD3 and anti-CD28. Again, 5 cloned fragments were sequenced from each control, for a total of 35 determinations per CG pair. Compared to FIG. 12, stimulation has no significant effect on the methylation status of this region, consistent with the effects of stimulation on other T cell genes like ITGAL and PRF1 (See, e.g., Lu et al., Arthritis Rheum 46:1282 (2002); Lu et al., J Immunol 170:5124 (2003)). FIG. 13B shows the effect of 5-azaC on the methylation pattern of the same region in stimulated CD4+ cells from 5 healthy donors. The 10 CG pairs in the region between −515 and −423 are hypomethylated compared to controls (FIG. 12A). The same region appears to demethylate in T cells treated with Pca (FIG. 13C), U0126 (FIG. 13D), PD98059 (FIG. 13E), and Hyd (FIG. 13F). FIG. 14 compares the average methylation for the 10 CG pairs (−515 to −423) in the T cells treated with DNA methylation inhibitors relative to stimulated, untreated controls. All 5 methylation inhibitors, whether signaling inhibitors or Dnmt inhibitors, significantly decrease the overall methylation of this region.

Example 12

Effect of Methylation on CD70 Promoter Function

Figure 15:
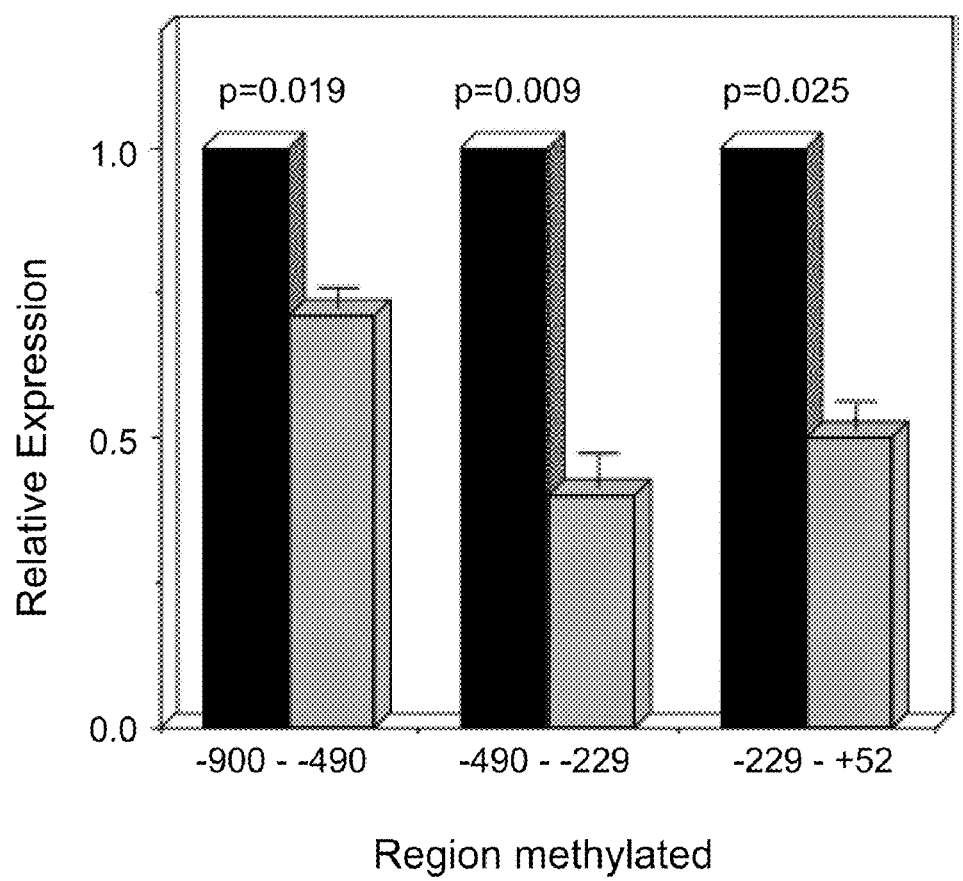
FIG. 15 shows the effect of regional methylation on TNFSF7 promoter function.

The transcriptional relevance of the methylation changes was determined using regional or "patch" methylation (See, Example 1). The 1018 bp promoter fragment was cloned into pGL3-Basic, then the regions from −996 to −490, −490 to −229, or −229 to +52 were individually excised, methylated in vitro with SssI and S-adenosylmethionine, ligated back into the expression construct, and transfected into Jurkat cells. Controls included β-galactosidase transfection controls as well as mock methylated constructs, similarly generated but omitting the SssI. The results are shown in FIG. 15. Results (gray bars) are normalized to paired mock methylated controls (black bars) similarly generated but omitting the SssI, and represent the mean±SEM of 3 independent experiments. Statistical analysis was by paired t-test, methylated vs mock methylated.

Methylation of each fragment suppressed promoter function relative to mock methylated controls (p=0.019, by paired t-test for −996 to −490, p=0.009 for −490 to −229, and p=0.025 for −229 to +52). However, methylation of the region from −490 to −229, which was affected by the methylation inhibitors, inhibits promoter function to a greater extent than does methylation of the distal sequences (−996 to −490) (p=0.013 by ANOVA with post hoc testing and Bonferroni correction). Methylation of the core promoter also suppresses promoter function to a greater extent than the distal sequence, but this was of marginal significance (p=0.070). These studies indicate that methylation of the CG pairs between −490 and −229 is transcriptionally relevant, and suppresses promoter function to a greater degree than methylation of the more distal sequences.

Example 13

Demethylation of the CD70 Promoter and 5' Flanking Region in Lupus T Cells

Figure 16:
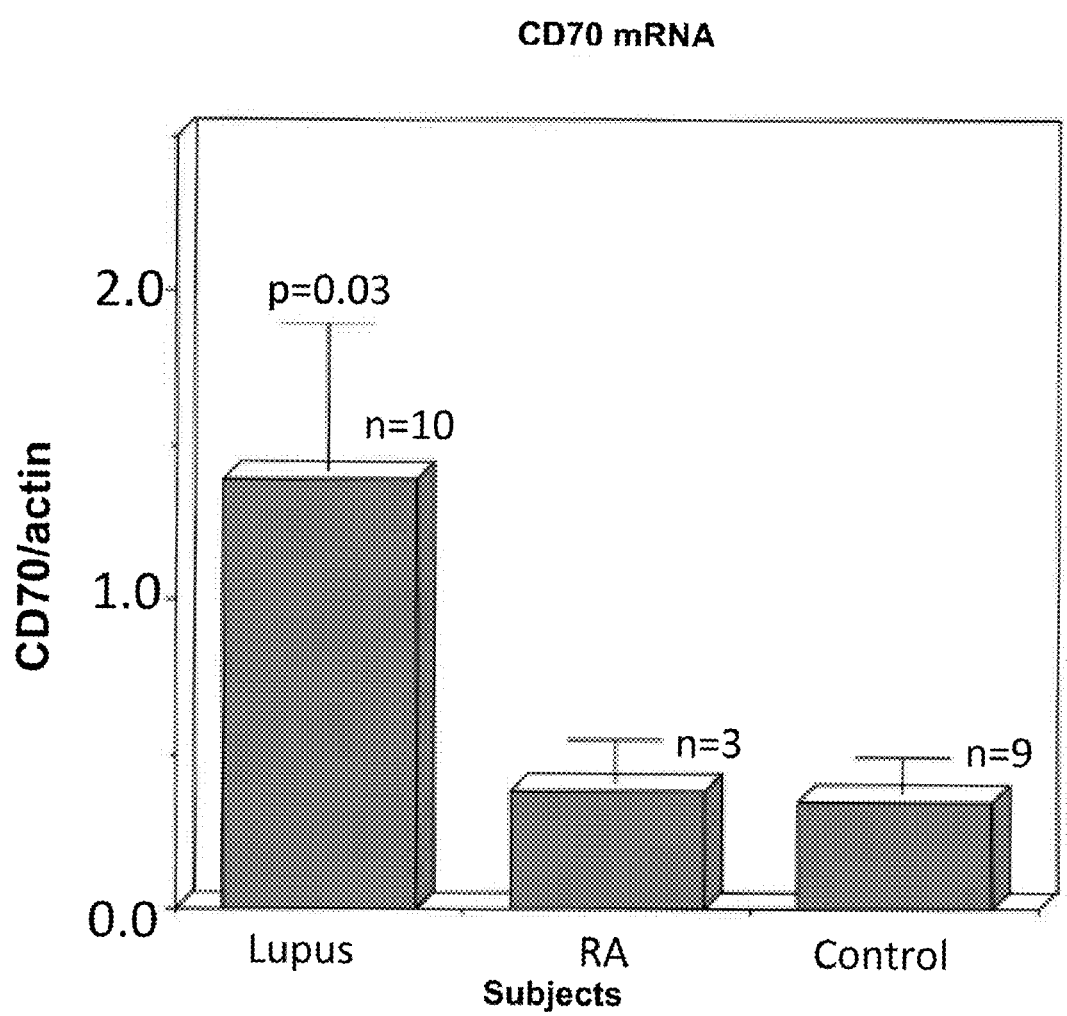
FIG. 16 shows CD70 mRNA levels in CD4+ T cells from lupus patients and controls.
Figure 17:
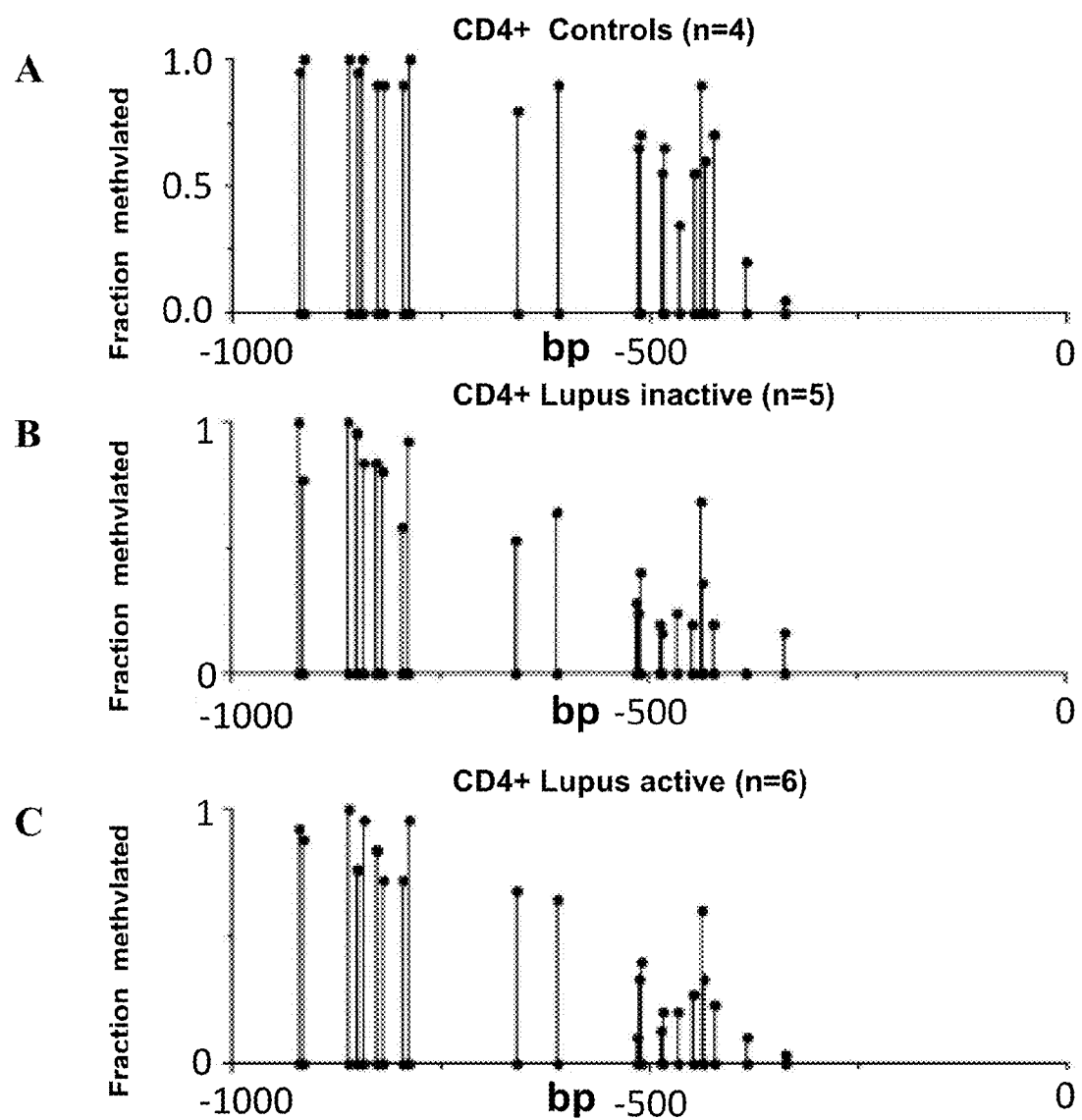
FIG. 17 shows CD70 promoter methylation in CD4+ T cells from lupus patients and controls. (A-C) of the region from −1000 to −200; (D) of the region between −515 and −423.
Figure 17:
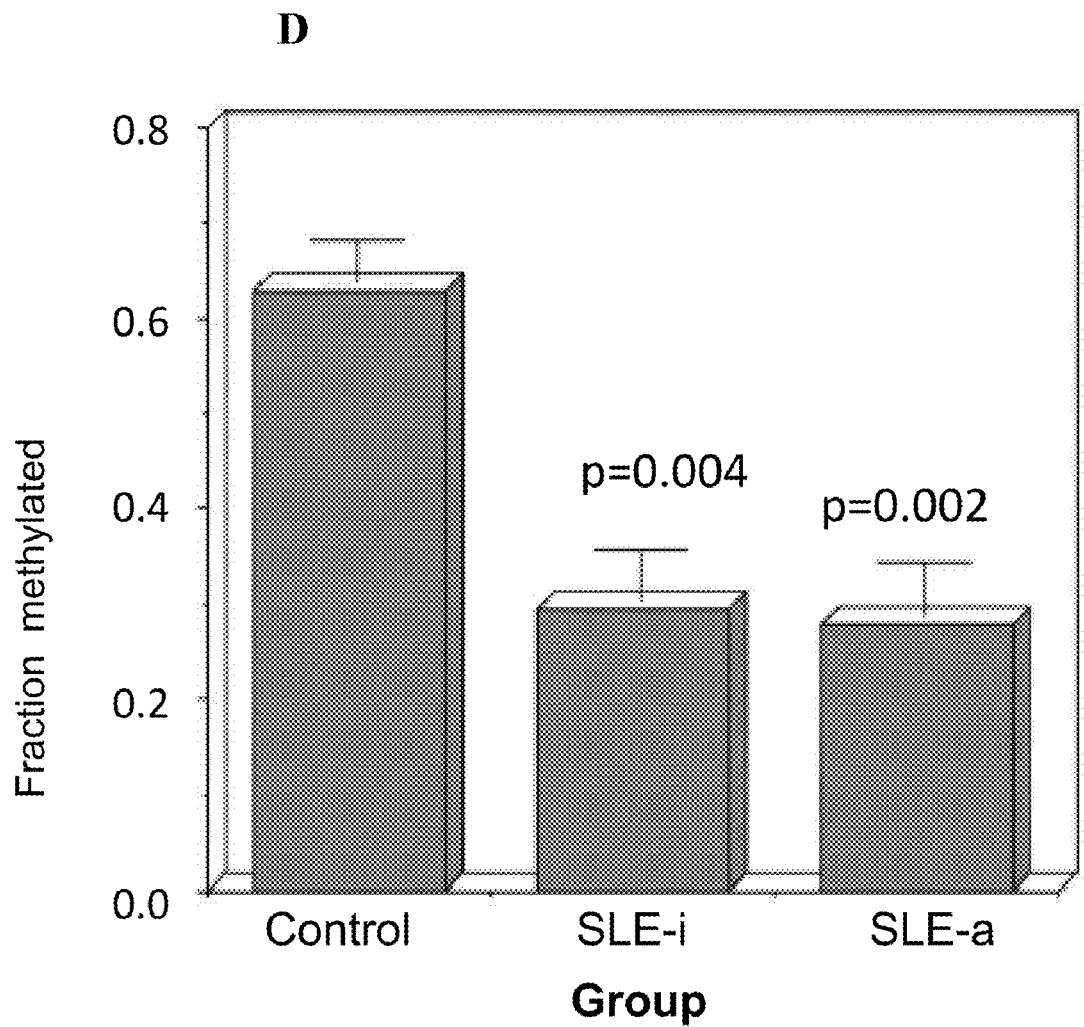

Studies have indicated that CD70 is overexpressed on the surface of CD4+ T cells from patients with active lupus (See, e.g., Oelke et al., Arthritis Rheum 50:1850 (2004)). Thus, an object of the present invention was to define whether the increase was associated with an increase in CD70 mRNA levels. Data obtained and presented in FIG. 16 compares the level of CD70 transcripts in CD4+ T cells from 10 patients with lupus (5 inactive, 5 active), 3 patients with RA and 9 healthy controls (See, e.g., Table 1). CD70 is also significantly (p=0.03 lupus vs controls) increased at the mRNA level in T cells from lupus patients. The difference in CD70 mRNA levels between patients with active and inactive lupus was not significant (1.52±0.74 vs 0.49±0.09, mean±SEM, active vs inactive). No correlation between medications and CD70 expression was observed (See, Table 1).

CD70 promoter methylation patterns of the region from −1000 to −200 were then compared in CD4+ T cells from patients with active and inactive lupus with controls. FIG. 17A shows the methylation pattern in T cells from 4 healthy age and gender matched controls, while FIG. 17B shows the methylation pattern in T cells from 5 women with inactive lupus, and FIG. 17C shows the pattern in 6 women with active lupus. The region from −515 to −423, demethylated by the panel of methylation inhibitors, is also demethylated in CD4+ T cells from lupus patients with both active and inactive disease relative to controls. FIG. 17D compares the average methylation of the region between −515 and −423 across the 3 groups. The overall methylcytosine content is significantly less in lupus than in controls (p=0.004 and 0.002 for inactive and active patients vs controls, respectively, by ANOVA and post hoc testing with Bonferroni correction), similar to T cells demethylated with methylation inhibitors. Again, no correlation with medications was observed (Table 1).

Example 14

Characterization of CD40L Promoter Methylation Status in Healthy and Autoimmune Subjects Using the methods of the present invention (See, e.g., Examples 1-13), the methylation status of the CD40L promoter was analyzed in healthy and autoimmune (e.g., SLE) subjects. Specifically, CD40L gene methylation was determined by bisulfite sequencing (See, e.g., Example 1) in T cells from healthy men and women. The methylation status of the CD40L promoter was analyzed in T cells from healthy women before and after in vitro treatment with procainamide; men and women with lupus; and T cells from healthy men and women treated with the irreversible DNA methylation inhibitor, 5-azaC (See, e.g., Examples 1 and 3). CD40L mRNA measured by RT-PCR (See, e.g., Example 1). CD40L cell-surface expression was measured by flow cytometry with cell-surface expression of CD40L on stimulated T cells compared between healthy controls and men and women with lupus (See, e.g., Examples 1 and 13).

Figure 18:
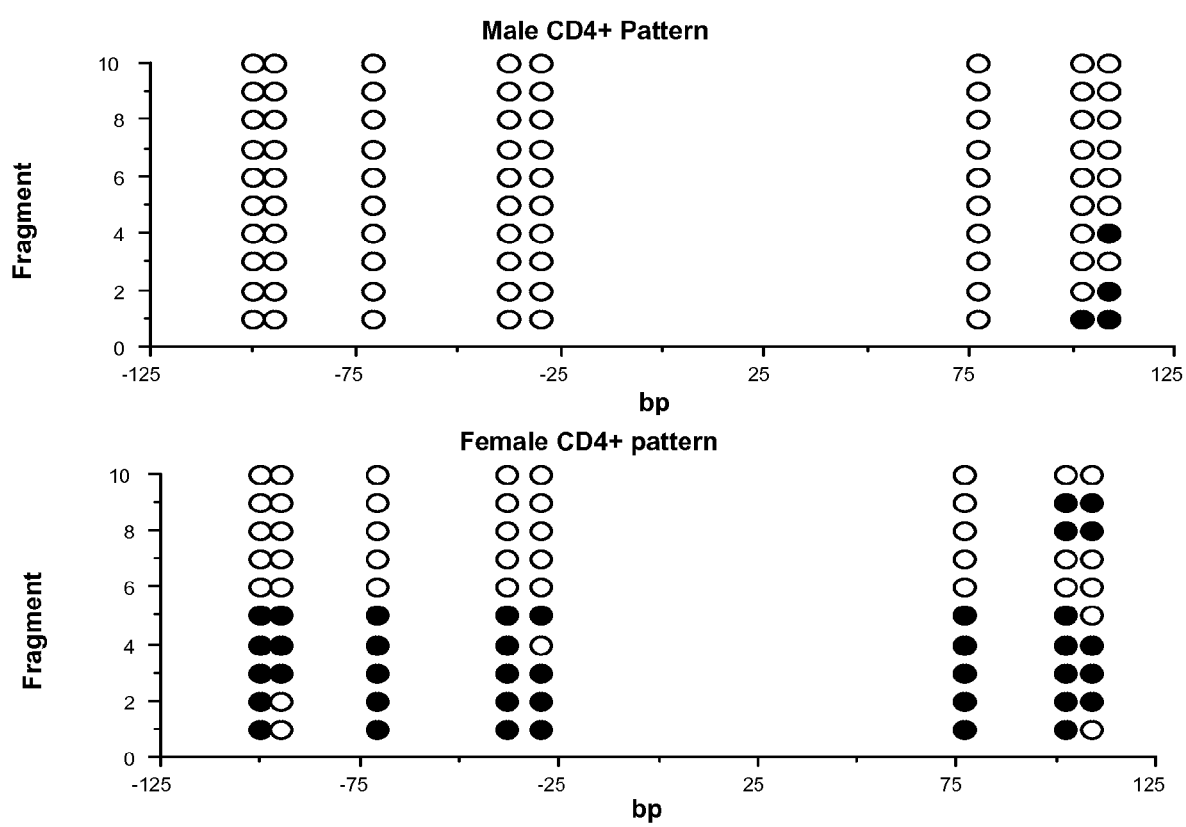
FIG. 18 shows CD40L methylation patterns.
Figure 19:
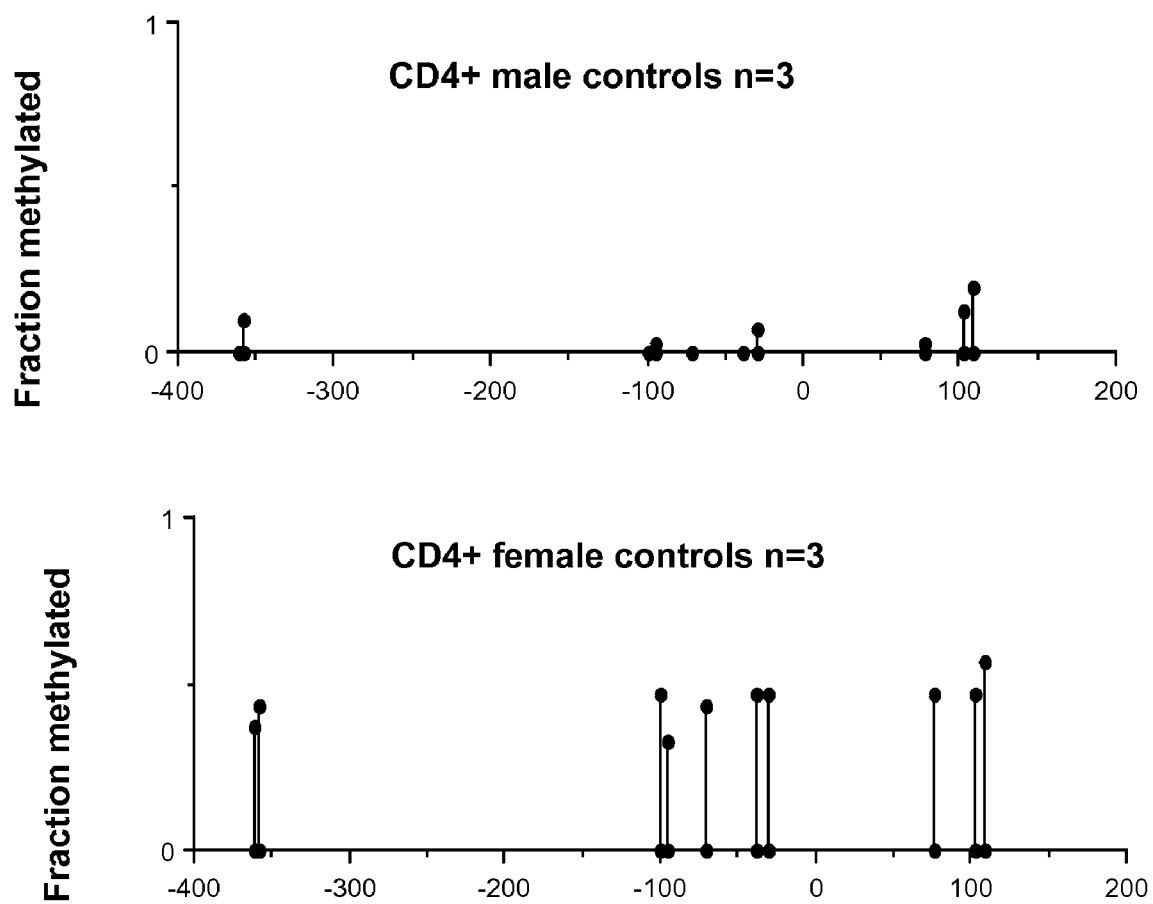
FIG. 19 shows the CD40L promoter methylation in healthy men and women.
Figure 20:
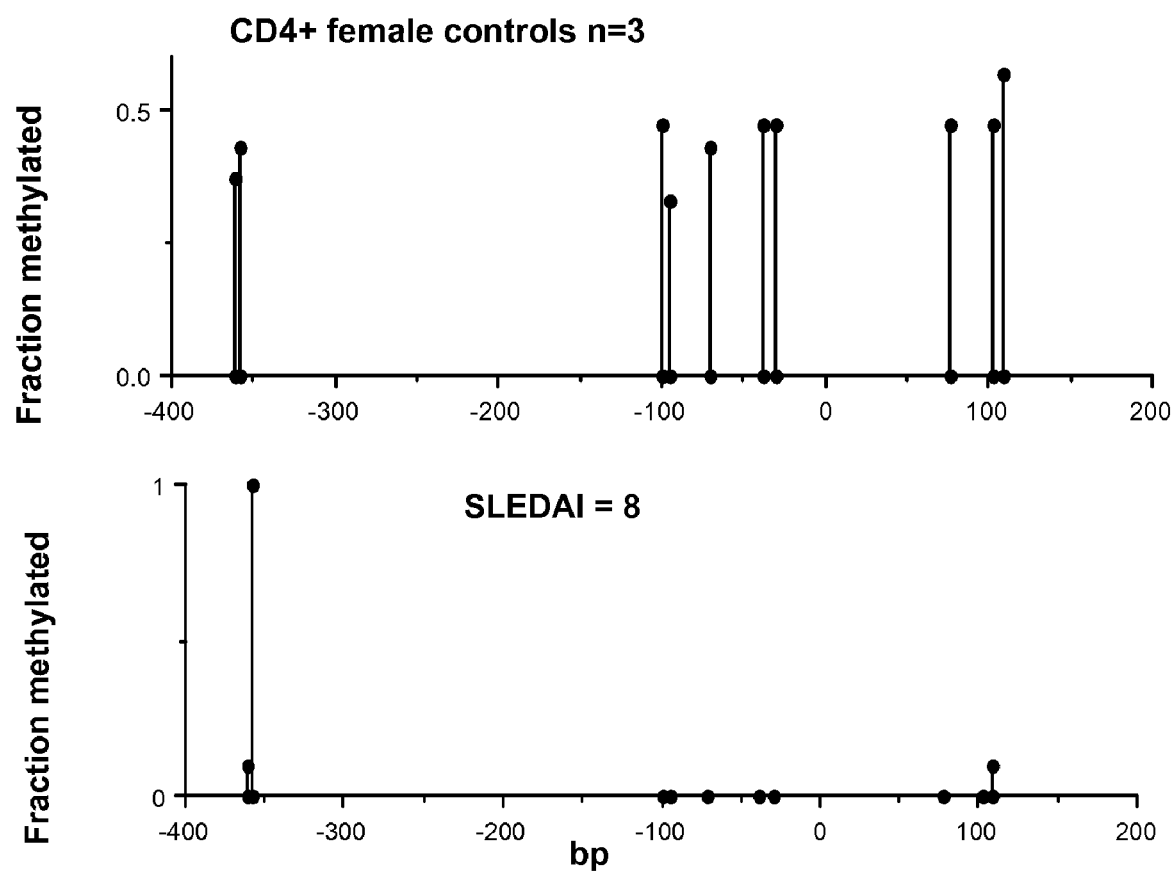
FIG. 20 shows the CD40L promoter is demethylated in CD4+ T cells from a woman with active lupus.
Figure 21:
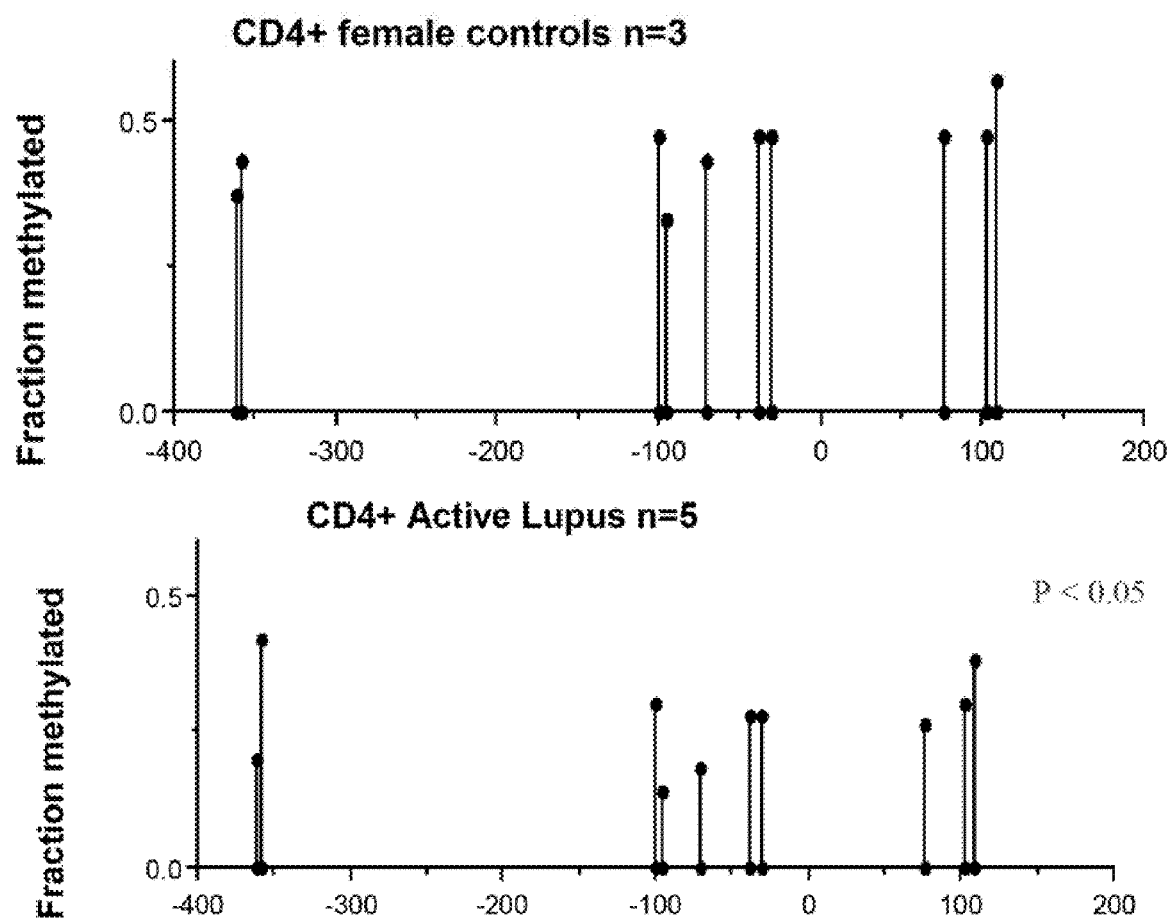
FIG. 21 shows the CD40L Promoter is demethylated in women with lupus.
Figure 22:
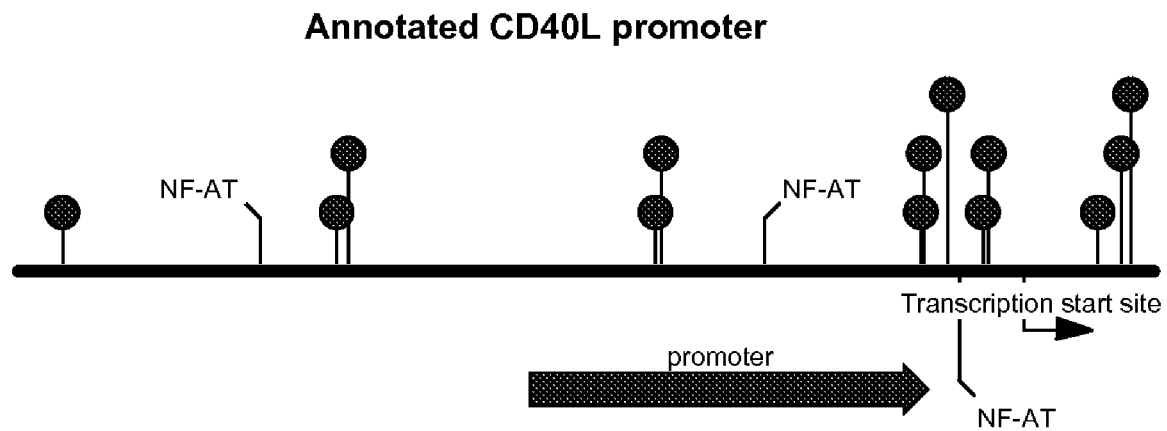
FIG. 22 depicts CD40L promoter map.

The methods of the present invention identified CD40L promoter methylation sites and patterns in healthy men and women (See, e.g., FIG. 18). Closed circles indicate methylated fragments. Furthermore, the methods allowed bisulfite sequencing of CD40L promoter fragments in healthy men and women (See, e.g., FIG. 19). Overall methylation (N=3/grp): men, 6±2%; women, 45±4%. The methods provides data showing that CD40L promoter methylation in CD4+ cells from three healthy women varied from that of a woman with active lupus (See, e.g., FIG. 20). Bars indicate overall percent methylation. These differences were further explored. Thus, FIG. 21 provides CD40L promoter methylation in CD4+ cells from 3 healthy women and 5 women with active lupus. Overall methylation: controls, 45±4%; patients, 18±6% (p=0.001). A diagram of the CD40L promoter is depicted in FIG. 22.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

Sequences:

SEQ ID NO: 1:
5'-TAGGAATTCGTATAATTTAATTTTTAATAAATGTGT-3'

SEQ ID NO: 2:
5'-AACTCTAGATTATCCAACTCTAATCCATACAAAAAAA-3'

SEQ ID NO: 3:
5'-GTGGAATTCGGAATAGGAAGATTGAATGTTTTTGTT-3'

SEQ ID NO: 4:
5'-CTATCTAGAAACCAACCTACCCCTCTCTAAAAATA-3'

SEQ ID NO: 5:
5'-GGTGAATTCTTTAAGGTTAGGAGTTTAAGTTTAGTT-3'

SEQ ID NO: 6:
5'-CAATCTAGAACTACACATTTATTAAAAATTAAATTA-3'

SEQ ID NO: 7:
5'-GTTGAATTCGGTTAATATGGTGAAATTTTATTTTTAT-3'

SEQ ID NO: 8:
5'-CACTCTAGATACAACAAACATCCAAAAATTAAAAATA-3'

SEQ ID NO: 9:
5'-GTTGAATTCGTGAAAATTTATTTTTATTAAAAATAT-3'

SEQ ID NO: 10:
5'-AATTCTAGAAAAAATTTCACCATATTAACCAAACTAA-3'

SEQ ID NO: 11:
5'-TGAGAATTCATTTTTATTAAAAATATAAAAAGTTAGT-3'

SEQ ID NO: 12:
5'-TTATCTAGACTAAACTTAAACTCCTAACCTTAAATA-3'

SEQ ID NO: 13:
5'-TGCTTTGGTCCCATTGGTCG-3'

SEQ ID NO: 14:
5'-TCCTGCTGAGGTCCTGTGTGATTC-3'

SEQ ID NO: 15:
5'-GGACTTCGAGCAAGAGATGG-3'

SEQ ID NO: 16:
5'-AGCACTGTGTTGGCGTACAG-3'

SEQ ID NO: 17:
5'-GCTCTCGAGGTGAAAACCCATCTCTAC-3'

SEQ ID NO: 18:
5'-TCCAAGCTTTCTACTTGCTTCAACCTG-3'

SEQ ID NO: 19:
5'-CAGCTCGAGCAACATGGTGAAACC-3'

SEQ ID NO: 20:
5'-ATTCTCGAGTGTCTGCTGTATCC-3'

---

We claim:

1. A method for detecting the methylation status of CD40L in a subject comprising: a) providing a biological sample from a subject, wherein the biological sample comprises CD40L nucleic acid sequence; b) exposing said sample to reagents for detecting the methylation status of CD40L nucleic acid sequence; c) detecting the methylation status of CD40L nucleic acid sequence in said sample; d) comparing the methylation status of CD40L nucleic acid sequence in said sample to the methylation status of CD40L nucleic acid sequence in a control sample; and e) correlating the methylation status of CD40L nucleic acid sequence in said sample with the presence or absence of systemic lupus erythematosus or rheumatoid arthritis.

2. The method of claim 1, wherein said reagents detect methylation status of the 5' untranslated region of CD40L.

3. The method of claim 2, wherein said 5' untranslated region comprises the 125 to −110 and/or the −350 to −400 region of CD40L.

4. The method of claim 1, wherein said detecting comprises use of a polymerase chain reaction.

5. The method of claim 4, wherein said polymerase chain reaction is methylation sensitive.

6. The method of claim 1, wherein said detecting comprises restriction enzyme digestion.

7. The method of claim 1, wherein said detecting comprises using a kit comprising reagents sufficient for detecting methylation status of CD40L in a subject.

8. The method of claim 1, further comprising detecting methylation status of one or more of CD70, perforin, CD11a, CD11c, IgE FCRγ1, and CD30.

9. The method of claim 1, wherein said detecting comprises an oligonucleotide binding assay.

10. The method of claim 1, wherein said detecting comprises use of a microarray.

11. The method of claim 1, wherein said subject is a healthy subject that does not display symptoms of autoimmune or chronic inflammatory disease.

12. The method of claim 1, wherein said CD40L nucleic acid sequence is DNA.

13. The method of claim 1, wherein said biological sample is selected from the group consisting of bone marrow, whole blood, serum, plasma, interstitial fluid, urine, cerebrospinal fluid, and tissue.

* * * * *